United States Patent [19]

Scartazzini et al.

[11] 4,405,778
[45] Sep. 20, 1983

[54] PROCESS FOR PREPARING CEPHALOSPORIN ETHERS

[75] Inventors: Riccardo Scartazzini, Allschwil; Hans Bickel, Binningen, both of Switzerland

[73] Assignee: Ciba-Geigy Corporation, Ardsley, N.Y.

[21] Appl. No.: 657,904

[22] Filed: Feb. 13, 1976

Related U.S. Application Data

[63] Continuation-in-part of Ser. No. 373,818, Jun. 26, 1973, abandoned.

[30] Foreign Application Priority Data

Jun. 29, 1972 [CH] Switzerland ............................... 9788
Aug. 17, 1972 [CH] Switzerland ............................. 12195
Dec. 22, 1972 [CH] Switzerland ............................. 18722
Feb. 23, 1973 [CH] Switzerland ............................... 2655

[51] Int. Cl.³ ................. C07D 501/04; A61K 31/545
[52] U.S. Cl. ........................................ 544/16; 544/22; 424/246
[58] Field of Search ..................... 544/29, 30, 16, 28, 544/22, 23, 25; 424/246

[56] References Cited

U.S. PATENT DOCUMENTS 3,917,587 11/1975 Chauvette ..................... 260/243 C
3,917,588 11/1975 Chauvette ..................... 260/243 C

*Primary Examiner*—Nicholas S. Rizzo
*Attorney, Agent, or Firm*—Joseph G. Kolodny

[57] ABSTRACT

The invention relates to O-substituted 7β-amino-3-cephem-3-ol-4-carboxylic acid compounds of the formula

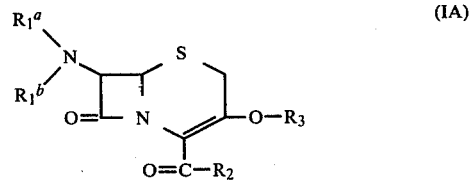

(IA)

wherein $R_1^a$ represents hydrogen or an amino protective group $R_1^A$ and $R_1^b$ represents hydrogen or an acyl group Ac, or $R_1^a$ and $R_1^b$ together represent a bivalent amino protective group, $R_2$ represents hydroxyl or a radical $R_2^A$ which together with the carbonyl grouping —C(=O)— forms a protected carboxyl group and $R_3$ represents an optionally substituted hydrocarbon radical or an acyl group, and to 1-oxides of 3-cephem compounds of the formula I, and also to the corresponding 2-cephem compounds of the formula

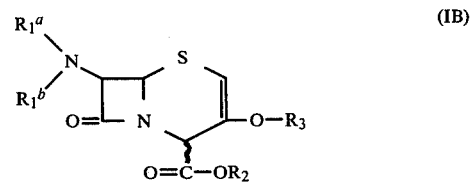

(IB)

wherein $R_1^a$, $R_1^b$, $R_2$ and $R_3$ have the abovementioned meanings, or salts of such compounds with salt-forming groups. 3-Cephem compound of the formula IA, particularly those, in which $R_1^a$ represents an acyl group, $R_1^b$ is hydrogen and $R_2$ is hydroxy exhibit pronounced antimicrobial effects, the others, and particularly the 1-oxides of these 3-cephem compounds and the corresponding 2-cephem compounds are useful as intermediates.

4 Claims, No Drawings

PROCESS FOR PREPARING CEPHALOSPORIN ETHERS

Cross Reference to Related Application

This is a continuation-in-part of our application Ser. No. 373,818, filed June 26, 1973, now abandoned.

The present invention relates to enol derivatives, especially O-substituted 7β-amino-3-cephem-3-ol-4-carboxylic acid compounds of the formula

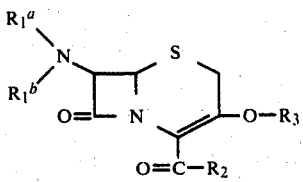

(IA)

wherein $R_1{}^a$ represents hydrogen or an amino protective group $R_1{}^A$ and $R_1{}^b$ represents hydrogen or an acyl group Ac, or $R_1{}^a$ and $R_1{}^b$ together represent a bivalent amino protective group, $R_2$ represents hydroxyl or a radical $R_2{}^A$ which together with the carbonyl grouping —C(=O)— forms a protected carboxyl group and $R_3$ represents an optionally substituted hydrocarbon radical or an acyl group, and to 1-oxides of 3-cephem compounds of the formula I, and also to the corresponding 2-cephem compounds of the formula

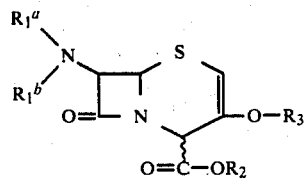

(IB)

wherein $R_1{}^a$, $R_1{}^b$, $R_2$ and $R_3$ have the abovementioned meanings, or salts of such compounds with salt-forming groups, as well as processes for their manufacture and pharmaceutical preparations containing such compounds having pharmacological effects, and their use.

The enol derivatives of the present invention are ethers and esters of 3-cephem-3-ol or 2-cephem-3-ol compounds.

In 2-cephem compounds of the formula IB having the double bond in the 2,3-position, the optionally protected carboxyl group of the formula —C(=O)—R₂ preferably has the α-configuration.

An amino protective group $R_1{}^A$ is a group which can be replaced by hydrogen, above all an acyl group Ac, also a triarylmethyl group, especially the trityl group, as well as an organic silyl group, and an organic stannyl group. A group Ac, which can also represent a radical $R_1{}^b$, above all represents the acyl radical of an organic carboxylic acid, preferably with up to 18 carbon atoms, especially the acyl radical of an optionally substituted aliphatic, cycloaliphatic, cycloaliphatic-aliphatic, aromatic, araliphatic, heterocyclic or heterocyclic-aliphatic carboxylic acid (including formic acid) and the acyl radical of a carbonic acid half-derivative.

A bivalent amino protective group formed by the radicals $R_1{}^a$ and $R_1{}^b$ together is, in particular, the bivalent acyl radical of an organic dicarboxylic acid, preferably with up to 18 carbon atoms, above all the diacyl radical of an aliphatic or aromatic dicarboxylic acid, and also the acyl radical of an α-aminoacetic acid which is preferably substituted in the α-position and contains, for example, an aromatic or heterocyclic radical, and wherein the amino group is bonded to the nitrogen atom via a methylene radical which is preferably substituted and, for example, contains two lower alkyl groups, such as methyl groups. The radicals $R_1{}^a$ and $R_1{}^b$ can together also represent an organic ylidene radical, such as an aliphatic, cycloaliphatic, cycloaliphatic-aliphatic or araliphatic ylidene radical, preferably with up to 18 carbon atoms.

A protected carboxyl group of the formula —C(=O)—R₂ᴬ is above all an esterified carboxyl group but can also be an anhydride group, usually a mixed anhydride group, or an optionally substituted carbamoyl or hydrazino carbonyl group.

The group $R_2{}^A$ can therefore be a hydroxyl group etherified by an organic radical, wherein the organic radical preferably contains up to 18 carbon atoms, which together with the —C(=O)— grouping forms an esterified carboxyl group. Examples of such organic radicals are aliphatic, cycloaliphatic, cycloaliphaticaliphatic, aromatic or araliphatic radicals, especially optionally substituted hydrocarbon radicals of this nature, as well as heterocyclic or heterocyclic-aliphatic radicals.

The group $R_2{}^A$ can also represent an organic silyloxy radical as well as a hydroxyl group etherified by an organometallic radical, such as an appropriate organic stannyloxy group, especially a silyloxy or stannyloxy group which is substituted by 1 to 3, optionally substituted hydrocarbon radicals, preferably with up to 18 carbon atoms, such as aliphatic hydrocarbon radicals, and optionally by halogen, such as chlorine.

A radical $R_2{}^A$ which forms, with the —C(=O)— grouping and anhydride group, above all a mixed anhydride group, is in particular an acyloxy radical, wherein acyl represents the corresponding acyl radical of an organic carboxylic acid, preferably with up to 18 carbon atoms, such as of an aliphatic, cycloaliphatic, cycloaliphatic-aliphatic, aromatic or araliphatic carboxylic acid or of a carbonic acid half-derivative, such as of a carbonic acid half-ester.

A radical $R_2{}^A$ which forms a carbamoyl group with a —C(=O)— grouping is an optionally substituted amino group wherein substituents represent optionally substituted monovalent or bivalent hydrocarbon radicals, preferably with up to 18 carbon atoms, such as optionally substituted monovalent or bivalent aliphatic, cycloaliphatic, cycloaliphatic-aliphatic, aromatic or araliphatic hydrocarbon radicals with up to 18 carbon atoms, also appropriate heterocyclic or heterocyclic-aliphatic radicals with up to 18 carbon atoms and/or functional groups, such as optionally functionally modified, but especially free, hydroxyl and also etherified or esterified hydroxyl, wherein the etherifying or esterifying radicals have, for example, the abovementioned meanings and preferably contain up to 18 carbon atoms, as well as acyl radicals, above all of organic carboxylic acids and of carbonic acid half-derivatives, preferably with up to 18 carbon atoms.

In a substituted hydrazinocarbonyl group of the formula —C(=O)—R₂ᴬ, one or both nitrogen atoms can be substituted, possible substituents being above all optionally substituted monovalent or bivalent hydrocarbon radicals, preferably with up to 18 carbon atoms, such as optionally substituted, monovalent or bivalent aliphatic, cycloaliphatic, cycloaliphatic-aliphatic, aromatic or araliphatic hydrocarbon radicals with up to 18 carbon atoms and also appropriate heterocyclic or heterocyclic-aliphatic radicals with up to 18 carbon atoms and/or functional groups, such as acyl radicals, above all of organic carboxylic acids or of carbonic acid half-derivatives, preferably with up to 18 carbon atoms.

An optionally substituted hydrocarbon radical $R_3$ is preferably an appropriate cycloaliphatic or cycloaliphatic-aliphatic hydrocarbon radical, but especially an optionally substituted aliphatic hydrocarbon radical, and also an appropriate araliphatic hydrocarbon radical. An acyl group $R_3$ is above all the acyl radical of an organic carboxylic acid, including formic acid, such as of a cycloaliphatic, cycloaliphatic-aliphatic, araliphatic, heterocyclic or heterocyclic-aliphatic carboxylic acid, especially the acyl radical of an aliphatic carboxylic acid and also of an aromatic carboxylic acid as well as of a carbonic acid half-derivative.

The general concepts used in the preceding and following description have, for example, the following meanings:

The term "protective group" as employed in connection with functional groups, such as amino, hydroxy and carboxyl, has reference to groups commonly employed in protecting such functional groups during a reaction step and which can be split off subsequently without destroying or substantially destroying the $\beta$-lactam ring system. Such protective groups, the manner of attaching them to the functional group and the manner of their cleavage are wellknown in the art. For example, amino protective groups are described in J.F.W. Mc Omie, "Protective Groups In Organic Chemistry", Plenum Press, New York, N.Y. 1973, Chapter 2, or in E. Schröder and Lübke, "The Peptides", Vol. I, Academic Press 1965, page 72 to 74. Mc Omie, in Chapter 3, describes also hydroxy protective groups, and in Chapter 5 carboxyl protective groups. Carboxyl protective groups are also described by E. Schröder and Lübke on page 75. The terms "protected amino", "protected hydroxy", "protected carboxyl" and the like signifies amino, hydroxy or carboxyl and the like groups being protected or blocked by such protective group.

The term "optionally substituted" indicates that a group may be unsubstituted or substituted.

An aliphatic radical, including the aliphatic radical of an appropriate organic carboxylic acid, as well as an appropriate ylidene radical, is an optionally substituted monovalent or divalent aliphatic hydrocarbon radical, especially lower alkyl, as well as lower alkenyl or lower alkinyl, and also lower alkylidene which can contain, for example, up to 7, preferably up to 4, carbon atoms. Such radicals can optionally be monosubstituted, disubstituted or polysubstituted by functional groups, for example by free, etherified or esterified hydroxyl or mercapto groups, such as lower alkoxy, lower alkenyloxy, lower alkylenedioxy, optionally substituted phenyloxy or phenyl-lower alkoxy, lower alkylthio or optionally substituted phenylthio, phenyl-lower alkylthio, heterocyclylthio or heterocyclyl-lower alkylthio, optionally substituted lower alkoxycarbonyloxy or lower alkanoyloxy, or halogen, also by oxo, nitro, optionally substituted amino, for example lower alkylamino, di-lower alkylamino, lower alkyleneamino, oxa-lower alkyleneamino or aza-lower alkyleneamino, as well as acylamino, such as lower alkanoylamino, lower alkoxycarbonylamino, halogeno-lower alkoxycarbonylamino, optionally substituted phenyl-lower alkoxycarbonylamino, optionally substituted carbamoylamino, ureidocarbonylamino or guanidinocarbonylamino and also sulphoamino which is optionally present in the form of a salt, such as in the form of an alkali metal salt, azido, acyl, such as lower alkanoyl or benzoyl, optionally functionally modified carboxyl, such as carboxyl present in the form of a salt, esterified carboxyl, such as lower alkoxycarbonyl, optionally substituted carbamoyl, such as N-lower alkylcarbamoyl or N,N-di-lower alkylcarbamoyl and also optionally substituted ureidocarbonyl or guanidinocarbonyl, or nitrile, optionally functionally modified sulpho, such as sulphamoyl or sulpho present in the form of a salt, or optionally O-monosubstituted or O,O-disubstituted phosphono, wherein substituents represent, for example, optionally substituted lower alkyl, phenyl or phenyl-lower alkyl, it also being possible for O-unsubstituted or O-monosubstituted phosphono to be in the form of a salt, such as in the form of an alkali metal salt.

A bivalent aliphatic radical, including the appropriate radical of a bivalent aliphatic carboxylic acid, is, for example, lower alkylene or lower alkenylene, which can optionally be monosubstituted, disubstituted or polysubstituted, for example like an aliphatic radical indicated above, and/or be interrupted by heteroatoms, such as oxygen, nitrogen or sulphur.

A cycloaliphatic or cycloaliphatic-aliphatic radical, including the cycloaliphatic or cycloaliphatic-aliphatic radical in an appropriate organic carboxylic acid or an appropriate cycloaliphatic or cycloaliphatic-aliphatic ylidene radical, is an optionally substituted, monovalent or bivalent, cycloaliphatic or cycloaliphatic-aliphatic hydrocarbon radical, for example monocyclic, bicyclic or polycyclic cycloalkyl or cycloalkenyl, and also cycloalkylidene, or cycloalkyl- or cycloalkenyl-lower alkyl or -lower alkenyl, as well as cycloalkyl-lower alkylidene or cycloalkenyl-lower alkylidene, wherein cycloalkyl and cycloalkylidene contains, for example, up to 12, such as 3-8, preferably 3-6, ring carbon atoms, whilst cycloalkenyl contains, for example, up to 12, such as 3-8, for example 5-8, preferably 5 or 6, ring carbon atoms and 1 to 2 double bonds, and the aliphatic part of a cycloaliphatic-aliphatic radical can contain, for example, up to 7, preferably up to 4, carbon atoms. The above cycloaliphatic or cycloaliphatic-aliphatic radicals can, if desired, be monosubstituted, disubstituted or polysubstituted, for example by optionally substituted aliphatic hydrocarbon radicals, such as by the abovementioned optionally substituted lower alkyl groups or, for example, like the abovementioned aliphatic hydrocarbon radicals, by functional groups.

An aromatic radical, including the aromatic radical of an appropriate carboxylic acid, is an optionally substituted aromatic hydrocarbon radical, for example a monocyclic, bicyclic or polycyclic aromatic hydrocarbon radical, especially phenyl, as well as biphenylyl or naphthyl, which can optionally be monosubstituted, disubstituted or polysubstituted, for example like the abovementioned aliphatic and cycloaliphatic hydrocarbon radicals.

A divalent aromatic radical, for example an aromatic carboxylic acid, is above all 1,2-arylene, especially 1,2-phenylene, which can optionally be monosubstituted, disubstituted or polysubstituted, for example like the abovementioned aliphatic and cycloaliphatic hydrocarbon radicals.

An araliphatic radical, including the araliphatic radical in an appropriate carboxylic acid, and also an araliphatic ylidene radical, is, for example, an optionally substituted araliphatic hydrocarbon radical, such as an aliphatic hydrocarbon radical which is optionally substituted and possesses, for example, up to three optionally substituted monocyclic, bicyclic or polycyclic or polycyclic aromatic hydrocarbon radicals, and above all represents phenyl-lower alkyl or phenyl-lower alkenyl as well as phenyl-lower alkinyl and also phenyl-lower alkylidene, it being possible for such radicals to contain, for example, 1-3 phenyl groups and to be optionally monosubstituted, disubstituted or polysubstituted in the aromatic and/or aliphatic part, for example like the abovementioned aliphatic and cycloaliphatic radicals.

Heterocyclic groups, including those in heterocyclic-aliphatic radicals, including heterocyclic or heterocyclic-aliphatic groups in appropriate carboxylic acids, are especially monocyclic, as well as bicyclic or polycyclic, azacyclic, thiacyclic, oxacyclic, thiazacyclic, thiadiazacyclic, oxazacyclic, diazacyclic, triazacyclic or tetrazacyclic radicals of aromatic character, and also appropriate partially or wholly saturated heterocyclic radicals of this nature and such radicals can optionally be monosubstituted, disubstituted or polysubstituted, for example like the abovementioned cycloaliphatic radicals. The aliphatic part in heterocyclic-aliphatic radicals has, for example, the meaning indicated for the corresponding cycloaliphatic-aliphatic or araliphatic radicals.

The acyl radical of a carbonic acid half-derivative is preferably the acyl radical of an appropriate half-ester, wherein the organic radical of the ester group represents an optionally substituted aliphatic, cycloaliphatic, aromatic or araliphatic hydrocarbon radical or a heterocyclic-aliphatic radical, above all the acyl radical of a lower alkyl half-ester of carbonic acid which is optionally substituted, for example in the ($\alpha$- or $\beta$-position, as well as of a lower alkenyl, cycloalkyl, phenyl or phenyl-lower alkyl half-ester of carbonic acid which is optionally substituted in the organic radical. Acyl radicals of a carbonic acid half-ester are furthermore appropriate radicals of lower alkyl half-esters of carbonic acid, in which the lower alkyl part contans a heterocyclic group, for example one of the abovementioned heterocyclic groups of aromatic character, and both the lower alkyl radical and the heterocyclic group can optionally be substituted. The acyl radical of a carbonic acid half-derivative can also be an optionally N-substituted carbamoyl group, such as an optionally halogenated N-lower alkylcarbamoyl group.

An etherified hydroxyl group is above all optionally substituted lower alkoxy, wherein substituents above all represent free or functionally modified, such as etherified or esterified, hydroxyl groups, especially lower alkoxy or halogen, also lower alkenyloxy, cycloalkyloxy or optionally substituted phenyloxy, as well as heterocyclyloxy or heterocyclyl-lower alkoxy especially also optionally substituted phenyl-lower alkoxy.

An optionally substituted amino group is, for example, amino, lower alkylamino, di-lower alkylamino, lower alkyleneamino, oxa-lower alkyleneamino, thia-lower alkyleneamino, aza-lower alkyleneamino, hydroxyamino, lower alkoxyamino, lower alkanoyloxyamino, lower alkoxycarbonylamino or lower alkanoylamino.

An optionally substituted hydrazino group is, for example, hydrazino, 2-lower alkylhydrazino, 2,2-di-lower alkylhydrazino, 2-lower alkoxycarbonylhydrazino or 2-lower alkanoylhydrazino.

Lower alkyl is, for example, methyl, ethyl, n-propyl, isopropyl, n-butyl, isobutyl, sec.-butyl or tert.-butyl, as well as n-pentyl, isopentyl, n-hexyl, isohexyl or n-heptyl, whilst lower alkenyl can, for example, be vinyl, allyl, isopropenyl, 2- or 3-methallyl or 3-butenyl, lower alkinyl can, for example, be propargyl or 2-butinyl and lower alkylidene can, for example, be isopropylidene or isobutylidene.

Lower alkylene is, for example, 1,2-ethylene, 1,2- or 1,3-propylene, 1,4-butylene, 1,5-pentylene, or 1,6-hexylene, whilst lower alkenylene is, for example, 1,2-ethenylene or 2-buten-1,4-ylene. Lower alkylene interrupted by hetero-atoms is, for example, oxa-lower alkylene, such as 3-oxa-1,5-pentylene, thia-lower alkylene, such as 3-thia-1,5-pentylene, or aza-lower alkylene, such as 3-lower alkyl-3-aza-1,5-pentylene, for example 3-methyl-3-aza-1,5-pentylene.

Cycloalkyl is, for example, cyclopropyl, cyclobutyl, cyclopentyl, cyclohexyl or cycloheptyl as well as adamantyl, whilst cycloalkenyl is, for example, cyclopropenyl, 1-, 2- or 3-cyclopentenyl, 1-, 2- or 3-cyclohexenyl, 3-cycloheptenyl or 1,4-cyclohexadienyl and cycloalkylidene is, for example, cyclopentylidene or cyclohexylidene. Cycloalkyl-lower alkyl or -lower alkenyl is, for example, cyclopropyl-, cyclopentyl-, cyclohexyl- or cycloheptyl-methyl, -1,1- or -1,2-ethyl, -1,1-, -1,2- or -1,3-propyl, -vinyl or -allyl, whilst cycloalkenyl-lower alkyl or -lower alkenyl represents, for example, 1-, 2- or 3-cyclopentenyl-, 1-, 2- or 3-cyclohexenyl- or 1-, 2- or 3-cycloheptenyl-methyl, -1,1- or -1,2-ethyl, -1,1-,-1,2- or -1,3-propyl, -vinyl or -allyl. Cycloalkyl-lower alkylidene is, for example, cyclohexylmethylene, and cycloalkenyl-lower alkylidene is, for example, 3-cyclohexenylmethylene.

Naphthyl is 1- or 2-naphthyl, whilst biphenylyl represents, for example, 4-biphenylyl.

Phenyl-lower alkyl or phenyl-lower alkenyl is, for example, benzyl, 1- or 2-phenylethyl, 1-, 2- or 3-phenylpropyl, diphenylmethyl, trityl, styryl or cinnamyl, naphthyl-lower alkyl is, for example, 1- or 2-naphthylmethyl and phenyl-lower alkylidene is, for example, benzylidene.

Heterocyclic radicals are above all optionally substituted heterocyclic radicals of aromatic character, for example appropriate monocyclic, monoazacyclic, monothiacyclic or monooxacyclic radicals, such as pyrryl, for example 2-pyrryl or 3-pyrryl, pyridyl, for example 2-, 3- or 4-pyridyl and also pyridinium, thienyl, for example 2- or 3-thienyl, or furyl, for example 2-furyl, bicyclic monoazacyclic, monooxacyclic or monothiacyclic radicals, such as indolyl, for example 2- or 3-indolyl, quinolinyl, for example 2- or 4-quinolinyl, isoquinolinyl, for example 1-isoquinolinyl, benzofuranyl, for example 2- or 3-benzofuranyl, or benzothienyl, for example 2- or 3-benzothienyl, monocyclic diazacyclic, triazacyclic, tetrazacyclic, oxazacyclic, thiazacyclic or thiadiazacyclic radicals, such as imidazolyl, for example 2-imidazolyl, pyrimidinyl, for example 2- or 4-pyrimidinyl, triazolyl, for example 1,2,4-triazol-3-yl, tetrazolyl, for example 1- or 5-tetrazolyl, oxazolyl, for example 2-oxazolyl, isoxazolyl, for example 3- or 4-isoxazolyl, thiazolyl, for example 2-thiazolyl, isothiazolyl, for example 3- or 4-isothiazolyl, or 1,2,4- or 1,3,4-thiadiazolyl, for example 1,2,4-thiadiazol-3-yl or 1,3,4-thiadiazol-2-yl, or bicyclic diazacyclic, oxazacyclic or thiazacyclic radicals, such as benzimidazolyl, for example 2-benzimidazolyl, benzoxazolyl, for example 2-benzoxazolyl, or benzthiazolyl, for example 2-benzthiazolyl. Appropriate partially or wholly saturated radicals are, for example, tetrahydrothienyl, such as 2-tetrahydrothienyl, tetrahydrofuryl, such as 2-tetrahydrofuryl, or piperidyl, for example 2- or 4-piperidyl. Heterocyclic-aliphatic radicals are lower alkyl or lower alkenyl containing heterocyclic groups, especially those mentioned above. The abovementioned heterocyclic radicals can be substituted, for example by optionally substituted aliphatic or aromatic hydrocarbon radicals, especially lower alkyl, such as methyl, or phenyl which is optionally substituted, for example by halogen such as chlorine, for example phenyl or 4-chlorophenyl, or, for example like the aliphatic hydrocarbon radicals, by functional groups.

Lower alkoxy is, for example, methoxy, ethoxy, n-propoxy, isopropoxy, n-butoxy, isobutoxy, sec.-butoxy, tert.-butoxy, n-pentoxy or tert.-pentoxy. These groups can be substituted, for example as in halogen-lower alkoxy, especially 2-halogen-lower alkoxy, for example 2,2,2-trichloroethoxy, 2-chloroethoxy, 2-bromoethoxy or 2-iodoethoxy. Lower alkenyloxy is, for example, vinyloxy or allyloxy, lower alkylenedioxy is, for example, methylenedioxy, ethylenedioxy or isopropylenedioxy, cycloalkoxy is, for example, cyclopentyloxy, cyclohexyloxy or adamantyloxy, phenyl-lower alkoxy is, for example, benzyloxy, 1- or 2-phenylethoxy, diphenylmethoxy or 4,4'-dimethoxydiphenylmethoxy, or heterocyclyloxy or heterocyclyl-lower alkoxy is, for example, pyridyl-lower alkoxy, such as 2-pyridylmethoxy, furyl-lower alkoxy, such as furfuryloxy, or thienyl-lower alkoxy, such as 2-thenyloxy.

Lower alkylthio is, for example, methylthio, ethylthio or n-butylthio, lower alkenylthio is, for example, allylthio, and phenyl-lower alkylthio is, for example, benzylthio, whilst mercapto groups etherified by heterocyclyl radicals or heterocyclyl-aliphatic radicals are especially pyridylthio, for example 4-pyridylthio, imidazolylthio, for example 2-imidazolylthio, thiazolylthio, for example 2-thiazolylthio, 1,2,4- or 1,3,4-thiadiazolylthio, for example 1,2,4-thiadiazol-3-ylthio or 1,3,4-thiadiazol-2-ylthio, or tetrazolylthio, for example 1-methyl-5-tetrazolylthio.

Esterified hydroxyl groups are above all halogen, for example fluorine, chlorine, bromine or iodine, as well as lower alkanoyloxy, for example acetoxy or propionyloxy, lower alkoxycarbonyloxy, for example methoxycarbonyloxy, ethoxycarbonyloxy or tert.-butoxycarbonyloxy, 2-halogeno-lower alkoxycarbonyloxy, for example 2,2,2-trichloroethoxycarbonyloxy, 2-bromoethoxycarbonyloxy or 2-iodoethoxycarbonyloxy, or arylcarbonylmethoxycarbonyloxy, for example phenacyloxycarbonyloxy.

Lower alkoxycarbonyl is, for example, methoxycarbonyl, ethoxycarbonyl, n-propoxycarbonyl, isopropoxycarbonyl, tert.-butoxycarbonyl or tert.-pentoxycarbonyl.

N-Lower alkyl- or N,N-di-lower alkyl-carbamoyl is, for example, N-methylcarbamoyl, N-ethylcarbamoyl, N,N-dimethylcarbamoyl or N,N-diethylcarbamoyl, whilst N-lower alkylsulphamoyl represents, for example, N-methylsulphamoyl or N,N-dimethylsulphamoyl.

A carboxyl or sulpho present in the form of an alkali metal salt is, for example, a carboxyl or sulpho present in the form of a sodium or potassium salt.

Lower alkylamino or di-lower alkylamino is, for example, methylamino, ethylamino, dimethylamino or diethylamino, lower alkyleneamino is, for example, pyrrolidino or piperidino, oxa-lower alkyleneamino is, for example, morpholino, thia-lower alkyleneamino is, for example, thiomorpholino, and aza-lower alkyleneamino is, for example piperazino or 4-methylpiperazino. Acylamino in particular represents carbamoylamino, lower alkylcarbamoylamino, such as methylcarbamoylamino, ureidocarbonylamino, guanidinocarbonylamino, lower alkoxycarbonylamino, for example methoxycarbonylamino, ethoxycarbonylamino or tert.-butoxycarbonylamino, halogeno-lower alkoxycarbonylamino, such as 2,2,2-trichloroethoxycarbonylamino, phenyl-lower alkoxycarbonylamino, such as 4-methoxybenzyloxycarbonylamino, lower alkanoylamino, such as acetylamino or propionylamino, and also phthalimido, or sulphoamino optionally present in the form of a salt, such as in the form of an alkali metal salt, for example in the form of a sodium salt or ammonium salt, Lower alkanoyl is, for example, formyl, acetyl, propionyl or pivaloyl.

O-lower alkyl-phosphono is, for example, O-methyl- or O-ethyl-phosphono, O,O'-di-lower alkyl-phosphono is, for example, O,O'-dimethyl-phosphono or O,O'-diethylphosphono, O-phenyl-lower alkyl-phosphono is, for example, O-benzyl-phosphono, and O-lower alkyl-O'-phenyl-lower alkyl-phosphono is, for example, O-benzyl-O'-methyl-phosphono.

Lower alkenyloxycarbonyl is, for example, vinyloxycarbonyl, whilst cycloalkoxycarbonyl and phenyl-lower alkoxycarbonyl represent, for example, adamantyloxycarbonyl, benzyloxycarbonyl, 4-methoxy-benzyloxycarbonyl, diphenylmethoxycarbonyl or α-4-biphenylyl-α-methyl-ethoxycarbonyl. Lower alkoxycarbonyl, wherein lower alkyl contains, for example, a monocyclic, monoazacyclic, monooxacyclic or monothiacyclic group, is, for example, furyl-lower alkoxycarbonyl, such as furfuryloxycarbonyl, or thienyl-lower alkoxycarbonyl, such as 2-thenyloxycarbonyl.

2-Lower alkylhydrazino and 2,2-di-lower alkylhydrazino are, for example, 2-methylhydrazino or 2,2-dimethylhydrazino, 2-lower alkoxycarbonylhydrazino is, for example 2-methoxycarbonylhydrazino, 2-ethoxycarbonylhydrazino or 2-tert.-butoxycarbonylhydrazino and lower alkanoylhydrazino is, for example, 2-acetylhydrazino.

An acyl group Ac in particular represents an acyl radical of an organic carboxylic acid, preferably with up to 18 carbon atoms, contained in a naturally occurring or biosynthetically, semi-synthetically or total-synthetically obtainable, preferably pharmaceutically active, N-acyl derivative of a 6-amino-penam-3-carboxylic acid compound or 7-amino-3-cephem-4-carboxylic acid compound, or represents an easily removable acyl radical, especially of a carbonic acid half-derivative.

An acyl radical Ac contained in a pharmacologically active N-acyl derivative of a 6-amino-penam-3-carboxylic acid compound or 7-amino-3-cephem-4-carboxylic acid compound is above all a group of the formula

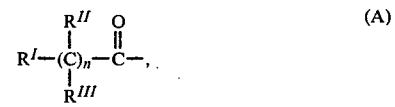

wherein n represents 0 and $R^I$ denotes hydrogen or an optionally substituted cycloaliphatic or aromatic hydrocarbon radical or an optionally substituted heterocyclic radical, preferably of aromatic character, a functionally modified, for example esterified or etherified, hydroxyl or mercapto group or an optionally substituted amino group, or wherein n represents 1, $R^I$ represents hydrogen or an optionally substituted aliphatic, cycloaliphatic, cycloaliphatic-aliphatic, aromatic or araliphatic hydrocarbon radical or an optionally substituted heterocyclic or heterocyclic-aliphatic radical, wherein the heterocyclic radical preferably possesses aromatic character and/or a quaternary nitrogen atom, an optionally functionally modified, preferably etherified or esterified, hydroxyl or mercapto group, an optionally functionally modified carboxyl group, an acyl group, an optionally substituted amino group or an azido group and each of the radicals $R^{II}$ and $R^{III}$ represents hydrogen, or wherein n represents 1, $R^I$ denotes an optionally substituted aliphatic, cycloaliphatic, cycloaliphatic-aliphatic, aromatic or araliphatic hydrocarbon radical or an optionally substituted heterocyclic or heterocyclic-aliphatic radical, wherein the heterocyclic radical preferably has aromatic character, $R^{II}$ denotes an optionally functionally modified, for example esterified or etherified, hydroxyl or mercapto group, such as a halogen atom, an optionally substituted amino group, an optionally functionally modified carboxyl or sulpho group, an optionally O-monosubstituted or O,O'-disubstituted phosphono group or an azido group, whereby $R^{II}$ cannot be an optionally substituted amino group, when $R^I$ is 1,4-cyclohexadienyl, and $R^{III}$ represents hydrogen, or wherein n represents 1, each of the radicals $R^I$ and $R^{II}$ denotes a functionally modified, preferably etherified or esterified, hydroxyl group or an optionally functionally modified carboxyl group, and $R^{III}$ represents hydrogen, or wherein n represents 1, $R^I$ denotes hydrogen or an optionally substituted aliphatic, cycloaliphatic, cycloaliphatic-aliphatic, aromatic or araliphatic hydrocarbon radical and $R^{II}$ and $R^{III}$ together represent an optionally substituted aliphatic, cycloaliphatic, cycloaliphaticaliphatic or araliphatic hydrocarbon radical which is bonded to the carbon atom by a double bond, or wherein n represents 1 and $R^I$ denotes an optionally substituted aliphatic, cycloaliphatic, cycloaliphatic-aliphatic, aromatic or araliphatic hydrocarbon radical or an optionally substituted heterocyclic or heterocyclic-aliphatic radical, wherein heterocyclic radicals preferably possess aromatic character, $R^{II}$ denotes an optionally substituted aliphatic, cycloaliphatic, cycloaliphatic-aliphatic, aromatic or araliphatic hydrocarbon radical and $R^{III}$ denotes hydrogen or an optionally substituted aliphatic, cycloaliphatic, cycloaliphatic-aliphatic, aromatic or araliphatic hydrocarbon radical.

An acyl group of the formula A can for example be a group of the formula

(A₁)

wherein $R^I$ represents hydrogen or a cycloalkyl group with 5-7 ring carbon atoms which is optionally substituted, preferably in the 1-position, by optionally protected amino, such as amino, acylamino, wherein acyl above all represents the acyl radical of a carbonic acid half-ester, such as a lower alkoxycarbonyl, 2-halogeno-lower alkoxycarbonyl or phenyl-lower alkoxycarbonyl radical, or a sulphoamino group which is optionally present in the form of a salt, for example in the form of an alkali metal salt, a phenyl, naphthyl or tetrahydronaphthyl group which is optionally substituted, preferably by hydroxyl, lower alkoxy, for example methoxy, acyloxy, wherein acyl above all represents the acyl radical of a carbonic acid half-ester, such as a lower alkoxycarbonyl, 2-halogeno-lower alkoxycarbonyl or phenyl-lower alkoxycarbonyl radical, and/or halogen, for example chlorine, a heterocyclic group which is optionally substituted, for example by lower alkyl, for example methyl and/or phenyl, which can in turn carry substituents, such as halogen, for example chlorine, such as a 4-isoxazolyl group, or an amino group which is preferably N-substituted, for example by an optionally substituted lower alkyl radical, such as a lower alkyl radical containing halogen, for example chlorine, or an acyl group of the formula (A) can be an acyl group of the formula

(A₂)

wherein $R^I$ represents a lower alkyl group which is optionally substituted, preferably by halogen, such as chlorine, by phenyloxy which is optionally substituted, such as phenyloxy containing hydroxyl, acyloxy, wherein acyl has the abovementioned meaning, and/or halogen, for example chlorine, or by optionally protected amino and/or carboxyl, for example a 3-amino-3-carboxyl-propyl radical which has an optionally protected amino and/or carboxyl group, for example a silylated, such as tri-lower alkylsilylated, for example trimethylsilylated, amino or acylamino, such as lower alkanoylamino, halogeno-lower alkanoylamino or phthaloylamino group, and/or a silylated, such as tri-lower alkylsilylated, for example trimethylsilylated, carboxyl group, or an esterified carboxyl group, such as a carboxyl group which is esterified by lower alkyl, 2-halogeno-lower alkyl or phenyl-lower alkyl, for example diphenylmethyl, or represents a lower alkenyl group, a phenyl group which is optionally substituted, such as a phenyl group which optionally contains hydroxyl which is acylated, for example as indicated above, and/or halogen, for example chlorine, and also optionally protected amino-lower alkyl, such as aminomethyl, which is optionally protected, for example acylated as indicated above, or phenyloxy which is optionally substituted, such as phenyloxy which possesses hydroxyl which is optionally acylated, for example as indicated above, and/or halogen, for example chlorine, or represents a pyridyl group, for example 4-pyridyl group, pyridinium group, for example 4-pyridinium group, thienyl group, for example 2-thienyl group, furyl group, for example 2-furyl group, imidazolyl group, for example 1-imidazolyl group, or a tetrazolyl group, for example 1-tetrazolyl group, which are optionally substituted, for example by lower alkyl, such as methyl, or by amino or aminomethyl which are optionally protected, for example acylated as indicated above, or represents an optionally substituted lower alkoxy group, for example a methoxy group, a phenyloxy group which is optionally substituted, such as a phenyloxy group which contains optionally protected hydroxyl, for example hydroxyl acylated as indicated above, and/or halogen, such as chlorine, or represents a lower alkylthio group, for example n-butylthio group, or lower alkenylthio group, for example allylthio group, a phenylthio, pyridylthio, for example 4-pyridylthio, 2-imidazolylthio, 1,2,4-triazol-3-ylthio, 1,3,4-triazol-2-ylthio, 1,2,4-thiadiazol-3-ylthio, such as 5-methyl-1,2,4-thiadiazol-3-ylthio, 1,3,4-thiadiazol-2-ylthio, such as 5-methyl-1,3,4-thiadiazol-2-ylthio, or 5-tetrazolylthio, such as 1-methyl-5-tetrazolylthio group, which are optionally substituted, for example by lower alkyl, such as methyl, or represents a halogen atom, especially chlorine or bromine atom, an optionally functionally modified carboxyl group, such as lower alkoxycarbonyl, for example methoxycarbonyl or ethoxycarbonyl, nitrile or carbamoyl which is optionally N-substituted, for example by lower alkyl, such as methyl, or phenyl, or represents an optionally substituted lower alkanoyl group, for example an acetyl or propionyl group, or a benzyl group, or an azido group, or an acyl group of the formula (A) can be an acyl group of the formula

wherein $R^I$ represents lower alkyl or a phenyl, furyl, for example 2-furyl, thienyl, for example 2- or 3-thienyl, or isothiazolyl, for example 4-isothiazolyl group which is optionally substituted, such as substituted by hydroxyl which is optionally acylated, for example as indicated above, and/or by halogen, for example chlorine, $R^{II}$ represents optionally protected or substituted amino, for example amino, acylamino, such as lower alkoxycarbonylamino, 2-halogeno-lower alkoxycarbonylamino or optionally substituted phenyl-lower alkoxycarbonylamino such as phenyl-lower alkoxycarbonylamino which contains lower alkoxy, for example methoxy, or nitro, for example tert.-butoxycarbonylamino, 2,2,2-trichloroethoxycarbonylamino, 4-methoxybenzyloxycarbonylamino or diphenylmethyloxycarbonylamino, arylsulphonylamino, for example 4-methylphenylsulphonylamino, tritylamino, arylthioamino, such as nitrophenylthioamino, for example 2-nitrophenylthioamino, or tritylthioamino or 2-propylideneamino which is optionally substituted, such as 2-propylideneamino which contains lower alkoxycarbonyl, for example ethoxycarbonyl, or lower alkanoyl, for example acetyl, such as 1-ethoxycarbonyl-2-propylideneamino, or optionally substituted carbamoylamino, such as guanidinocarbonylamino, or a sulphoamino group which is optionally present in the form of a salt, for example in the form of an alkali metal salt, an azido group, a carboxyl group which is optionally present in the form of a salt, for example in the form of an alkali metal salt, or in a protected form, such as in an esterified form, for example as a lower alkoxycarbonyl group, for example a methoxycarbonyl group or ethoxycarbonyl group, or as a phenyloxycarbonyl group, for example a diphenylmethoxycarbonyl group, a nitrile group, a sulpho group, an optionally functionally modified hydroxyl group, wherein functionally modified hydroxyl in particular represents protected hydroxyl, for example acyloxy, such as formyloxy, as well as lower alkoxycarbonyloxy, 2-halogeno-lower alkoxycarbonyloxy or phenyl-lower alkoxycarbonyloxy which is optionally substituted, such as phenyl-lower alkoxycarbonyloxy which contains lower alkoxy, for example methoxy, or nitro, for example tert.-butoxycarbonyloxy, 2,2,2-trichloroethoxycarbonyloxy, 4-methoxybenzyloxycarbonyloxy or diphenylmethoxycarbonyloxy, or optionally substituted lower alkoxy, for example methoxy or phenyloxy, a O-lower alkyl-phosphono group or O,O'-di-lower alkyl-phosphono group, for example O-methyl-phosphono or O,O'-dimethylphosphono, or a halogen atom, for example chlorine or bromine, whereby $R^I$ can also be 1,4-cyclohexadienyl, if $R^{II}$ is a carboxyl group which is optionally present in the form of a salt, for example in the form of an alkali metal salt, or in a protected form, such as in an esterified form, for example as a lower alkoxycarbonyl group, for example a methoxycarbonyl group or ethoxycarbonyl group, or as a phenyloxycarbonyl group, for example a diphenylmethoxycarbonyl group, a nitrile group, a sulpho group, an optionally functionally modified hydroxyl group, wherein functionally modified hydroxyl in particular represents protected hydroxyl, for example acyloxy, such as formyloxy, as well as particular represents acyloxy, such as formyloxy, as well as lower alkoxycarbonyloxy, 2-halogeno-lower alkoxycarbonyloxy or phenyl-lower alkoxycarbonyloxy which is optionally substituted, such as phenyl-lower alkoxycarbonyloxy which contains lower alkoxy, for example methoxy, or nitro, for example tert.-butoxycarbonyloxy, 2,2,2-trichloroethoxycarbonyloxy, 4-methoxybenzyloxycarbonyloxy or diphenylmethoxycarbonyloxy, or optionally substituted lower alkoxy, for example methoxy or phenyloxy, a O-lower alkyl-phosphono group or O,O'-di-lower alkyl-phosphono group, for example O-methyl-phosphono or O,O'-dimethylphosphono, or a halogen atom, for example chlorine or bromine, or an acyl group of the formula (A) can be an acyl group of the formula

wherein $R^I$ and $R^{II}$ each represent halogen, for example bromine, or lower alkoxycarbonyl, for example methoxycarbonyl, or an acyl group of the formula (A) can be an acyl group of the formula

wherein $R^I$ represents phenyl, furyl, for example 2-furyl, or thienyl, for example 2- or 3-thienyl, or isothiazolyl, for example 4-isothiazolyl, which are optionally substituted, for example by hydroxyl which is optionally acylated, for example as indicated above, and/or by halogen, for example chlorine, and also represents a 1,4-cyclohexadienyl group, $R^{II}$ represents aminomethyl which is optionally protected, for example as indicated above, or an acyl group of the formula (A) can be an acyl group of the formula

wherein each of the groups $R^I$, $R^{II}$ and $R^{III}$ represents lower alkyl, for example methyl.

Such acyl radicals Ac are, for example, formyl, cyclopentylcarbonyl, α-aminocyclopentylcarbonyl or α-aminocyclohexylcarbonyl (with an optionally substituted amino group, for example a sulphoamino group optionally present in the form of a salt, or an amino group which is substituted by an acyl radical which can be split off, preferably easily, for example on treatment with an acid agent, such as trifluoroacetic acid, or by reduction, for example on treatment with a chemical reducing agent, such as zinc in the presence of aqueous acetic acid, or catalytic hydrogen, or hydrolytically, or an acyl radical which can be converted into such a radical, preferably a suitable acyl radical of a carbonic acid halfester, such as lower alkoxycarbonyl, for example tert.-butoxycarbonyl, 2-halogeno-lower alkylcarbonyl, for example 2,2,2-trichloroethoxycarbonyl, 2-bromoethoxycarbonyl or 2-iodoethoxycarbonyl, arylcarbonylmethoxycarbonyl, for example phenacyloxycarbonyl, optionally substituted phenyl-lower alkoxycarbonyl, such as phenyl-lower alkoxycarbonyl containing lower alkoxy, for example methoxy, or nitro, for example 4-methoxybenzyloxycarbonyl or diphenylmethoxycarbonyl, or of a carbonic acid half-amide, such as carbamoyl or N-substituted carbamoyl, such as N-lower alkylcarbamoyl, for example N-methylcarbamoyl, as well as by trityl, also by arylthio, for example 2-nitrophenylthio, arylsulphonyl, for example 4-methylphenylsulphonyl or 1-lower alkoxycarbonyl-2-propylidene, for example 1-ethoxycarbonyl-2-propylidene), 2,6-dimethoxybenzoyl, 5,6,7,8-tetrahydronaphthoyl, 2-methoxy-1-naphthoyl, 2-ethoxy-1-naphthoyl, benzyloxycarbonyl, hexahydrobenzyloxycarbonyl, 5-methyl-3-phenyl-4-isoxazolylcarbonyl, 3-(2-chlorophenyl)-5-methyl-4-isoxazolylcarbonyl, 3-(2,6-dichlorophenyl)-5-methyl-4-isoxazolylcarbonyl, 2-chloroethylaminocarbonyl, acetyl, propionyl, butyryl, pivaloyl, hexanoyl, octanoyl, acrylyl, crotonyl, 3-butenoyl, 2-pentenoyl, methoxyacetyl, butylthioacetyl, allylthioacetyl, methylthioacetyl, chloroacetyl, bromoacetyl, dibromoacetyl, 3-chloropropionyl, 3-bromopropionyl, aminoacetyl or 5-amino-5-carboxy-valeryl (with an amino group which is optionally substituted, for example as indicated, such as substituted by a monoacyl or diacyl radical, for example an optionally halogenated lower alkanoyl radical, such as acetyl or dichloroacetyl, or phthaloyl, and/or with an optionally functionally modified carboxyl group, for example a carboxyl group present in the form of a salt, such as a sodium salt, or in the form of an ester, such as a lower alkyl ester, for example a methyl or ethyl ester, or an aryl-lower alkyl ester, for example diphenylmethyl ester), azidoacetyl, carboxyacetyl, methoxycarbonylacetyl, ethoxycarbonylacetyl, bis-methoxycarbonylacetyl, N-phenylcarbamoylacetyl, cyanoacetyl, α-cyanopropionyl, 2-cyano-3,3-dimethylacrylyl, phenylacetyl, α-bromophenylacetyl, α-azidophenylacetyl, 3-chlorophenylacetyl, 2- or 4-aminomethylphenyl-acetyl (with an amino group which is optionally substituted, for example, as indicated), phenacylcarbonyl, phenoxyacetyl, 4-trifluoromethylphenoxyacetyl, benzyloxyacetyl, phenylthioacetyl, bromophenylthioacetyl, 2-phenoxypropionyl, α-phenoxyphenylacetyl, α-methoxyphenylacetyl, α-ethoxyphenylacetyl, α-methoxy-3,4-dichlorophenylacetyl, α-cyano-phenylacetyl, especially phenylglycyl, 4-hydroxyphenylglycyl, 3-chloro-4-hydroxyphenylglycyl, 3,5-dichloro-4-hydroxy-phenylglycyl, α-aminomethyl-α-phenylacetyl or α-hydroxyphenylacetyl, (it being possible, in these radicals, for an amino group which is present to be optionally substituted, for example as indicated above, and/or an aliphatic and/or phenolically bonded hydroxyl group which is present to be optionally protected, analogously to the amino group, for example by a suitable acyl radical, especially by formyl or by an acyl radical of a carbonic acid half-ester), or α-O-methyl-phosphonophenylacetyl or α-,O,O-dimethyl-phosphono-phenylacetyl, also benzylthioacetyl, benzylthiopropionyl, α-carboxyphenylacetyl (with a carboxyl group which is optionally functionally modified, for example as indicated above), 3-phenylpropionyl, 3-(3-cyanophenyl)-propionyl, 4-(3-methoxyphenyl)-butyryl, 2-pyridylacetyl, 4-aminopyridiniumacetyl (optionally with an amino group which is substituted, for example as indicated above), 2-thienylacetyl, 3-thienylacetyl, 2-tetrahydrothienylacetyl, 2-furylacetyl, 1-imidazolylacetyl, 1-tetrazolylacetyl, α-carboxy-2-thienylacetyl or α-carboxy-3-thienylacetyl (optionally with a carboxyl group which is functionally modified, for example as indicated above), α-cyano-2-thienylacetyl, α-amino-α-(2-thienyl)-acetyl, α-amino-α-(2-furyl)-acetyl or α-amino-α-(4-isothiazolyl)-acetyl (optionally with an amino group which is substituted, for example as indicated above), α-sulphophenylacetyl (optionally with a sulpho group which is functionally modified, for example like the carboxyl group), 3-methyl-2-imidazolylthioacetyl, 1,2,4-triazol-3-ylthioacetyl, 1,3,4-triazol-2-ylthioacetyl, 5-methyl-1,2,4-thiadiazol-3-ylthioacetyl, 5-methyl-1,3,4-thiadiazol-2-ylthioacetyl or 1-methyl-5-tetrazolylthioacetyl.

An easily removable acyl radical Ac, especially of a carbonic acid half-ester, is above all an acyl radical of a half-ester of carbonic acid which can be split off by reduction, for example on treatment with a chemical reducing agent, or by treatment with acid, for example with trifluoroacetic acid, such as a lower alkoxycarbonyl group which preferably has multiple branching and/or an aromatic substituent on the carbon atom in the α-position to the oxy group, or a methoxycarbonyl group which is substituted by arylcarbonyl, especially benzoyl, radicals, or a lower alkoxycarbonyl radical which is substituted in the β-position by halogen atoms, for example tert.-butoxycarbonyl, tert.-pentoxycarbonyl, phenacyloxycarbonyl, 2,2,2-trichloroethoxycarbonyl or 2-iodoethoxycarbonyl or a radical which can be converted into the latter, such as 2-chloroethoxycarbonyl or 2-bromoethoxycarbonyl, and also preferably polycyclic cycloalkoxycarbonyl, for example adamantyloxycarbonyl, optionally substituted phenyl-lower alkoxycarbonyl, above all α-phenyl-lower alkoxycarbonyl, wherein the α-position is preferably polysubstituted, for example diphenylmethoxycarbonyl or α-4-biphenylyl-α-methylethoxycarbonyl, or furyl-lower alkoxycarbonyl, above all α-furyl-lower alkoxycarbonyl, for example furfuryloxycarbonyl.

A bivalent acyl group formed by the two radicals $R_1^A$ and $R_1^b$ is, for example, the acyl radical of a lower alkanedicarboxylic acid or lower alkenedicarboxylic acid, such as succinyl, or an o-arylenedicarboxylic acid, such as phthaloyl.

A further bivalent radical formed by the groups $R_1^A$ and $R_1^b$ is, for example, a 1-oxo-3-aza-1,4-butylene radical which is substituted, especially in the 2-position and contains, for example, optionally substituted phenyl or thienyl, and is optionally monosubstituted or disubstituted by lower alkyl, such as methyl, in the 4-position, for example 4,4-dimethyl-2-phenyl-1-oxo-3-aza-1,4-butylene.

An etherified hydroxyl group $R_2^A$ forms, together with the carbonyl grouping, an esterified carboxyl group which can preferably be split easily or can be converted easily into another functionally modified carboxyl group, such as into a carbamoyl or hydrazinocarbonyl group. Such a group $R_2^A$ is, for example, lower alkoxy, such as methoxy, ethoxy, n-propoxy or isopropoxy, which, together with the carbonyl grouping, forms an esterified carboxyl group, which can easily be converted, especially in 2-cephem compounds, into a free carboxyl group or into another functionally modified carboxyl group.

An etherified hydroxyl group $R_2^A$ which together with a —C(=O)— grouping forms an esterified carboxyl group which can be split particularly easily represents, for example, 2-halogeno-lower alkoxy, wherein halogen preferably has an atomic weight above 19. Such a radical forms, together with the —C(=O)— grouping, an esterified carboxyl group which can easily be split on treatment with chemical reducing agents under neutral or weakly acid conditions, for example with zinc in the presence of aqueous acetic acid, or an esterified carboxyl group which can easily be converted into such a group and is, for example, 2,2,2-trichloroethoxy or 2-iodoethoxy, also 2-chloroethoxy or 2-bromoethoxy, which can easily be converted into the latter.

An etherified hydroxyl group $R_2^A$ which together with the —C(=O)— grouping represents an esterified carboxyl group which can also be split easily on treatment with chemical reducing agents under neutral or weakly acid conditions, for example on treatment with zinc in the presence of aqueous acetic acid, and also on treatment with a suitable nucleophilic reagent, for example sodium thiophenolate, is an arylcarbonylmethoxy group, wherein aryl in particular represents an optionally substituted phenyl group, and preferably phenacyloxy.

The group $R_2^A$ can also represent an arylmethoxy group wherein aryl in particular denotes a monocyclic, preferably substituted, aromatic hydrocarbon radical. Such a radical forms, together with the —C(=O)— grouping, an esterified carboxyl group which can easily be split on irradiation, preferably with ultraviolet light, under neutral or acid conditions. An aryl radical in such an arylmethoxy group is in particular lower alkoxyphenyl, for example methoxyphenyl (wherein methoxy above all is in the 3-, 4- and/or 5-position) and/or above all nitrophenyl (wherein nitro is preferably in the 2-position). Such radicals are, in particular, lower alkoxy-benzyloxy, for example methoxy-benzyloxy, and/or nitrobenzyloxy, above all 3- or 4-methoxy-benzyloxy, 3,5-dimethoxybenzyloxy, 2-nitro-benzyloxy or 4,5-dimethoxy-2-nitro-benzyloxy.

An etherified hydroxyl group $R_2^A$ can also represent a radical which, together with the —C(=O)— grouping, forms an esterified carboxyl group which can easily be split under acid conditions, for example on treatment with trifluoroacetic acid or formic acid. Such a radical is above all a methoxy group in which methyl is polysubstituted by optionally substituted hydrocarbon radicals, especially aliphatic or aromatic hydrocarbon radicals, such as lower alkyl, for example methyl, and/or phenyl, or is monosubstituted by a carbocyclic aryl group possessing electron-donating substituents or by a heterocyclic group of aromatic character possessing oxygen or sulphur as a ring member, or in which methyl denotes a ring member in a polycycloaliphatic hydrocarbon radical or denotes the ring member which represents the α-position to the oxygen or sulphur atom in an oxacycloaliphatic or thiacycloaliphatic radical.

Preferred polysubstituted methoxy groups of this nature are tert.-lower alkoxy, for example tert.-butoxy or tert.-pentoxy, optionally substituted diphenylmethoxy, for example diphenylmethoxy or 4,4'-dimethoxydiphenylmethoxy, and also 2-(4-biphenylyl)-2-propoxy, whilst a methoxy group which contains the abovementioned substituted aryl group or the heterocyclic group is, for example, α-lower alkoxy-phenyllower alkoxy, such as 4-methoxybenzyloxy or 3,4-dimethoxybenzyloxy, or furfuryloxy, such as 2-furfuryloxy. A polycycloaliphatic hydrocarbon radical in which the methyl of the methoxy group represents a branched, preferably triply branched, ring member, is, for example, adamantyl, such as 1-adamantyl, and an abovementioned oxacycloaliphatic or thiacycloaliphatic radical wherein the methyl of the methoxy group is the ring member which represents the α-position to the oxygen atom or sulphur atom, denotes, for example, 2-oxa- or 2-thialower alkylene or -lower alkenylene with 5–7 ring atoms, such as 2-tetrahydrofuryl, 2-tetrahydropyranyl (sic) or 2,3-dihydro-2-pyranyl or corresponding sulphur analogues.

The radical $R_2^A$ can also represent an etherified hydroxyl group which, together with the —C(=O)— grouping forms an esterified carboxyl group which can be split hydrolytically, for example under weakly basic or weakly acid conditions. Such a radical is, preferably, an etherified hydroxyl group which forms an activated ester group with the —C(=O)— grouping, such as nitrophenyloxy, for example 4-nitrophenyloxy or 2,4-dinitrophenyloxy, nitrophenyl-lower alkoxy, for example 4-nitro-benzyloxy, hydroxy-lower alkylbenzyloxy, for example 4-hydroxy-3,5-tert.-butyl-benzyloxy, polyhalogenophenyloxy, for example 2,4,6-trichlorophenyloxy or 2,3,4,5,6-pentachlorophenyloxy, and also cyanomethoxy, as well as acylaminomethoxy, for example phthaliminomethoxy or succinyliminomethoxy.

The group $R_2^A$ can also represent an etherified hydroxyl group which, together with the carbonyl grouping of the formula —C(=O)—, forms an esterified carboxyl group which can be split under hydrogenolytic conditions and is, for example, α-phenyl-lower alkoxy, which is optionally substituted, for example by lower alkoxy or nitro, such as benzyloxy, 4-methoxybenzyloxy or 4-nitrobenzyloxy.

The group $R_2^A$ can also be an etherified hydroxyl group which, together with the carbonyl grouping —C(=O)—, forms an esterified carboxyl group which can be split under physiological conditions, above all an acyloxymethoxy group, wherein acyl denotes, for example, the radical of an organic carboxylic acid, above all of an optionally substituted lower alkanecarboxylic acid, or wherein acyloxymethyl forms the residue of a lactone. Hydroxyl groups etherified in this way are lower alkanoyloxymethoxy, for example acetoxymethoxy or pivaloyloxymethoxy, amino-lower alkanoyloxymethoxy, especially α-amino-lower alkanoyloxymethoxy, for example glycyloxymethoxy, L-valyloxymethoxy, L-leucyloxymethoxy and also phthalidyloxy.

A silyloxy or stannyloxy group $R_2^A$ preferably contains, as substituents, optionally substituted aliphatic, cycloaliphatic, aromatic or araliphatic hydrocarbon radicals, such as lower alkyl, halogeno-lower alkyl, cycloalkyl, phenyl or phenyl-lower alkyl groups, or optionally modified functional groups, such as etherified hydroxyl groups, for example lower alkoxy groups, or halogen atoms, for example chlorine atoms, and above all represents tri-lower alkylsilyloxy, for example trimethylsilyloxy, halogeno-lower alkoxy-lower alkylsilyl, for example chloromethoxymethylsilyl, or tri-lower alkylstannyloxy, for example tri-n-butylstannyloxy.

An acyloxy radical $R_2^d$ which, together with a —C(=O)— grouping, forms a mixed anhydride group which can be split, preferably hydrolytically, contains, for example, the acyl radical of one of the abovementioned organic carboxylic acids or carbonic acid half-derivatives and is, for example, lower alkanoyloxy which is optionally substituted, such as by halogen, for example fluorine or chlorine, preferably in the α-position, for example acetoxy, pivaloyloxy or trichloroacetoxy, or lower alkoxycarbonyloxy, for example methoxycarbonyloxy or ethoxycarbonyloxy.

A radical $R_2^d$ which, together with a —C(=O)— grouping, forms an optionally substituted carbamoyl or hydrazinocarbonyl group is, for example, amino, lower alkylamino or di-lower alkylamino, such as methylamino, ethylamino, dimethylamino or diethylamino, lower alkyleneamino, for example pyrrolidino or piperidino, oxa-lower alkyleneamino, for example morpholino, hydroxylamino, hydrazino, 2-lower alkylhydrazino or 2,2-di-lower alkylhydrazino, for example 2-methylhydrazino or 2,2-dimethylhydrazino.

An optionally substituted aliphatic hydrocarbon radical $R_3$ is, in particular, lower alkyl with up to 7, preferably with up to 4 carbon atoms, such as methyl, ethyl, n-propyl, isopropyl, n-butyl, isobutyl or sec.-butyl, and also lower alkenyl, for example allyl, tert.-amino-lower alkyl, wherein the tert.-amino group is separated from the oxygen atom by at least two carbon atoms, such as 2- or 3-di-lower alkylamino-lower alkyl, for example 2-dimethylaminoethyl, 2-diethylaminoethyl or 3-dimethylaminopropyl, or etherified hydroxy-lower alkyl, wherein the etherified hydroxyl group, especially lower alkoxy, is separated from the oxygen atom by at least two carbon atoms, such as 2- or 3-lower alkoxy-lower alkyl, for example 2-methoxyethyl or 2-ethoxyethyl. An optionally substituted araliphatic hydrocarbon radical $R_3$ is above all an optionally substituted phenyl-lower alkyl radical, especially a 1-phenyl-lower alkyl radical with 1–3 optionally substituted phenyl radicals, such as benzyl or diphenylmethyl, possible substituents being, for example, esterified or etherified hydroxyl, such as halogen, for example fluorine, chlorine or bromine, or lower alkoxy, such as methoxy.

The acyl radical $R_3$ of an aliphatic carboxylic acid is above all optionally substituted lower alkanoyl, for example acetyl, propionyl or pivaloyl, and such radicals can be substituted, for example by esterified or etherified hydroxyl, such as halogen, for example fluorine or chlorine, or lower alkoxy, for example methoxy or ethoxy. The acyl radical $R_3$ of an aromatic carboxylic acid is, for example, optionally substituted benzoyl, such as benzoyl or benzoyl substituted by esterified or etherified hydroxyl, for example halogen, such as fluorine or chlorine, or lower alkoxy, such as methoxy or ethoxy, or lower alkyl, for example methyl. The acyl radical $R_3$ of a carbonic acid half-derivative is, in particular, lower alkoxycarbonyl, such as methoxycarbonyl or ethoxycarbonyl.

Salts are, in particular, those of compounds of the formulae Ia and IB having an acid grouping, such as a carboxyl, sulpho or phosphono group, above all metal salts or ammonium salts, such as alkali metal salts and alkaline earth metal salts, for example sodium, potassium, magnesium or calcium salts, as well as ammonium salts with ammonia or suitable organic amines, possible amines for the salt formation being, above all, aliphatic, cycloaliphatic, cycloaliphatic-aliphatic and araliphatic primary, secondary or tertiary monoamines, diamines or polyamines, as well as heterocyclic bases, such as lower alkylamines, for example triethylamine, hydroxy-lower alkylamines, for example 2-hydroxyethylamine, bis-(2-hydroxyethyl)-amine or tri-(2-hydroxyethyl)-amine, basic aliphatic esters of carboxylic acids, for example 4-aminobenzoic acid 2-diethylaminoethyl ester, lower alkyleneamines, for example 1-ethyl-piperidine, cycloalkylamines, for example bicyclohexylamine, or benzylamines, for example N,N'-dibenzylethylenediamine, and also bases of the pyridine type, for example pyridine, collidine or quinoline. Compounds of the formulae IA and IB which possess a basic group can also form acid addition salts, for example with inorganic acids, such as hydrochloric acid, sulphuric acid or phosphoric acid, or with suitable organic carboxylic acids or sulphonic acids, for example trifluoroacetic acid or 4-methylphenylsulphonic acid. Compounds of the formulae IA and IB having an acid group and a basic group can also be in the form of internal salts, that is to say in the form of a zwitter-ion. 1-Oxides of compounds of the formula IA having salt-forming groups can also form salts, as described above.

The new compounds of the present invention possess valuable pharmacological properties or can be used as intermediate products for the manufacture of such compounds. Compounds of the formula IA wherein, for example, $R_1^a$ represents an acyl radical Ac occurring in pharmacologically active N-acyl derivatives of 6β-amino-penam-3-carboxylic acid compounds or 7β-amino-3-cephem-4-carboxylic acid compounds and $R_1^b$ represents hydrogen, or wherein $R_1^a$ and $R_1^b$ together represent a 1-oxo-3-aza-1,4-butylene radical which is preferably substituted in the 2-position, for example by an aromatic or heterocyclic radical, and preferably substituted in the 4-position, for example by 2 lower alkyl, such as methyl, $R_2$ denotes hydroxyl or an etherified hydroxyl group $R_2^d$ which, together with the carbonyl group, forms an esterified carboxyl group which can easily be split under physiological conditions, and $R_3$ has the abovementioned meaning, and functional groups which may be present in any acyl radical $R_1^a$, such as amino, carboxyl, hydroxyl and/or sulpho, are usually in the free form, or salts of such compounds having salt-forming groups, are effective, on parenteral and/or oral administration, against micro-organisms such as Gram-positive bacteria, for example *Staphylococcus aureus, Streptococcus pyogenes* and *Diplococcus pneumoniae* (for example in mice at doses of about 0.001 to about 0.02 g/kg s.c. or p.o.), and Gram-negative bacteria, for example, *Escherichia coli, Salmonella typhimurium, Shigella flexneri, Klebsiella pneumoniae, Enterobacter cloacae, Proteus vulgaris, Proteus rettgeri* and *Proteus mirabilis* (for example in mice in doses of about 0.001 to about 0.15 g/kg s.c. or p.o.), and especially also against penicillin-resistant bacteria, together with a low degree of toxicity. These compounds can therefore be used, for example in the form of antibiotically active preparations, for the treatment of corresponding infections.

Compounds of the formula IB or 1-oxides of compounds of the formula IA, wherein $R_1^a$, $R_1^b$, $R_2$ and $R_3$ have the meanings indicated in the context of the formula IA, or compounds of the formula IA, wherein $R_3$ has the abovementioned meaning, the radicals $R_1^a$ and $R_1^b$ represent hydrogen, or $R_1^a$ denotes an amino protective group different from an acyl radical occurring in pharmacologically active N-acyl derivatives of 6β-amino-penam-3-carboxylic acid compounds or 7β-amino-3-cephem-4-carboxylic acid compounds and $R_1^b$ denotes hydrogen, or $R_1^a$ and $R_1^b$ together represent a bivalent amino protective group different from a 1-oxo-3-aza-1,4-butylene radical which is preferably substituted in the 2-position, for example by an aromatic or heterocyclic radical, and preferably substituted in the 4-position, for example by 2 lower alkyl, such as methyl, and $R_2$ represents hydroxyl, or $R_1^a$ and $R_1^b$ have the abovementioned meanings, $R_2$ represents a radical $R_2^A$ which together with the —C(=O)— grouping forms a protected carboxyl group which can preferably be split easily, a carboxyl group protected in this way being different from a carboxyl group which can be split physiologically, and $R_3$ has the abovementioned meanings, are valuable intermediate products which can be converted in a simple manner, for example as is described below, into the abovementioned pharmacologically active compounds.

The invention in particular relates to the 3-cephem-compounds of the formula IA, wherein $R_1^a$ denotes hydrogen or preferably an acyl radical contained in a fermentatively obtainable (that is to say naturally occurring) or biosynthetically, semi-synthetically or total-synthetically obtainable, in particular pharmacologically active, such as highly active, N-acyl derivative of a 6β-amino-penam-3-carboxylic acid compound or 7β-amino-3-cephem-4-carboxylic acid compound, such as one of the abovementioned acyl radicals of the formula A, in which $R^I$, $R^{II}$, $R^{III}$ and n above all have the preferred meanings, $R_1^b$ represents hydrogen, or $R_1^a$ and $R_1^b$ together represent a 1-oxo-3-aza-1,4-butylene radical which is preferably substituted in the 2-position, for example by an aromatic or heterocyclic radical, such as phenyl, and preferably substituted in the 4-position, for example by two lower alkyl, such as methyl, $R_2$ represents hydroxyl, lower alkoxy which is optionally monosubstituted or polysubstituted, preferably in the α-position, for example by optionally substituted aryloxy, such as lower alkoxyphenyloxy, for example 4-methoxyphenyloxy, lower alkanoyloxy, for example acetoxy or pivaloyloxy, α-amino-lower alkanoyloxy, for example glycyloxy, L-valyloxy or L-leucyloxy, arylcarbonyl, for example benzoyl, or optionally substituted aryl, such as phenyl, lower alkoxyphenyl, for example 4-methoxyphenyl, nitrophenyl, for example 4-nitrophenyl, or biphenylyl, for example 4-biphenylyl, or is monosubstituted or polysubstituted in the β-position by halogen, for example chlorine, bromine or iodine, such as lower alkoxy, for example methoxy, ethoxy, n-propoxy, isopropoxy, b-butoxy, tert.-butoxy or tert.-pentoxy, bis-phenyloxy-methoxy, which is optionally substituted by lower alkoxy, for example bis-4-methoxyphenyloxy-methoxy, lower alkanoyloxy-methoxy, for example acetoxymethoxy or pivaloyloxymethoxy, α-amino-lower alkanoyloxy-methoxy, for example glycyloxymethoxy, phenacyloxy, optionally substituted phenyl-lower alkoxy, especially 1-phenyl-lower alkoxy, such as phenylmethoxy, with such radicals being able to contain 1–3 phenyl radicals which are optionally substituted, for example by lower alkoxy, such as methoxy, nitro or phenyl, for example benzyloxy, 4-methoxy-benzyloxy, 2-biphenylyl-2-propoxy, 4-nitro-benzyloxy, diphenylmethoxy, 4,4'-dimethoxydiphenylmethoxy or trityloxy, or 2-halogeno-lower alkoxy, for example 2,2,2-trichloroethoxy, 2-chloroethoxy, 2-bromoethoxy or 2-iodoethoxy, and also 2-phthalidyloxy, as well as acyloxy, such as lower alkoxycarbonyloxy, for example methoxycarbonyloxy or ethoxycarbonyloxy, or lower alkanoyloxy, for example acetoxy or pivaloyloxy, tri-lower alkylsilyloxy, for example trimethylsilyloxy, or amino or hydrazino which is optionally substituted, for example, by lower alkyl, such as methyl, or hydroxyl, for example amino, lower alkylamino or di-lower alkylamino, such as methylamino or dimethylamino, hydrazino, 2-lower alkylhydrazino or 2,2-di-lower alkylhydrazino, for example 2-methylhydrazino or 2,2-dimethylhydrazino, or hydroxyamino, and $R_3$ represents lower alkyl, for example methyl, ethyl, n-propyl, isopropyl or n-butyl, lower alkenyl, for example allyl, optionally substituted phenyl-lower alkyl, especially 1-phenyl-lower alkyl with 1 or 2 phenyl radicals which are optionally substituted, for example by lower alkoxy, such as methoxy, for example benzyl or diphenylmethyl, or lower alkanoyl, for example acetyl or propionyl, or lower alkoxycarbonyl, for example methoxycarbonyl, as well as benzoyl which is optionally substituted, for example by lower alkyl, such as methyl, lower alkoxy, for example methoxy, or halogen, for example fluorine or chlorine, as well as the 1-oxides thereof, and also the corresponding 2-cephem compounds of the formula IB, or salts of such compounds with salt-forming groups.

Above all, in a 3-cephem compound of the formula IA, and in a corresponding 2-cephem compound of the formula IB, and also in a 1-oxide of a 3-cephem compound of the formula IA, or in a salt of such a compound having salt-forming groups, $R_1^a$ represents hydrogen or an acyl radical contained in fermentatively obtainable (that is to say naturally occurring) or biosynthetically obtainable N-acyl derivatives of 6β-amino-penam-3-carboxylic acid compounds or 7β-amino-3-cephem-4-carboxylic acid compounds, especially of the formula A, wherein $R^I$, $R^{II}$ and $R^{III}$ and n above all have the preferred meanings, such as a phenylacetyl or phenyloxyacetyl radical which is optionally substituted, for example by hydroxyl, also a lower alkanoyl or lower alkenoyl radical which is optionally substituted, for example by lower alkylthio, or lower alkenylthio, as well as by optionally substituted, such as acylated, amino and/or functionally modified, such as esterified, carboxyl, for example 4-hydroxy-phenylacetyl, hexanoyl, octanoyl or n-butylthioacetyl, and especially 5-amino-5-carboxy-valeryl, wherein the amino and/or the carboxyl groups are optionally protected and are present, for example, as acylamino or esterified carboxyl, phenylacetyl or phenyloxyacetyl, or an acyl radical occurring in highly active N-acyl derivatives of 6β-amino-penam-3-carboxylic acid compounds or 7β-amino-3-cephem-4-carboxylic acid compounds, especially of the formula A, wherein $R^I$, $R^{II}$, $R^{III}$ and n above all have the preferred meanings, such as formyl, 2-halogenoethylcarbamoyl, for example 2-chloroethylcarbamoyl, cyanoacetyl, phenylacetyl, thienylacetyl, for example 2-thienylacetyl, or tetrazolylacetyl, for example 1-tetrazolylacetyl, but especially acetyl substituted in the α-position by a cyclic, such as a cycloaliphatic, aromatic or heterocyclic, above all monocyclic, radical and by a functional group, above all amino, carboxyl, sulpho or hydroxyl groups, especially phenylglycyl, wherein phenyl represents phenyl which is optionally substituted, for example by optionally protected hydroxyl, such as acyloxy, for example optionally halogen-substituted lower alkoxycarbonyloxy or lower alkanoyloxy, and/or by halogen, for example chlorine, for example phenyl or 3- or 4-hydroxyphenyl, 3-chloro-4-hydroxyphenyl or 3,5-dichloro-4-hydroxyphenyl (optionally also with a protected hydroxyl group, such as an acylated hydroxyl group), and wherein the amino group can also optionally be substituted and represents, for example, a sulphoamino group optionally present in the form of a salt, or an amino group which contains, as substituents, a hydrolytically removable trityl group or above all an acyl group, such as an optionally substituted carbamoyl group, such as an optionally substituted ureidocarbonyl group, for example ureidocarbonyl or N'-trichloromethylureidocarbonyl, or an optionally substituted guanidinocarbonyl group, for example guanidinocarbonyl, or an acyl radical which can be split off, preferably easily, for example on treatment with an acid agent, such as trifluoroacetic acid, or reductively, such as on treatment with a chemical reducing agent, such as zinc in the presence of aqueous acetic acid, or with catalytic hydrogen, or hydrolytically, or an acyl radical which can be converted into such a radical, preferably a suitable acyl radical of a carbonic acid half-ester, such as one of the abovementioned, for example optionally halogen-substituted or benzoyl-substituted, lower alkoxycarbonyl radicals, for example tert.-butoxycarbonyl, 2,2,2-trichloroethoxycarbonyl, 2-chloroethoxycarbonyl, 2-bromoethoxycarbonyl, 2-iodoethoxycarbonyl or phenacyloxycarbonyl, optionally lower alkoxy-substituted or nitro-substituted phenyl-lower alkoxycarbonyl, for example 4-methoxybenzyloxycarbonyl or diphenylmethoxycarbonyl, or a suitable acyl radical of a carbonic acid half-amide, such as carbamoyl or N-methylcarbamoyl, or an arylthio or aryl-lower alkylthio radical which can be split off with a nucleophilic reagent, such as hydrocyanic acid, sulphurous acid or thioacetic acid amide, for example 2-nitrophenylthio or tritylthio, an arylsulphonyl radical which can be split off by means of electrolytic reduction, for example 4-methylphenylsulphonyl, or a 1-lower alkoxycarbonyl or 1-lower alkanoyl-2-propylidene radical which can be split off with an acid agent, such as formic acid or aqueous mineral acid, for example hydrochloric acid or phosphoric acid, for example 1-ethoxycarbonyl-2-propylidene, and also α-thienyl-glycyl, such as α-2- or α-3-thienylglycyl, α-furylglycyl, such as α-2-furylglycyl, α-isothiazolylglycyl, such as α-4-isothiazolyl-glycyl, it being possible for the amino group in such radicals to be substituted or protected, for example as indicated for a phenylglycyl radical, also α-carboxy-phenylacetyl or α-carboxy-thienylacetyl, for example α-carboxy-2-thienylacetyl (optionally with a functionally modified carboxyl group, for example a carboxyl group present in the form of a salt, such as a sodium salt, or in the form of an ester, such as a lower alkyl ester, for example methyl or ethyl ester, or phenyl-lower alkyl ester, for example diphenylmethyl ester), α-sulpho-phenylacetyl (optionally also with a sulpho group which is functionally modified, for example like the carboxyl group), α-phosphono-, α-O-methylphosphono- or α-O,O'-dimethyl-phosphono-phenylacetyl, or α-hydroxy-phenylacetyl (optionally with a functionally modified hydroxyl group, especially with an acyloxy group, wherein acyl denotes an acyl radical which can be split off, preferably easily, for example on treatment with an acid agent, such as trifluoroacetic acid, or with a chemical reducing agent, such as zinc in the presence of aqueous acetic acid, or an acyl radical which can be converted into such a radical, preferably a suitable acyl radical of a carbonic acid half-ester, such as one of the abovementioned lower alkoxycarbonyl radicals which are, for example, optionally substituted by halogen or benzoyl, for example 2,2,2-trichloroethoxycarbonyl, 2-chloroethoxycarbonyl, 2-bromoethoxycarbonyl, 2-iodoethoxycarbonyl, tert.-butoxycarbonyl or phenacyloxycarbonyl, and also formyl), as well as 1-amino-cyclohexylcarbonyl, aminomethylphenylacetyl, such as 2- or 4-aminomethylphenylacetyl, or amino-pyridiniumacetyl, for example 4-amino-pyridiniumacetyl (optionally also with an amino group which is substituted, for example as indicated above), or pyridylthioacetyl, for example 4-pyridylthioacetyl, and $R_1{}^b$ represents hydrogen, or $R_1{}^a$ and $R_1{}^b$ together represent a 1-oxo-3-aza-1,4-butylene radical which is preferably substituted in the 2-position by phenyl which is optionally substituted by protected hydroxyl, such as acyloxy, for example optionally halogen-substituted lower alkoxycarbonyloxy or lower alkanoyloxy, and/or by halogen, for example chlorine, for example phenyl or 3- or 4-hydroxyphenyl, 3-chloro-4-hydroxyphenyl or 3,5-dichloro-4-hydroxyphenyl (optionally also with a hydroxyl group which is protected, for example acylated as indicated above), and which optionally contains two lower alkyl, such as methyl, in the 4-position, and $R_2$ represents hydroxyl, lower alkoxy, especially α-poly-branched lower alkoxy, for example tert.-butoxy, also methoxy or ethoxy, 2-halogeno-lower alkoxy, for example 2,2,2-trichloroethoxy, 2-iodoethoxy or 2-chloroethoxy or 2-bromoethoxy which can easily be converted into 2-iodoethoxy, phenacyloxy, 1-phenyl-lower alkoxy with 1–3 phenyl radicals which are optionally substituted by lower alkoxy or nitro, for example 4-methoxybenzyloxy, 4-nitrobenzyloxy, diphenylmethoxy, 4,4'-dimethoxy-diphenylmethoxy or trityloxy, lower alkanoyloxymethoxy, for example acetoxymethoxy or pivaloyloxymethoxy, α-amino-lower alkanoyloxymethoxy, for example glycyloxymethoxy, 2-phthalidyloxymethoxy, lower alkoxycarbonyloxy, for example ethoxycarbonyloxy, or lower alkanoyloxy, for example acetoxy, and also tri-lower alkylsilyloxy, for example trimethylsilyloxy, and $R_3$ above all represents lower alkyl, for example methyl, ethyl or n-butyl, also lower alkenyl, for example allyl, and 1-phenyl-lower alkyl, for example benzyl or diphenylmethyl, but also lower alkanoyl, for example acetyl or propionyl, lower alkoxycarbonyl, for example methoxycarbonyl, or benzoyl.

The invention above all relates to 3-cephem compounds of the formula IA, wherein $R_1{}^a$ denotes hydrogen or an acyl group of the formula

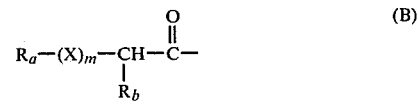

(B)

wherein $R_a$ denotes phenyl or hydroxyphenyl, for example 3- or 4-hydroxyphenyl, also hydroxy-chlorophenyl, for example 3-chloro-4-hydroxyphenyl or 3,5-dichloro-4-hydroxy-phenyl, it being possible for hydroxy substituents in such radicals to be protected by acyl radicals, such as optionally halogenated lower alkoxycarbonyl radicals, for example tert.-butoxycarbonyl or 2,2,2-trichloroethoxycarbonyl, as well as thienyl, for example 2- or 3-thienyl, and also pyridyl, for example 4-pyridyl, aminopyridinium, for example 4- aminopyridinium, furyl, for example 2-furyl, isothiazolyl, for example 4-isothiazolyl, or tetrazolyl, for example 1-tetrazolyl, X represents oxygen or sulphur, m represents 0 or 1 and $R_b$ represents hydrogen, or, if m represents O, $R_b$ represents amino, as well as protected amino, such as acylamino, for example α-poly-branched lower alkoxycarbonylamino, such as tert.-butoxycarbonylamino, or 2-halogeno-lower alkoxycarbonylamino, for example 2,2,2-trichloroethoxycarbonylamino, 2-iodoethoxycarbonylamino or 2-bromoethoxycarbonylamino, or optionally lower alkoxy-substituted or nitro-substituted phenyl-lower alkoxycarbonylamino, for example 4-methoxybenzyloxycarbonylamino or diphenylmethoxycarbonylamino, or 3-guanylureido, also sulphoamino or tritylamino, as well as arylthioamino, for example 2-nitrophenylthioamino, arylsulphonylamino, for example 4-methylphenylsulphonylamino, or 1-lower alkoxycarbonyl-2-propylideneamino, for example 1-ethoxycarbonyl-2-propylideneamino, carboxyl, or carboxyl present in the form of a salt, for example an alkali metal salt, such as a sodium salt, as well as protected carboxyl, for example esterified carboxyl, such as phenyl-lower alkoxycarbonyl, for example diphenylmethoxycarbonyl, sulpho, or sulpho present in the form of a salt, for example an alkali metal salt, such as a sodium salt, as well as protected sulpho, hydroxyl, as well as protected hydroxyl, such as acyloxy, for example α-poly-branched lower alkoxycarbonyloxy, such as tert.-butoxycarbonyloxy, 2-halogeno-lower alkoxycarbonyloxy, such as 2,2,2-trichloroethoxycarbonyloxy, 2-iodoethoxycarbonyloxy or 2-bromoethoxycarbonyloxy, also formyloxy, or O-lower alkylphosphono or O,O'-di-lower alkylphosphono, for example O-methyl-phosphono or O,O'-dimethylphosphono, or denotes a 5-amino-5-carboxy-valeryl radical, wherein the amino and/or carboxyl groups can also be protected and are, for example, present as acylamino, for example lower alkanoylamino, such as acetylamino, halogeno-lower alkanoylamino such as dichloroacetylamino, benzoylamino or phthaloylamino, or as esterified carboxyl, such as phenyl-lower alkoxycarbonyl, for example diphenylmethoxycarbonyl, whereby advantageously m is 1, when $R_a$ represents phenyl, hydroxy-phenyl, hydroxy-chlorophenyl or pyridyl, and m is 0 and $R_b$ is different from hydrogen, when $R_a$ is phenyl, hydroxy-phenyl, hydroxy-chlorophenyl, thienyl, furyl or isothiazolyl, whereby $R_a$ can also be 1,4-cyclohexadienyl, if m represents 0 and $R_b$ is carboxyl, or carboxyl present in the form of a salt, for example an alkali metal salt, such as a sodium salt, as well as protected carboxyl, for example esterified carboxyl, such as phenyl-lower alkoxycarbonyl, for example diphenylmethoxycarbonyl, sulpho, or sulpho present in the form of a salt, for example an alkali metal salt, such as a sodium salt, as well as protected sulpho, hydroxyl, as well as protected hydroxyl, such as acyloxy, for example α-poly-branched lower alkoxycarbonyloxy, such as tert.-butoxycarbonyloxy, 2-halogeno-lower alkoxycarbonyloxy, such as 2,2,2-trichloroethoxycarbonyloxy, 2-iodoethoxycarbonyloxy or 2-bromoethoxycarbonyloxy, also formyloxy, or O-lower alkylphosphono or O,O'-di-lower alkylphosphono, for example O-methyl-phosphono or O,O'-dimethylphosphono, $R_1^b$ denotes hydrogen, $R_2$ above all represents hydroxyl and also represents lower alkoxy, especially α-poly-branched lower alkoxy, for example tert.-butoxy, 2-halogeno-lower alkoxy, for example 2,2,2-trichloroethoxy, 2-iodoethoxy or 2-bromoethoxy, or diphenylmethoxy which is optionally substituted, for example, by lower alkoxy, for example methoxy, for example diphenylmethoxy or 4,4'-dimethoxydiphenylmethoxy, as well as tri-lower alkylsilyloxy, for example trimethylsilyloxy, and $R_3$ denotes lower alkyl, for example methyl, ethyl or n-butyl, as well as lower alkenyl, for example allyl, or phenyl-lower alkyl, for example benzyl, also lower alkanoyl, for example acetyl or propionyl, or lower alkoxycarbonyl, for example methoxycarbonyl, as well as the 1-oxides of such 3-cephem compounds of the formula IA, and also the corresponding 2-cephem compounds of the formula IB, or salts, especially pharmaceutically usable, non-toxic salts, of such compounds having salt-forming groups, such as alkali metal salts, for example sodium salts, or alkaline earth metal salts, for example calcium salts, or ammonium salts, including those with amines, of compounds wherein $R_2$ represents hydroxy, or internal salts of compounds wherein $R_2$ represents hydroxx and which contain a free amino group in the acyl radical of the formula B.

Above all, in 3-cephem compounds of the formula IA, and also in corresponding 2-cephem compounds of the formula IB, as well as in salts, especially in pharmaceutically usable non-toxic salts, of such compounds which have salt-forming groups, as in the salts mentioned in the preceding paragraph, $R_1^a$ represents hydrogen, the acyl radical of the formula B, wherein $R_a$ denotes phenyl, as well as hydroxy-phenyl, e.g. 4-hydroxy-phenyl, thienyl, e.g. 2-thienyl or 4-isothiazolyl, X denotes oxygen, m denotes 0 or 1 and $R_b$ denotes hydrogen, or, if m represents 0, denotes amino, as well as protected amino, such as acylamino, for example α-poly-branched lower alkoxycarbonylamino, such as tert.-butoxycarbonylamino, or 2-halogeno-lower alkoxycarbonylamino, for example 2,2,2-trichloroethoxycarbonylamino, 2-iodoethoxycarbonylamino or 2-bromoethoxycarbonylamino, or optionally lower alkoxy-substituted or nitro-substituted phenyl-lower alkoxycarbonylamino, for example 4-methoxybenzyloxycarbonylamino, or hydroxyl, such as protected hydroxyl, such as acyloxy, for example α-poly-branched lower alkoxycarbonyloxy, such as tert.-butoxycarbonyloxy, or 2-halogeno-lower alkoxycarbonyloxy, such as 2,2,2-trichloroethoxycarbonyloxy, 2-iodoethoxycarbonyloxy or 2-bromoethoxycarbonyloxy, and also formyloxy, or represents a 5-amino-5-carboxy-valeryl radical, wherein the amino and carboxyl group can also be protected and, for example, are in the form of acylamino, for example lower alkanoylamino, such as acetylamino, halogeno-lower alkanoylamino, such as dichloroacetylamino, benzoylamino or phthaloylamino, or of esterified carboxyl, such as phenyl-lower alkoxycarbonyl, for example diphenylmethoxycarbonyl, whereby advantageously m represents 1, when $R_a$ is phenyl or hydroxyphenyl, whereby $R_a$ can also be 1,4-cyclohexadienyl, if m represents 0 and $R_b$ is hydroxyl or protected hydroxyl, such as acyloxy, for example α-poly-branched lower alkoxycarbonyloxy, such as tert.-butoxycarbonyloxy, or 2-halogeno-lower alkoxycarbonyloxy, such as 2,2,2-trichloroethoxycarbonyloxy, 2-iodoethoxycarbonyloxy or bromoethoxycarbonyloxy, and also formyloxy, $R_1^b$ represents hydrogen, $R_2$ above all denotes hydroxyl and also lower alkoxy which is optionally halogen-substituted, for example chlorine-substituted, bromine-substituted or iodine-substituted, in the 2-position, especially α-poly-branched lower alkoxy, for example tert.-butoxy, or 2-halogeno-lower alkoxy, for example 2,2,2-trichloroethoxy, 2-iodoethoxy or 2-bromoethoxy, or optionally lower alkoxy-substituted, such as methoxy-substituted, diphenylmethoxy, for example diphenylmethoxy or 4,4'-dimethoxy-diphenylmethoxy, and also tri-lower alkylsilyloxy, for example trimethylsilyloxy, and $R_3$ denotes lower alkyl, for example methyl, ethyl or n-butyl, as well as lower alkenyl, for example allyl, or phenyl-lower alkyl, for example benzyl.

The invention above all relates to 7β-(D-α-amino-α-$R_a$-acetylamino)-3-lower alkoxy-3-cephem-4-carboxylic acids, wherein $R_a$ represents phenyl, 4-hydroxyphenyl, or 2-thienyl, and lower alkoxy contains up to 4 carbon atoms and represents, for example, ethoxy or n-butoxy, but above all methoxy, and the internal salts thereof, and above all 3-methoxy-7β-(D-α-phenylglycylamino)-3-cephem-4-carboxylic acid and the internal salt thereof; in the abovementioned concentrations, especially on oral administration, these compounds display excellent antibiotic properties both against Gram-positive and especially against Gram-negative bacteria, with a low order of toxicity.

The compounds of the formulae IA and IB are obtained by converting a cepham-3-one compound of the formula

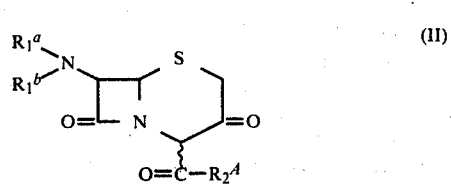

or a corresponding enol having a double bond in the 2,3- or 3,4-position, or a 1-oxide of such a compound, into an enol derivative having a functionally modified hydroxyl group of the formula -O-$R_3$ in the 3-position and, if desired, in a resulting compound of the formula IA or IB, converting the protected carboxyl group of the formula —C(=O)—$R_2^A$ into the free carboxyl group or into another protected carboxyl group and/or, if desired, within the definition of the products a resulting compound is converted into another compound and/or if desired, converting a resulting compound having a salt-forming group into a salt or a resulting salt into the free compound or into another salt and/or, if desired, separating a resulting mixture of isomeric compounds into the individual isomers.

In a starting material of the formula II, $R_2^A$ preferably represents an etherified hydroxyl group $R_2^A$ which, with the —C(=O)— grouping, forms an esterified carboxyl group which can be split, especially under mild conditions, it being possible for functional groups which may be present in a carboxyl protective group $R_2^A$ to be protected in a manner which is in itself known, for example as indicated above. A group $R_2^A$ is, for example, in particular an optionally halogen-substituted lower alkoxy group, such as α-poly-branched lower alkoxy, for example tert.-butoxy, or 2-halogeno-lower alkoxy, wherein halogen represents, for example, chlorine, bromine or iodine, above all 2,2,2-trichloroethoxy, 2-bromoethoxy, or 2-iodoethoxy, or an optionally substituted 1-phenyl-lower alkoxy group, such as a 1-phenyl-lower alkoxy group which contains lower alkoxy, for example methoxy, or nitro, such as benzyloxy or diphenylmethoxy which are optionally substituted, for example as indicated, for example benzyl, 4-methoxybenzyl, 4-nitrobenzyl, diphenylmethoxy or 4,4'-dimethoxy-diphenylmethoxy, and also an organic silyloxy or stannyloxy group, such as tri-lower alkylsilyloxy, for example trimethylsilyloxy. Preferably, in a starting material of the formula II, the radical $R_1^a$ denotes an amino protective group $R_1^A$, such as an acyl group Ac, in which free functional groups which may be present, for example amino, hydroxyl, carboxyl or phosphono groups, can be protected in a manner which is in itself known, amino groups, for example, by the abovementioned acyl, trityl, silyl or stannyl radicals as well as substituted thio or sulphonyl radicals, and hydroxyl, carboxyl or phosphono groups, for example, by the abovementioned ether or ester groups, including silyl or stannyl groups, and $R_1^b$ denotes hydrogen.

Cepham-3-one starting substances of the formula II can be in the keto form and/or in the enol form, with the ring double bond in the 2,3- or 3,4-position. Usually, the starting substances of the formula II are converted from the enol form into the enol derivatives of the formulae IA and IB. Furthermore it is also possible, for example, to employ a mixture of a compound of the formula II and of the corresponding 1-oxide as the starting material and to obtain, as the product, the mixture of compounds of the formulae IA and IB and of the 1-oxide of a compound of the formula IA. It is possible to employ a starting material in the pure form or in the form of the crude reaction mixture obtainable in its manufacture.

The conversion of the starting substances of the formula II into the enol derivatives can be carried out in a manner which is in itself known.

Enol-ethers, that is to say compounds of the fomrula IA and/or IB, wherein $R_3$ represents an optionally substituted hydrocarbon radical, are obtained according to any process suitable for the etherification of enol groups, it being possible to use starting substances of the formula II wherein $R_1^a$ and $R_1^b$ represent hydrogen but wherein preferably $R_1^a$ represents an amino protective group $R_1^A$. Preferably, the etherifying reagent used is a diazo compound of the formula $R_3-N_2$ (III) corresponding to the optionally substituted hydrocarbon radical $R_3$, above all an optionally substituted diazo-lower alkane, for example diazo-methane, diazoethane or diazo-n-butane, and also an optionally substituted phenyl-diazo-lower alkane such as 1-phenyl-diazo-lower alkane, for example phenyldiazomethane or diphenyldiazomethane. These reagents are used in the presence of a suitable inert solvent, such as an aliphatic, cycloaliphatic or aromatic hydrocarbon, such as hexane, cyclohexane, benzene or toluene, of a halogenated aliphatic hydrocarbon, for example methylene chloride, of a lower alkanol, for example methanol, ethanol or tert.-butanol, or of an ether, such as of a di-lower alkyl-ether, for example diethyl ether, or of a cyclic ether, for example tetrahydrofurane or dioxane, or of a solvent mixture and, depending on the diazo reagent, with cooling, at room temperature or with slight warming and also, if necessary, in a closed vessel and/or under an inert gas atmosphere, for example a nitrogen atmosphere.

Furthermore, enol-ethers of the formula IA and/or IB can be formed by treatment with a reactive ester of an alcohol of the formula $R_3$-OH (IV) which corresponds to the optionally substituted hydrocarbon radical $R_3$. Suitable esters are above all those with strong inorganic or organic acids, such as mineral acids, for example hydrogen halide acids, such as hydrochloric acid, hydrobromic acid or hydriodic acid, also sulphuric acid or halogeno-sulphuric acids, for example fluorosulphuric acid, or strong organic sulphonic acids, such as lower alkanesulphonic acids which are optionally substituted, for example by halogen, such as fluorine, or aromatic sulphonic acids, such as, for example, benzenesulphonic acids which are optionally substituted, for example by lower alkyl, such as methyl, halogen, such as bromine, and/or nitro, for example methanesulphonic acid, trifluoromethanesulphonic acid or p-toluenesulphonic acid. These reagents, especially di-lower alkyl sulphates, such as dimethyl sulphate, and also lower alkyl fluorosulphonates, for example methyl fluorosulphate, or optionally halogen-substituted methanesulphonic acid lower alkyl esters, for example trifluoromethanesulphonic acid methyl ester, are usually employed in the presence of a solvent, such as of an optionally halogenated, such as chlorinated, aliphatic, cycloaliphatic or aromatic hydrocarbon, for example methylene chloride, of an ether, such as dioxane or tetrahydrofurane, or of a lower alkanol, such as methanol, or of a mixture. At the same time, suitable condensation agents are preferably employed, such as alkali metal carbonates or bicarbonates, for example sodium or potassium carbonate or bicarbonate, (usually together with a sulphate) or organic bases such as, usually sterically hindered, tri-lower alkylamines, for example N,N-diisopropyl-N-ethyl-amine (preferably together with lower alkyl halogenosulphates or optionally halogen-substituted methanesulphonic acid lower alkyl esters), the reaction being carried out with cooling, at room temperature or with warming, for example at temperatures of about −20° C. to about 50° C. and, if necessary, in a closed vessel and/or in an inert gas atmosphere, for example a nitrogen atmosphere.

Enol-ethers can also be manufactured by treatment with a compound containing two or three etherified hydroxyl groups of the formula $R_3$—O—(V) on the same carbon atom of aliphatic character, that is to say by treatment with an appropriate acetal or ortho-ester, in the presence of an acid agent. Thus, for example, it is possible to use, as etherifying agents, gem-lower alkoxy-lower alkanes, such as 2,2-dimethoxy-propane, in the presence of a strong organic sulphonic acid, such as p-toluenesulphonic acid, and of a suitable solvent, such as of a lower alkanol, for example methanol, or of a di-lower alkylsulphoxide or lower alkylenesulphoxide, for example dimethylsulphoxide, or orthoformic acid tri-lower alkyl esters, for example orthoformic acid triethyl ester, in the presence of a strong mineral acid, for example sulphuric acid or of a strong organic sulphonic acid, such as p-toluenesulphonic acid, and of a suitable solvent, such as of a lower alkanol, for example ethanol, or of an ether, for example dioxane, and thus to arrive at compounds of the formula IA and/or IB, wherein $R_3$ represents lower alkyl, for example methyl or ethyl.

The enol ethers of the formula IA and/or IB can also be obtained if starting substances of the formula II are treated with tri-$R_3$-oxonium salts of the formula $(R_3)_3O^{\oplus}A^{\ominus}$ (VI) (so-called Meerwein salts), as well as di-$R_3O$-carbenium salts of the formula $(R_3O)_2CH^{\oplus}A^{\ominus}$ (VII) or di-$R_3$-halonium salts of the formula $(R_3)_2Hal^{\oplus}A^{\ominus}$ (VIII), wherein $A^{\ominus}$ denotes the anion of an acid and $Hal^{\oplus}$ denotes a halonium ion, especially a bromonium ion. The salts concerned are above all tri-lower alkyloxonium salts, as well as di-lower alkoxycarbenium salts or di-lower alkylhalonium salts, especially the appropriate salts with complex acids containing fluorine, such as the appropriate tetrafluoborates, hexafluophosphates, hexafluoantimonates or hexachloroantimonates. Such reagents are, for example, trimethyloxonium or triethyloxonium hexafluoantimonate, hexachloroantimonate, hexafluophosphate or tetrafluoborate, dimethoxycarbenium hexafluophosphate or dimethylbromonium hexafluoantimonate. These etherifying agents are preferably used in an inert solvent, such as an ether or a halogenated hydrocarbon, for example diethyl ether, tetrahydrofurane or methylene chloride, or in a mixture thereof, if necessary in the presence of a base, such as of an organic base, for example of a preferably sterically hindered tri-lower alkylamine, for example N,N-diisopropyl-N-ethyl-amine, and with cooling, at room temperature or with slight warming, for example at about −20° C. to about 50° C., if necessary in a closed vessel and/or in an inert gas atmosphere, for example a nitrogen atmosphere.

The enol-ethers of the formulae IA and/or IB can also be manufactured by treating starting substances of the formula II with a 3-substituted 1-$R_3$-triazene compound (IX) (that is to say a compound of the formula Subst.—N=N—NH—$R_3$), the substituent of the 3-nitrogen atom denoting an organic radical bonded via a carbon atom, preferably a carbocyclic aryl radical, such as an optionally substituted phenyl radical, for example lower alkylphenyl, such as 4-methyl-phenyl. Such triazene compounds are 3-aryl-1-lower alkyl-triazenes, for example 3-(4-methylphenyl)-1-methyl-triazene, 3-(4-methyl-phenyl)-1-ethyl-triazene, 3-(4-methylphenyl)-1-n-propyl-triazene or 3-(4-methylphenyl)-1-isopropyl-triazene, 3-aryl-1-lower alkenyl-triazenes, for example 3-(4-methylphenyl)-allyl-triazene, or 3-aryl-1-phenyl-lower alkyl-triazenes, for example 3-(4-methylphenyl)-1-benzyl-triazene. These reagents are usually employed in the presence of inert solvents, such as optionally halogenated hydrocarbons or ethers, for example benzene, or solvent mixtures, and with cooling, at room temperature or preferably at elevated temperature, for example at about 20° C. to about 100° C., if necessary in a closed vessel and/or in an inert gas atmosphere, for example a nitrogen atmosphere.

Enol-esters, that is to say compounds of the formula IA and/or IB, wherein $R_3$ represents an acyl group, are obtained according to any process suitable for the esterification of enol groups, with at least one of the groups $R_1^a$ and $R_1^b$ in the starting material of the formula II being different from hydrogen, if simultaneous acylation of a free amino group is to be avoided. Thus, preferably carboxylic acids corresponding to the acyl radical, of the formula $R_3$-OH (X) or reactive acid derivatives thereof are used, especially corresponding anhydrides (by which there are also to be understood the internal anhydrides of carboxylic acids, that is to say ketenes, or of carbamic or thiocarbamic acids, that is to say isocyanates or isothiocyanates, or mixed anhydrides, such as those which can be formed, for example, with hydrogen halide acids, such as hydrofluoric acid or hydrochloric acid, with hydrocyanic acid, with halogenoformic acid lower alkyl esters, such as chloroformic acid ethyl esters or isobutyl esters, or with trichloroacetic acid chloride, that is to say the corresponding halides, for example fluorides or chlorides, also pseudohalides, such as cyanocarbonyl compounds corresponding to the carboxylic acids, as well as lower alkoxycarbonyloxycarbonyl, for example ethoxycarbonyloxycarbonyloxy or isobutoxycarbonyloxycarbonyl compounds), or activated esters, such as esters with vinylogous alcohols (that is to say enols), for example esters of lower alkanecarboxylic acids with vinylogous alkanols, for example acetic acid isopropenyl ester, the reaction being carried out, if necessary, in the presence of suitable condensation agents, when using acids, for example, in the presence of carbodiimides compounds, such as dicyclohexylcarbodiimides, or carbonyl compounds such as diimidazolylcarbonyl and when using reacting acid derivatives, for example, in the presence of basic agents, such as tri-lower alkylamines, for example triethylamine, or heterocyclic bases, for example pyridine, and when using esters with vinylogous alcohols in the presence of an acid agent, such as a mineral acid, for example sulphuric acid, or a strong sulphonic acid, for example p-toluenesulphonic acid. The acylation reaction can be carried out in the absence or in the presence of a solvent or solvent mixture, with cooling, at room temperature or with warming and, if necessary, in a closed vessel and/or in an inert gas atmosphere, for example a nitrogen atmosphere. Suitable solvents are, for example, optionally substituted, especially chlorinated, aliphatic, cycloaliphatic, or aromatic hydrocarbons such as benzene or toluene, it also being possible to use suitable esterification reagents, such as acetic anhydride, as diluents.

In the above etherification or esterification reaction, it is possible to obtain single compounds of the formulae IA or IB or mixtures thereof, depending on the starting material and reaction conditions. Thus, mixtures are obtained, for example, on using starting material of the formula II which is contaminated, for example by heavy metal compounds, such as chromium-II compounds, or, if the starting material of the formula II is not isolated during its manufacture from compounds of the formula XII, or using correspondingly contaminated compounds of the formula XII or on carrying out the reaction under basic conditions; an increasing proportion of compounds of the formula IB is obtained. Mixtures obtained can be separated in a manner which is in itself known, for example with the aid of suitable methods of separation, for example by adsorption and fractional elution, including chromatography (column chromatography, paper chromatography or plate chromatography) using suitable adsorbents, such as silica gel or aluminium oxide, and eluting agents, and also by fractional crystallisation, solvent partitioning and the like.

In the process according to the invention, and in additional measures which may require to be carried out it is possible, if necessary, transiently to protect free functional groups, which do not participate in the reaction, in the starting substances, or in the compounds obtainable according to the process, for example free amino groups by, for example, acylation, tritylation or silylation, free hydroxyl or mercapto groups by, for example, etherification or esterification, and free carboxyl groups by, for example, esterification, including silylation and in each case to liberate them after the reaction has taken place, if desired, individually or conjointly, in a manner which is in itself known. Thus it is preferably possible, for example, to protect amino, hydroxyl, carboxyl or phosphono groups in an acyl radical $R_1^A$ or $R_1^b$, for example in the form of acylamino groups, such as those mentioned above, for example 2,2,2-trichloroethoxycarbonylamino, 2-bromoethoxycarbonylamino, 4-methoxybenzyloxycarbonylamino, diphenylmethoxycarbonylamino or tert.-butoxycarbonylamino groups, of arylthioamino or aryl-lower alkylthioamino groups, for example 2-nitrophenylthioamino groups, or arylsulphonylamino groups, for example 4-methylphenylsulphonylamino groups, or of 1-lower alkoxycarbonyl-2-propylideneamino groups, or, respectively, of acyloxy groups, such as those mentioned above, for example tert.-butoxycarbonyloxy, 2,2,2-trichloroethoxycarbonyloxy or 2-bromoethoxycarbonyloxy groups, or, respectively, of esterified carboxyl groups, such as those mentioned above, for example diphenylmethoxycarbonyl groups, or, respectively, O,O'-disubstituted phosphono groups, such as those mentioned above, for example O,O'-di-lower alkylphosphono groups, for example O,O'-dimethylphosphono groups and subsequently, optionally after conversion of the protective group, for example of a 2-bromoethoxycarbonyl group into a 2-iodoethoxycarbonyl group, to split the protected group in a manner which is in itself known and depending on the nature of the protective group, for example a 2,2,2-trichloroethoxycarbonylamino or 2-iodoethoxycarbonylamino group by treatment with suitable reducing agents, such as zinc in the presence of aqueous acetic acid, a diphenylmethoxycarbonylamino or tert.-butoxycarbonylamino group by treatment with formic acid or trifluoroacetic acid, an arylthioamino or aryl-lower alkylthioamino group by treatment with a nucleophilic reagent, such as sulphurous acid, an arylsulphonylamino group by means of electrolytic reduction, a 1-lower alkoxycarbonyl-2-propylideneamino group by treatment with an aqueous mineral acid, or a tert.-butoxycarbonyloxy group by treatment with formic acid or trifluoro acetic acid, or a 2,2,2-trichloroethoxycarbonyloxy group by treatment with a chemical reducing agent, such as zinc in the presence of aqueous acetic acid, or a diphenylmethoxycarbonyl group by treatment with formic acid or trifluoroacetic acid or by hydrolysis, or an O,O'-disubstituted phosphono group by treatment with an alkali metal halide, the splitting being carried out if desired, for example partially.

In a compound of the formula IA or IB obtainable according to the invention and possessing a protected, especially esterified, carboxyl group of the formula $-C(=O)-R_2^A$, the latter can be converted into the free carboxyl group in a manner which is in itself known, for example depending on the nature of the group $R_2^A$. An esterified carboxyl group, for example a carboxyl group esterified by a lower alkyl radical, especially methyl or ethyl, especially in a 2-cephem compound of the formula IB, can be converted into a free carboxyl group by hydrolysis in a weakly basic medium, for example by treatment with an aqueous solution of an alkali metal hydroxide or carbonate or alkaline earth metal hydroxide or carbonate, for example sodium hydroxide or potassium hydroxide, preferably at a pH value of about 9 to 10, and optionally in the presence of a lower alkanol. A carboxyl group esterified by a suitable 2-halogeno-lower alkyl group or by an arylcarbonylmethyl group can be split, for example, by treatment with a chemical reducing agent, such as a metal, for example zinc, or a reducing metal salt, such as a chromium-II salt, for example chromium-II chloride, usually in the presence of a hydrogen donor which is capable of producing nascent hydrogen together with the metal, such as an acid, above all acetic acid and also formic acid, or an alcohol, water being added preferably, a carboxyl group esterified by an arylcarbonylmethyl group can also be split by treatment with a nucleophilic, preferably salt-forming, reagent, such as sodium thiophenolate or sodium iodide, a carboxyl group esterified by a suitable arylmethyl group can be split, for example, by irradiation, preferably with ultraviolet light, for example below 290 mµ, if the arylmethyl group represents, for example, a benzyl radical which is optionally substituted in the 3-, 4- and/or 5-position, for example by lower alkoxy and/or nitro groups, or with ultraviolet light of longer wavelengths, for example above 290 mµ, if the arylmethyl group denotes, for example, a benzyl radical which is substituted by a nitro group in the 2-position, a carboxyl group which is esterified by a suitably substituted methyl group, such as tert.-butyl or diphenylmethyl can be split, for example, by treatment with a suitable acid agent, such as formic acid or trifluoroacetic acid, optionally with the addition of a nucleophilic compound, such as phenol or anisole, an activated esterified carboxyl group, and also a carboxyl group present in the form of an anhydride, can be split by hydrolysis for example by treatment with an acid or weakly basic aqueous agent, such as hydrochloric acid or aqueous sodium bicarbonate or an aqueous potassium phosphate buffer of pH about 7 to about 9, and an esterified carboxyl group which can be split hydrogenolytically can be split by hydrogenolysis, for example by treatment with hydrogen in the presence of a noble metal catalyst, for example a palladium catalyst.

A carboxyl group protected, for example, by silylation or stannylation can be liberated in the usual manner, for example by treatment with water or an alcohol.

Resulting compounds of the formula IA or IB can be converted in a manner which is in itself known into other compounds of the formula IA or IB.

In a resulting compound it is possible, for example, to split off an amino protective group $R_1^A$ or $R_1^b$, especially an easily removable acyl group, in a manner which is in itself known, for example an α-polybranched lower alkoxycarbonyl group, such as tert.-butoxycarbonyl, by treatment with trifluoroacetic acid, and a 2-halogeno-lower alkoxycarbonyl group, such as 2,2,2-trichloroethoxycarbonyl or 2-iodoethoxycarbonyl or a phenacyloxycarbonyl group, by treatment with a suitable reducing metal or corresponding metal compound, for example zinc, or a chromium-II compound, such as chromium-II chloride or chromium-II acetate, advantageously in the presence of an agent which together with the metal or the metal compound generates nascent hydrogen, preferably in the presence of aqueous acetic acid.

It is furthermore possible, in a resulting compound of the formula IA or IB, wherein a carboxyl group of the formula —C(=O)—R₂ preferably represents a carboxyl group which is protected, for example by esterification, including by silylation, for example by reaction with a suitable organic halogenosilicon compound or halogentin-IV compound, such as trimethyl chlorosilane or tri-n-butyl-tin chloride, to split off an acyl group $R_1^A$ or $R_1^b$, wherein optionally present free functional groups are optionally protected, by treatment with an imide-halide-forming agent, reaction of the resulting imide-halide with an alcohol and splitting of the imino-ether formed, it being possible for a protected carboxyl group, for example a carboxyl group protected by an organic silyl radical, already to be liberated in the course of the reaction.

Imide-halide-forming agents in which halogen is bonded to an electrophilic central atom are above all acid halides, such as acid bromides and especially acid chlorides. The acid halides are above all acid halides of inorganic acids, above all of acids containing phosphorus, such as phosphorus oxyhalides, phosphorus trihalides and especially phosphorus pentahalides, for example phosphorus oxychloride, phosphorus trichloride and above all phosphorus pentachloride, and also pyrocatechyl-phosphorus trichloride, as well as acid halides, especially acid chlorides, of acids containing sulphur or of carboxylic acids, such as thionyl chloride, phosgene or oxalyl chloride.

The reaction with one of the imide-halide-forming agents mentioned is usually carried out in the present of a suitable base, especially of an organic base, above all of a tertiary amine, for example a tertiary aliphatic monoamine or diamine, such as a tri-lower alkylamine, for example trimethylamine, triethylamine or N,N-diisopropyl-N-ethylamine, also a N,N,N',N'-tetra-lower alkyl-lower alkylenediamine, for example N,N,N',N'-tetramethyl-1,5-pentylenediamine or N,N,N',N'-tetramethyl-1,6-hexylenediamine, a monocyclic or bicyclic monoamine or diamine, such as a N-substituted, for example N-lower alkylated, alkyleneamine, azaalkyleneamine or oxaalkyleneamine, for example N-methyl-piperidine or N-methyl-morpholine, as well as 2,3,4,6,7,8-hexahydro-pyrrolo[1,2-a]pyrimidine (diazabicyclononene; DBN), or a tertiary aromatic amine such as a di-lower alkylaniline, for example N,N-dimethylaniline, or above all a tertiary heterocyclic, monocyclic or bicyclic, base, such as quinoline or isoquinoline, especially pyridine, preferably in the presence of a solvent, such as an optionally halogenated, for example chlorinated, aliphatic or aromatic hydrocarbon, for example methylene chloride. It is possible to use approximately equimolar amounts of the imide-halide-forming agent and of the base; the latter can however also be present in more than or less than equimolar amount, for example in about 0.2-fold to about 1-fold amount or in, say, up to 10-fold, in particular about 3-fold to 5-fold, excess.

The reaction with the imide-halide-forming agent is preferably carried out with cooling, for example at temperatures of about −50° C. to about +10° C., but is also possible to work at higher temperatures, that is to say, for example, up to about 75° C., if the stability of the starting substances and of the products permits a higher temperature.

The imide-halide product which is usually further processed without isolation, is reacted according to the process with an alcohol, preferably in the presence of one of the above-mentioned bases, to give the imino-ether. Examples of suitable alcohols are aliphatic as well as araliphatic alcohols, above all optionally substituted, such as halogenated, for example chlorinated, lower alkanols or lower alkanols possessing additional hydroxyl groups, for example ethanol, propanol or butanol but especially methanol, also 2-halogeno-lower alkanols, for example 2,2,2-trichloroethanol or 2-bromoethanol, and optionally substituted phenyl-lower alkanols, such as benzyl alcohol. Usually an excess, for example up to about 100-fold excess, of the alcohol is employed and the reaction is preferably carried out with cooling, for example at temperatures of about −50° C. to about 10° C.

The imino-ether product can advantageously be split without isolation. The splitting of the imino-ether can be achieved by treatment with a suitable hydroxy compound, preferably by means of hydrolysis, and also by alcoholysis, and the latter can take place directly following the formation of the imino-ether, if an excess of the alcohol is used. Preferably, water or an alcohol, especially a lower alkanol, for example methanol, or an aqueous mixture of an organic solvent, such as an alcohol, is used. The reaction is usually carried out in an acid medium, for example at a pH value of about 1 to about 5 which can, if necessary, be obtained by adding a basic agent, such as an aqueous alkali metal hydroxide, for example sodium hydroxide or potassium hydroxide, or an acid, for example a mineral acid, or an organic acid, such as hydrochloric acid, sulphuric acid, phosphoric acid, fluoboric acid, trifluoroacetic acid or p-toluenesulphonic acid.

The three-stage process for splitting off an acyl group, described above, is advantageously carried out without isolation of the imide-halide and imino-ether intermediate products, usually in the presence of an organic solvent which is inert towards the reactants, such as an optionally halogenated hydrocarbon, for example methylene chloride, and/or in an inert gas atmosphere, such as a nitrogen atmosphere.

If the imide-halide intermediate product obtainable according to the above process, instead of being reacted with an alcohol, is reacted with a salt, such as an alkali metal salt, of a carboxylic acid, especially of a sterically hindered carboxylic acid, a compound of the formula IA or IB, wherein both radicals $R_1{}^a$ and $R_1{}^b$ represent acyl groups, is obtained.

In a compound of the formula IA or IB, wherein both radicals $R_1{}^a$ and $R_1{}^b$ represent acyl groups, one of these groups, preferably the sterically less hindered group, can be removed selectively, for example by hydrolysis or aminolysis.

In a compound of the formulae IA or IB, wherein $R_1{}^A$ and $R_1{}^b$ together with the nitrogen atom represent a phthalimido group, the latter can be converted into the free amino group, for example by hydrazinolysis, that is to say on treatment of such a compound with hydrazine.

Certain acyl radicals $R_1{}^A$ of an acylamino grouping in compounds obtainable according to the invention such as, for example, the 5-amino-5-carboxy-valeryl radical, wherein carboxyl is optionally protected, for example by esterification, especially by diphenylmethyl, and/or the amino group is optionally protected, for example by acylation, especially by an acyl radical of an organic carboxylic acid, such as halogeno-lower alkanoyl, such as dichloroacetyl, or phthaloyl, can also be split off by treatment with a nitrosilylating agent, such as nitrosyl chloride, with a carbocyclic arenediazonium salt, such as benzenediazonium chloride, or with an agent which releases positive halogen, such as a N-halogeno-amide or -imide, for example N-bromosuccinimide, preferably in a suitable solvent or solvent mixture, such as formic acid, together with a nitro- or cyano-lower alkane, and treatment of the reaction product with a hydroxylic agent, such as water or a lower alkanol, for example methanol or, if in the 5-amino-5-carboxy-valeryl radical $R_1{}^A$ the amino group is unsubstituted and the carboxyl group is protected, for example by esterification, and $R_1{}^b$ preferably represents an acyl radical but can also denote hydrogen, by leaving the substance to stand in an inert solvent, such as dioxane or a halogenated aliphatic hydrocarbon, for example methylene chloride and, if necessary, working up the free or monoacylated amino compound according to methods which are in themselves known.

A formyl group $R_1{}^A$ can also be split off by treatment with an acid agent, for example p-toluenesulphonic acid or hydrochloric acid, a weakly basic agent, for example dilute ammonia, or a decarbonylating agent, for example tris-(triphenylphosphine)-rhodium chloride.

A triarylmethyl group, such as the trityl group $R_1{}^4$, can be split off, for example, by treatment with an acid agent, such as a mineral acid, for example hydrochloric acid.

In a compound of the formula IA or IB, wherein $R_1{}^a$ and $R_1{}^b$ represent hydrogen, the free amino group can be substituted according to methods which are in themselves known, above all acylated by treatment with acids, such as carboxylic acids, or reactive derivatives thereof.

If a free acid wherein, preferably, optionally present functional groups, such as an optionally present amino group, are protected, is employed for the acylation, suitable condensation agents are usually employed, such as carbodiimides, for example N,N'-diethyl-, N,N'-dipropyl-, N,N'-diisopropyl-, N,N'-dicyclohexyl- or N-ethyl-N'-3-dimethylaminopropylcarbodiimide, suitable carbonyl compounds, for example carbonyl diimidazole, or isoxazolinium salts, for example N-ethyl-5-phenyl-isoxazolinium-3'-sulphonate and N-tert.-butyl-5-methylisoxazolinium perchlorate, or a suitable acylamino compound, for example 2-ethoxy-1-ethoxycarbonyl-1,2-dihydroquinoline.

The condensation reaction is preferably carried out in one of the anhydrous reaction media mentioned later, for example in methylene chloride, dimethylformamide or acetonitrile.

An amide-forming functional derivative of an acid, wherein optionally present groups, such as an optionally present amino group, are preferably protected, is above all an anhydride of such an acid, including, and preferably, a mixed anhydride. Mixed anhydrides are, for example, those with inorganic acids, especially with hydrogen halide acids, that is to say the corresponding acid halides, for example acid chlorides or acid bromides, and also with hydrazoic acid, that is to say the corresponding acid azides, with an acid containing phosphorus, for example phosphoric acid or phosphorous acid, with an acid containing sulphur, for example sulphuric acid, or with hydrocyanic acid. Further mixed anhydrides are, for example, those with organic acids, such as organic carboxylic acids, such as with lower alkanecarboxylic acids which are optionally substituted, for example by halogen, such as fluorine or chlorine, for example pivalic acid or trichloroacetic acid, or with half-esters, especially lower alkyl half-esters, of carbonic acid, such as the ethyl half-ester or isobutyl half-ester of carbonic acid, or with organic, especially aliphatic or aromatic, sulphonic acids, for example p-toluenesulphonic acid.

It is furthermore possible to use, as acylating agents, internal anhydrides, such as ketenes, for example diketene, isocyanates, (that is to say internal anhydrides of carbamic acid compounds) or internal anhydrides of carboxylic acid compounds having carboxyl-substituted hydroxyl or amino groups, such as mandelic acid O-carboxanhydride or the anhydride of 1-N-carboxyamino-cyclohexanecarboxylic acid.

Further acid derivatives suitable for reaction with the free amino group are activated esters, wherein the optionally present functional groups are usually protected, such as esters with vinylogous alcohols, (that is to say enols), such as vinylogous lower alkanols, or aryl esters, such as phenyl esters which are preferably substituted, for example by nitro or halogen, such as chlorine, for example pentachlorophenyl, 4-nitrophenyl or 2,4-dinitrophenyl esters, hetero-aromatic esters, such as benztriazole esters, or diacylimino esters, such as succinylimino esters or phthalylimino esters.

Further acylation derivatives are, for example, substituted forminimino derivatives, such as substituted N,N-dimethylchloroforminimino derivatives of acids, or N-substituted N,N-diacylamines, such as a N,N-diacylated aniline.

The acylation with an acid derivative, such as an anhydride, and especially with an acid halide, can be carried out in the presence of an acid-binding agent, for example of an organic base, such as an organic amine, for example a tertiary amine, such as tri-lower alkylamine, for example triethylamine, N,N-di-lower alkylaniline, for example N,N-dimethylaniline, or a base of the pyridine type, for example pyridine, an inorganic base, for example an alkali metal hydroxide, carbonate or bicarbonate or an alkaline earth metal hydroxide, carbonate or bicarbonate, for example sodium hydroxide, carbonate or bicarbonate, potassium hydroxide, carbonate or bicarbonate or calcium hydroxide, carbonate or bicarbonate, or an oxirane, for example a lower 1,2-alkylene oxide, such as ethylene oxide or propylene oxide.

The above acylation can be carried out in an aqueous or, preferably, non-aqueous solvent or solvent mixture, for example in a carboxylic acid amide, such as a N,N-di-lower alkylamide, for examle dimethylformamide, a halogenated hydrocarbon, for example methylene chloride, carbon tetrachloride or chlorobenzene, a ketone, for example acetone, an ester, for example ethyl acetate, or a nitrile, for example acetonitrile, or mixtures thereof, and, if necessary, at lowered or elevated temperature and/or in an inert gas atmosphere, for example a nitrogen atmosphere.

In the above N-acylation reactions it is possible to start from compounds of the formulae IA or IB, wherein $R_2$ has the above meaning, and compounds having free carboxyl groups of the formula —C(=O)—$R_2$, wherein $R_2$ represents hydroxyl, can also be used in the form of salts, for example ammonium salts, such as with triethylamine, or in the form of a compound with a carboxyl group protected by reaction with a suitable organic phosphorus halide compound, such as with a lower alkyl- or lower alkoxy-phosphorus dihalide, such as methyl-phosphorus dichloride, ethyl phosphorus dibromide or methoxyphosphorus dichloride; in the resulting acylation product the protected carboxyl group can be liberated in a manner which is in itself known, for example as described above, including by hydrolysis or alcoholysis.

An acyl group can also be introduced by acylating a compound of the formula IA or IB, wherein $R_1^a$ and $R_1^b$ together represent an ylidene radical, (which can also be introduced subsequently, for example by treating a compound wherein $R_1^a$ and $R_1^b$ represent hydrogen, with an aldehyde, such as an aliphatic, aromatic or araliphatic aldehyde), for example according to the methods indicated above, and the acylation product can be hydrolysed, preferably in a neutral or weakly acid medium.

An acyl group can also be introduced stepwise. Thus, for example, it is possible to introduce into a compound of the formula IA or IB, having a free amino group, a halogeno-lower alkanoyl group, for example a bromoacetyl group, or, for example by treatment with a carbonic acid dihalide, such as phosgene, a halogenocarbonyl group, for example a chlorocarbonyl group, and to react a N-(halogeno-lower alkanoyl)-amino compound of N-(halogenocarbonyl)-amino compound thus obtainable with suitable exchange reagents, such as basic compounds, for example tetrazole, thio compounds, for example 2-mercapto-1-methyl-imidazole, or metal salts, for example sodium azide, or alcohols, such as lower alkanols, for example tert.-butanol and thus to obtain substituted N-lower alkanoyl-amino or N-hydroxycarbonylamino compounds.

In both reactants, free functional groups can transiently be protected during the acylation reaction, in a manner which is in itself known and be liberated, after the acylation, by means of methods which are in themselves known, for example as described above.

The acylation can also be effected by replacement of an already existing acyl group by another, preferably sterically hindered, acyl group, for example according to the process described above, by manufacturing the imide-halide compound, treating this with a salt of an acid and splitting off hydrolytically one of the acyl groups present in the product thus obtainable, usually the sterically less hindered acyl group.

It is furthermore possible, for example, to react a compound of the formula IA or IB, wherein $R_1^a$ represents a glycyl group which is preferably substituted in the α-position, such as phenylglycyl, and $R_1^b$ represents hydrogen, with an aldehyde, for example formaldehyde, or a ketone, such as a lower alkanone, for example acetone, and thus to arrive at compounds of the formula IA or IB, wherein $R_1^A$ and $R_1^b$ together with the nitrogen atom represent a 5-oxo-1,3-diaza-cyclopentyl radical which is preferably substituted in the 4-position and is optionally substituted in the 2-position.

In a compound of the formula IA or IB, wherein $R_1^a$ and $R_1^b$ represent hydrogen, the free amino group can also be protected by introducing a triarylmethyl group, for example by treatment with a reactive ester of a triarylmethanol, such as trityl chloride, preferably in the presence of a basic agent, such as pyridine.

An amino group can also be protected by introducing a silyl and stannyl group. Such groups are introduced in a manner which is in itself known, for example by treatment with a suitable silylating agent, such as with a dihalogeno-dilower alkylsilane, lower alkoxy-lower alkyl-dihalogeno-silane or tri-lower alkyl-silyl halide, for example dichlorodimethylsilane, methoxy-methyl-dichloro-silane, trimethylsilyl chloride or dimethyl-tert.-butyl-silyl chloride, such silyl halide compounds preferably being used in the presence of a base, for example pyridine, or by treatment with an optionally N-mono-lower alkylated, N,N-di-lower alkylated, N-tri-lower alkylsilylated or N-lower alkyl-N-tri-lower alkyl-silylated N-(tri-lower alkylsilyl)-amine (see, for example, British Patent No. 1,073,530), or with a silylated carboxylic acid amide, such as a bis-tri-lower alkylsilyl-acetamide, for example bis-trimethylsilyl-acetamide or trifluorosilylacetamide, or by treatment with a suitable stannylating agent, such as a bis-(tri-lower alkyl-tin) oxide, for example bis-(tri-n-butyl-tin) oxide, a tri-lower alkyl-tin hydroxide, for example triethyl-tin hydroxide, a tri-lower alkyl-lower alkoxy-tin compound, tetra-lower alkoxy-tin compound or tetra-lower alkyl-tin compound, or with a tri-lower alkyl-tin halide, for example tri-n-butyl-tin chloride (see, for example, Netherlands Published Specification 67/11,107).

In a compound of the formula IA or IB, obtainable according to the process, which contains a free carboxyl group of the formula —C(=O)R$_2$, such a group can be converted into a protected carboxyl group in a manner which is in itself known. Thus, a compound with an esterified carboxyl group is obtained, for example, by treatment with a suitable disazo compound, such as a diazo-lower alkane, for example diazomethane or diazobutane, or a phenyl-diazo-lower alkane, for example diphenyldiazomethane, if necessary in the presence of a Lewis acid, such as, for example, boron trifluoride, or by reaction with an alcohol suitable for the esterification reaction, in the presence of an esterifying agent, such as a carbodiimide, for example dicyclohexylcarbodiimide, as well as carbonyldiimidazole, and also with a N,N'-disubstituted O- or S-substituted isourea or isothiourea, wherein a O-substituent and S-substituent are, for example, lower alkyl, especially tert.-butyl, phenyl-lower alkyl or cycloalkyl, and N-substituents or N'-substituents are, for example, lower alkyl, especially isopropyl, cycloalkyl or phenyl, or according to any other known and suitable esterification process, such as reaction of a salt of the acid with a reactive ester of an alcohol and of a strong inorganic acid, or with a strong organic sulphonic acid. Furthermore, acid halides, such as acid chlorides (manufactured, for example, by treatment with oxalyl chloride), activated esters (formed, for example, with N-hydroxy-nitrogen compounds, such as N-hydroxy-succinimide), or mixed anhydrides (obtained, for example, with halogenoformic acid lower alkyl esters, such as chloroformic acid ethyl ester or chloroformic acid isobutyl ester, or with halogenoacetic acid halides, such as trifluoroacetic acid chloride) can be converted into an esterified carboxyl group by reaction with alcohols, optionally in the presence of a base, such as pyridine.

In a resulting compound having an esterified grouping of the formula —C(=O)—R$_2$, this grouping can be converted into a different esterified carboxyl group of this formula, for example 2-chloroethoxycarbonyl or 2-bromoethoxycarbonyl can be converted into 2-iodoethoxycarbonyl by treatment with an iodine salt, such as sodium iodide, in the presence of a suitable solvent, such as acetone.

Mixed anhydrides can be manufactured by reacting a compound of the formula IA or IB, having a free carboxyl group of the formula —C(=O)—R$_2$, preferably a salt, especially an alkali metal salt, for example a sodium salt, or ammonium salt, for example triethylammonium salt, thereof, with a reactive derivative, such as a halide, for example the chloride, of an acid, for example a halogenoformic acid lower alkyl ester or a lower alkanecarboxylic acid chloride.

In a compound obtainable according to the process, having a free carboxyl group of the formula —C(=O)—R$_2$, such a group can also be converted into an optionally substituted carbamoyl or hydrazinocarbonyl group, for which preferably reactive functionally modified derivatives, such as the abovementioned acid halides, and generally esters, including also the abovementioned activated esters, or mixed anhydrides of the appropriate acid are reacted with ammonia or amines, including hydroxylamine, or hydrazines.

A carboxyl group protected by an organic silyl or stannyl group can be formed in a manner which is in itself known, for example by treating compounds of the formulae IA or IB, wherein R$_2$ represents hydroxyl, or salts thereof, such as alkali metal salts thereof, for example sodium salts thereof, with a suitable silylating or stannylating agent, such as one of the abovementioned silylating or stannylating agents; see, for example, British Pat. No. 1,073,530 or Netherlands Published Specification No. 67/17,107.

It is furthermore possible to liberate modified functional substituents in groups $R_1^A$, $R_1^b$ and/or $R_2$, such as substituted amino groups, acylated hydroxyl groups, esterified carboxyl groups or O,O'-disubstituted phosphono groups, according to methods which are in themselves known, for example those described above, or functionally to modify free functional substituents in groups $R_1^A$, $R_1^b$ and/or $R_2$, such as free amino, hydroxyl, carboxyl or phosphono groups, according to processes which are in themselves known, for example acylation or esterification or substitution. Thus, for example, an amino group can be converted into a sulphoamino group by treatment with sulphur trioxide, preferably in the form of a complex with an organic base, such as a tri-lower alkylamine, for example triethylamine. Furthermore, the reaction mixture obtained by reaction of an acid addition salt of a 4-guanylsemicarbazide with sodium nitrite can be reacted with a compound of the formula IA or IB, wherein, for example, the amino protective group $R_1^A$ represents an optionally substituted glycyl group, and the amino group can thus be converted into a free-guanylureido group. Further, compounds with aliphatically bonded halogen, for example with an optionally substituted α-bromoacetyl grouping, can be reacted with esters of phosphorus acid, such as tri-lower alkyl-phosphite compounds, and corresponding phosphono compounds can thus be obtained.

A mixture of a compound of the formula IA and of the corresponding 1-oxide, obtainable according to the process, can be either directly oxidised to the 1-oxide of a compound of the formula IA, or reduced to a 3-cephem compound of the formula IA. These oxidation and reduction steps are described later in connection with the isomerisation of a 2-cephem compound of the formula IB to the corresponding 3-cephem compound of the formula IA, using a 1-oxide as the intermediate product.

Resulting cephem compounds of the formula IA and IB can be converted into 1-oxides of the corresponding 3-cephem compounds of the formula IA by oxidation with suitable oxidising agents, such as those described below. Resulting 1-oxides of 3-cephem compounds of the formula IA can be reduced to the corresponding 3-cephem compounds of the formula IA by reduction with suitable reducing agents such as, for example, those described below. In these reactions it is necessary to ensure that, if necessary, free functional groups are protected and are subsequently again liberated, if desired.

Cephem compounds obtained can be isomerised. Thus, resulting 2-cephem compounds of the formula IB can be converted into the corresponding 3-cephem compounds of the formula IA by isomerising a 2-cephem compound of the formula IB wherein free functional groups can, if appropriate, be protected transiently, for example as indicated. In this reaction it is possible to use, for example, 2-cephem compounds of the formula IB wherein the group of the formula —C(=O)—R$_2$ represents a free or protected carboxyl group, it also being possible to form a protected carboxyl group during the reaction.

Thus it is possible to isomerise a 2-cephem compound of the formula IB by treating it with a weakly basic agent and isolating the corresponding 3-cephem compound of the formula IA from an equilibrium mixture of the 2- and 3-cephem compounds which may be obtained.

Examples of suitable isomerising agents are organic nitrogen-containing bases, such as tertiary heterocyclic bases of aromatic character, and above all tertiary aliphatic, azacycloaliphatic or araliphatic bases, such as N,N,N-tri-lower alkylamines, for example N,N,N-trimethylamine, N,N-dimethyl-N-ethylamine, N,N,N-triethylamine or N,N-diisopropyl-N-ethylamine, N-lower alkyl-azacycloalkanes, for example N-methyl-piperidine, or N-phenyl-lower alkyl-N,N-di-lower alkyl-amines, for example N-benzyl-N,N-dimethylamine, as well as mixtures thereof, such as the mixture of a base of the pyridine type, for example pyridine, and a N,N,N-tri-lower alkylamine, for example pyridine and triethylamine. Furthermore it is also possible to use inorganic or organic salts of bases, especially of medium-strength to strong bases, with weak acids, such as alkali metal salts or ammonium salts of lower alkanecarboxylic acids, for example sodium acetate, triethylammonium acetate or or N-methyl-piperidine acetate, as well as other analogous bases or mixtures of such basic agents.

The above isomerisation with basic agents can be carried out for example, in the presence of a derivative of a carboxylic acid which is suitable for forming a mixed anhydride, such as a carboxylic acid anhydride or carboxylic acid halide, for example with pyridine in the presence of acetic anhydride. This reaction is preferably carried out in an anhydrous medium, in the presence or absence of a solvent, such as an optionally halogenated, for example chlorinated, aliphatic, cycloaliphatic or aromatic hydrocarbon, or of a solvent mixture, it being possible for bases used as reactants and liquid under the reaction conditions at the same time also to serve as solvents, if necessary with cooling or heating, preferably in a temperature range of about $-30°$ C. to about $+100°$ C., in an inert gas atmosphere, for example a nitrogen atmosphere, and/or in a closed vessel.

The 3-cephem compounds of the formula IA, thus obtainable, can be separated from 2-cephem compounds of the formula IB which may still be present, in a manner which is in itself known, for example by adsorption and/or crystallisation.

The isomerisation of 2-cephem compounds of the formula IB can also be carried out by oxidising these in the 1-position, if desired separating an isomer mixture of the 1-oxides of 3-cephem compounds of the formula IA which may be obtained, and reducing the 1-oxides of the corresponding 3-cephem compounds of the formula IA, thus obtainable.

Suitable oxidising agents for the oxidation of 2-cephem compounds in the 1-position are inorganic per-acids which have a reduction potential of at least $+1.5$ volt and which consist of non-metallic elements, organic per-acids or mixtures of hydrogen peroxide and acids, especially organic carboxylic acids, having a dissociation constant of at least $10^{-5}$. Suitable inorganic per-acids are periodic acid and persulphuric acid. Organic per-acids are appropriate percarboxylic acids and persulphonic acids which can be added as such or can be formed in situ by the use of at least one equivalent of hydrogen peroxide and of a carboxylic acid. It is desirable to use a large excess of the carboxylic acid if, for example, acetic acid is used as the solvent. Suitable per-acids are, for example, performic acid, peracetic acid, pertrifluoroacetic acid, permaleic acid, perbenzoic acid, monoperphthalic acid or p-toluenepersulphuric acid.

The oxidation can also be carried out using hydrogen peroxide and catalytic amounts of an acid having a dissociation constant of at least $10^{-5}$, it being possible to employ low concentrations, for example 1-2% or less, but also larger amounts, of the acid. The activity of the mixture above all depends on the strength of the acid. Examples of suitable mixtures are those of hydrogen peroxide with acetic acid, perchloric acid or trifluoroacetic acid.

The above oxidation can be carried out in the presence of suitable catalysts. Thus, for example, the oxidation with percarboxylic acids can be catalysed by the presence of an acid having a dissociation constant of at least $10^{-5}$, its activity depending on its strength. Acids suitable as catalysts are, for example, acetic acid, perchloric acid and trifluoroacetic acid. Usually, at least equimolar amounts of the oxidising agent, and preferably a small excess of about 10% to about 20%, are used. The oxidation is carried out under mild conditions, for example at temperatures of about $-50°$ C. to about $+100°$ C., preferably of about $-10°$ C. to about $+40°$ C.

The oxidation of 2-cephem compounds to the 1-oxides of the corresponding 3-cephem compounds can also be carried out by treatment with ozone, as well as with organic hypohalite compounds, such as lower alkyl hypochlorites, for example tert.-butylhypochlorite, which are used in the presence of inert solvents, such as optionally halogenated hydrocarbons, for example methylene chloride, and at temperatures of about $-10°$ C. to about $+30°$ C., with periodate compounds, such as alkali metal periodates, for example potassium periodate, which are preferably used in an aqueous medium at a pH value of about 6 and at temperatures of about $-10°$ C. to about $+30°$ C., with iodobenzene dichloride, which is used in an aqueous medium, preferably in the presence of an organic base, for example pyridine, and with cooling, for example at temperatures of about $-20°$ C. to about $0°$, or with any other oxidising agent which is suitable for conversion of a thio group into a sulphoxide grouping.

In the 1-oxides of 3-cephem compounds of the formula IA, thus obtainable, especially in those compounds in which $R_1{}^a$, $R_1{}^b$ and $R_2$ have the abovementioned preferred meanings, the groups $R_1{}^a$, $R_1{}^b$ and/or $R_2$ can, within the defined framework, be converted into one another, split off or introduced. A mixture of isomeric α- and β-1-oxides can be separated, for example chromatographically.

The reduction of the oxides of 3-cephem compounds of the formula IA can be carried out in a manner which is in itself known, by treatment with a reducing agent, if necessary in the presence of an activating agent. Possible reducing agents are: catalytically activated hydrogen, using noble metal catalysts which contain palladium, platinum or rhodium and which are optionally employed together with a suitable carrier, such as charcoal or barium sulphate; reducing tin, iron, copper or manganese cations, which are used in the form of appropriate compounds or complexes of inorganic or organic nature, for example as tin-II chloride, fluoride, acetate or formate, iron-II chloride, sulphate, oxalate or succinate, copper-I chloride, benzoate or oxide, or manganese-II chloride, sulphate, acetate or oxide, or as complexes, for example with ethylenediaminetetraacetic acid or nitrilotriacetic acid; reducing dithionite, iodide or ferrocyanide anions which are used in the form of appropriate inorganic or organic salts, such as alkali metal salts, for example sodium dithionite or potassium dithionite, sodium iodide or potassium iodide, or sodium ferrocyanide or potassium ferrocyanide, or in the form of the corresponding acids, such as hydriodic acid; reducing trivalent inorganic or organic phosphorus compounds, such as phosphines, and also esters, amides and halides of phosphinous, phosphonous or phosphorous acids, as well as phosphorus-sulphur compounds corresponding to these phosphorus-oxygen compounds, in which compounds organic radicals above all represent aliphatic, aromatic or araliphatic radicals, for example optionally substituted lower alkyl, phenyl or phenyl-lower alkyl groups, such as, for example, triphenylphosphine, tri-n-butylphosphine, diphenylphosphinous acid methyl ester, diphenylchlorophosphine, phenyldichlorophosphine, benzenephosphonous acid dimethyl ester, butanephosphonous acid methyl ester, phosphorous acid triphenyl ester, phosphorous acid trimethyl ester, phosphorus trichloride, phosphorus tribromide and the like; reducing halogenosilane compounds which possess at least one hydrogen atom bonded to the silicon atom and which, in addition to halogen, such as chlorine, bromine or iodine, can also possess organic radicals, such as aliphatic or aromatic groups, for example optionally substituted lower alkyl or phenyl groups, such as chlorosilane, bromosilane, dichlorosilane or trichlorosilane, dibromosilane or tribromosilane, diphenylchlorosilane, dimethylchlorosilane and the like; reducing quaternary chloromethylene-iminium salts, especially chlorides or bromides, wherein the iminium group is substituted by a bivalent or two monovalent radicals, such as optionally substituted lower alkylene or lower alkyl groups, such as N-chloromethylene-N,N-diethyliminium chloride or N-chloromethylene-pyrrolidinium chloride; and complex metal hydrides, such as sodium borohydride, in the presence of suitable activating agents, such as cobalt-II chloride, as well as borane dichloride.

As activating agents which are used together with those of the abovementioned reducing agents which do not themselves possess Lewis acid properties, that is to say which above all are employed together with the dithionite, iodide or ferrocyanide reducing agents or the trivalent phosphorus reducing agents which do not contain halogen, or in the catalytic reduction, there should especially be mentioned organic carboxylic acid halides and sulphonic acid halides, also sulphur halides, phosphorus halides or silicon halides having the same or a greater second order hydrolysis constant than benzoyl chloride, for example phosgene, oxalyl chloride, acetic acid chloride or acetic acid bromide, or chloroacetic acid chloride; pivalic acid chloride, 4-methoxybenzoic acid chloride, 4-cyanobenzoic acid chloride, p-toluenesulphonic acid chloride, methanesulphonic acid chloride, thionyl chloride, phosphorus oxychloride, phosphorus trichloride, phosphorus tribromide, phenyldichlorophosphine, benzenephosphonous acid dichloride, dimethyldichlorosilane or trichlorosilane and also suitable acid anhydrides, such as trifluoroacetic acid anhydride, or cyclic sultones, such as ethanesultone, 1,3-propanesultone, 1,4-butanesultone or 1,3-hexanesultone.

The reduction is preferably carried out in the presence of solvents or mixtures thereof, the choice of which is above all determined by the solubility of the starting substances and the choice of the reducing agents, such as, for example, lower alkanecarboxylic acids or esters thereof, such as acetic acid and ethyl acetate, in the case of the catalytic reduction and, for example, optionally substituted, such as halogenated or nitrated, aliphatic, cycloaliphatic, aromatic or araliphatic hydrocarbons, for example benzene, methylene chloride, chloroform or nitromethane, suitable acid derivatives, such as lower alkanecarboxylic acid esters or nitriles, for example ethyl acetate or acetonitrile, or amides of inorganic or organic acids, for example dimethylformamide or hexamethylphosphoramide, ethers, for example diethyl ether, tetrahydrofurane or dioxane, ketones, for example acetone, or sulphones, especially aliphatic sulphones, for example dimethylsulphone or tetramethylenesulphone, and the like, in the case of the chemical reducing agents, these solvents preferably not containing any water. The reaction is usually carried out at temperatures of about $-20°$ C. to about $100°$ C., it being possible to carry out the reaction at lower temperatures if very reactive activating agents are used.

In the 3-cephem compounds of the formula IA, thus obtainable, $R_1{}^a$, $R_1{}^b$ and/or $R_2$ can be converted into other groups $R_1{}^a$, $R_1{}^b$ or $R_2$ as described above, it being necessary to bear in mind that the 3-cephem compounds are considerably more sensitive towards basic agents than the corresponding 2-cephem compounds of the formula IB.

Furthermore, 3-cephem compounds can be isomerised to 2-cephem compounds in a manner which is in itself known, and this reaction can be carried out by treatment with a base, preferably an organic base, such as a heterocyclic base, for example pyridine and/or a tertiary amine, such as a tri-lower alkylamine, for example triethylamine, and, if a free 3-cephem-4-carboxylic acid compound is used, additionally in the presence of a suitable acid derivative which can form a mixed anhydride group, such as a carboxylic acid anhydride, such as a lower alkanecarboxylic acid anhydride, for example acetic anhydride. The desired 2-cephem compound can be isolated, in a manner which is in itself known, from an equilibrium mixture of the 2- and 3-cephem compounds which may be obtained.

Salts of compounds of the formulae IA and IB can be manufactured in a manner which is in itself known. Thus, salts of such compounds which possess acid groups can be formed, for example, by treatment with metal compounds, such as alkali metal salts, of suitable carboxylic acids, for example the sodium salt of α-ethylcaproic acid, or with ammonia or a suitable organic amine, preferably using stoichiometric amounts or only a small excess of the salt-forming agent. Acid addition salts of compounds of the formulae IA and IB having basic groupings are obtained in the customary manner, for example by treatment with an acid or with a suitable anion exchange reagent. Internal salts of compounds of the formula IA and IB which contain a salt-forming amino group and a free carboxyl group can be formed, for example, by neutralising salts, such as acid addition salts, to the isoelectric point, for example with weak bases, or by treatment with liquid ion exchangers. Salts of 1-oxides of compounds of the formula IA having salt-forming groups can be manufactured analogously.

Salts can be converted into the free compounds in the customary manner, metal salts and ammonium salts, for example, by treatment with suitable acids, and acid addition salts, for example, by treatment with a suitable basic agent.

Resulting mixtures of isomers can be separated into the individual isomers according to methods which are in themselves known, mixtures of diastereomeric isomers, for example, by fractional crystallisation, adsorption chromatography (column chromatography or thin layer chromatography) or other suitable separation processes. Resulting racemates can be separated into the antipodes in the usual manner, if appropriate after introducing suitable salt-forming groupings, for example by forming a mixture of diastereomeric salts with optically active salt-forming agents, separating the mixture into the diastereomeric salts and converting the separated salts into the free compounds, or by fractional crystallisation from optically active solvents.

The process also encompasses those embodiments according to which compounds arising as intermediate products are used as starting substances and the remaining process steps are carried out with these, or the process is stopped at any stage; furthermore, starting substances can be used in the form of derivatives or be formed during the reaction.

Preferably, those starting substances are used, and the reaction conditions are so chosen, that the compounds initially mentioned as being particularly preferred are obtained.

The starting compounds of the formula II used according to the invention can be manufactured, for example, by converting the acetoxymethyl group in a cephem compound of the formula

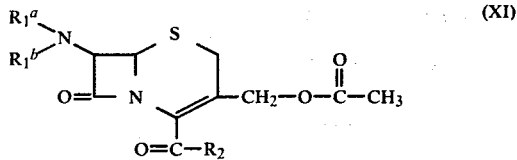

wherein $R_1^a$ preferably represents an amino protective group $R_1^A$ and wherein $R_2$ preferably represents hydroxyl, but also represents a group $R_2^A$, into the hydroxymethyl group, for example by hydrolysis in a weakly basic medium, such as with an aqueous sodium hydroxide solution at pH 9–10, or by treatment with a suitable esterase, such as an appropriate enzyme form *Rhizobium tritolii, Rhizobium lupinii, Rhizobium japonicum* or *Bacillus subtilis*, functionally modifying a free carboxyl group of the formula —C(=O)—$R_2$ in a suitable manner, for example esterifying it by treatment with a diazo compound, such as diphenyldiazomethane, and converting the hydroxymethyl group into a halogenomethyl group, for example a chloromethyl or iodomethyl group, for example by treatment with a halogenating agent, such as a chlorinating agent, for example thionyl chloride, or an iodinating agent, such as N-methyl-N,N'-di-cyclohexylcarbodiimidium iodide. A chloromethyl group is converted into the methylene group either directly, for example by treatment with a suitable chromium-II compound, such as an inorganic or organic salt of divalent chromium, for example chromium-II chloride or chromium-II acetate, in a suitable solvent, such as dimethylsulphoxide, or indirectly via the iodomethyl group (which can be formed, for example, by treating the chloromethyl compound with a metal iodide, such as sodium iodide, in a suitable solvent, such as acetone), by treatment of such an iodomethyl compound with a suitable reducing agent, such as zinc in the presence of acetic acid. The methylene group in a compound of the formula

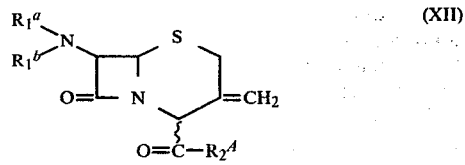

which is also obtainable from compounds of the formula XI by, for example, electrochemical reduction or reduction with chromium-II salts or aluminium amalgam, is oxidatively degraded according to the process described below. In a cepham-3-one compound thus obtainable, in which both radicals $R_1^a$ and $R_1^b$ represent hydrogen, the free amino group can be protected by an appropriate protective group, for example according to the process described above.

The oxidative splitting off of the methylene group in compounds of the formula XII to form an oxo group in the 3-position of the cepham ring skeleton is preferably carried out by forming an ozonide compound by treatment with ozone. Herein, ozone is usually employed in the presence of a solvent, such as an alcohol, for example a lower alkanol, such as methanol or ethanol, a ketone, for example a lower alkanone, such as acetone, an optionally halogenated aliphatic, cycloaliphatic or aromatic hydrocarbon for example a halogeno-lower alkane, such as methylene chloride or carbon tetrachloride, or a solvent mixture, including an aqueous mixture, and with cooling or slight warming, for example at temperatures of about −90° C. to about +40° C.

An ozonide formed as an intermediate product is split by reduction, for which it is possible to use catalytically activated hydrogen, for example hydrogen in the presence of a heavy metal hydrogenation catalyst, such as a nickel catalyst or a palladium catalyst, preferably on a suitable carrier, such as calcium carbonate or charcoal, or chemical reducing agents, such as reducing heavy metals, including heavy metal alloys or amalgams, for example zinc, in the presence of a hydrogen donor, such as an acid, for example acetic acid, or an alcohol for example a lower alkanol, reducing inorganic salts, such as alkali metal iodides, for example sodium iodide, in the presence of a hydrogen donor, such as an acid, for example acetic acid, or reducing organic compounds, such as formic acid, a reducing sulphide compound such as a di-lower alkylsulphide, for example dimethylsulphide, a reducing organic phosphorus compound, such as a phosphine, which can optionally contain substituted aliphatic or aromatic hydrocarbon radicals as substituents, such as tri-lower alkyl-phosphines, for example tri-n-butylphosphine, or triarylphosphines, for example triphenylphosphine, also phosphites which contain optionally substituted aliphatic hydrocarbon radicals as substituents, such as tri-lower alkylphosphites, usually in the form of corresponding alcohol adduct compounds, such as trimethylphosphite, or phosphorous acid triamides which contain optionally substituted aliphatic hydrocarbon radicals as substituents, such as hexa-lower alkylphosphorous acid triamides, such as hexamethyl phosphorous acid triamide, the latter preferably in the form of a methanol adduct, or tetracyanoethylene. The splitting of the ozonide, which is usually not isolated, is normally carried out under the conditions which are employed for its manufacture, that is to say in the presence of a suitable solvent or solvent mixture, and with cooling or slight warming.

Depending on how the oxidation reaction is carried out, a compound of the formula II or the corresponding 1-oxide or a mixture of the two compounds is obtained. Such a mixture can be separated into the compound of the formula II and the corresponding 1-oxide and be used as such, or can be oxidised to the pure 1-oxide of a compound of the formula IA.

A mixture of a compound of the formula II with the corresponding 1-oxide can be separated into the individual components in the usual manner, for example by fractional crystallisation or by chromatography (for example column chromatography or thin layer chromatography).

It is furthermore also possible to oxidise a mixture, obtainable according to the process, of a compound of the formula II and a 1-oxide thereof, directly to the 1-oxide of a compound of the formula II, employing the oxidising agents described above for the manufacture of 1-oxide compounds.

In the conversion, according to the invention, of the starting substances of the formula II to the enol derivatives of the formulae IA and IB of the present invention, it is not necessary to isolate the starting substances of the formula II after they have been manufactured; they can preferably be converted directly into the compounds of the formula IA and IB in the form of the crude reaction mixture after the manufacture from the compounds of the formula XII.

The pharmacologically usable compounds of the present invention can, for example, be used for the manufacture of pharmaceutical preparations which contain an effective amount of reactive substance together with, or mixed with, inorganic or organic, solid or liquid, pharmaceutically usable excipients which are suitable for enteral administration or preferably for parenteral administration. Thus, tablets or gelatine capsules are used which contain the active compound together with diluents, for example lactose, dextrose, sucrose, mannitol, sorbitol, cellulose and/or glycine, and lubricants, for example silica, talc, stearic acid or salts thereof, such as magnesium stearate or calcium stearate, and/or polyethylene glycol; tablets also contain binders, for example magnesium aluminium silicate, starches, such as corn starch, wheat starch, rice starch or arrowroot starch, gelatine, tragacanth, methylcellulose, sodium carboxymethylcellulose and/or polyvinylpyrrolidone and, if desired, disintegrating agents, for example starches, agar, alginic acid or a salt thereof, such as sodium alginate, and/or effervescent mixtures, or adsorbents, dyestuffs, flavouring substances and sweeteners. Furthermore, the new pharmacologically active compounds can be used in the form of injectable preparations, for example preparations which can be administered intravenously, or of infusion solutions. Such solutions are, preferably, isotonic aqueous solutions or suspensions and these can, for example, be manufactured before use from lyophilised preparations which contain the active substance by itself or together with an excipient, for example mannitol. The pharmaceutical preparations can be sterilised and/or contain auxiliaries, for example preservatives, stabilisers, wetting agents or emulsifiers, solubilising agents, salts for regulating the osmotic pressure and/or buffers. The present pharmaceutical preparations which can, if desired, contain further pharmacologically valuable substances, are manufactured in a manner which is in itself known, for example by means of conventional mixing, granulating, dragée-making, dissolving or lyophilising processes, and contain from about 0.1% to 100%, especially from about 1% to about 50%, of lyophilised products or up to 100% of the active substance.

In the context of the present description, the organic radicals described as "lower" contain, unless expressly defined, up to 7, preferably up to 4, carbon atoms; acyl radicals contain up to 20, preferably up to 12, and above all up to 7, carbon atoms.

The examples which follow serve to illustrate the invention.

EXAMPLE 1

A solution of 1.0 g of 3-methylene-7$\beta$-phenylacetylamino-cepham-4$\alpha$-carboxylic acid diphenylmethyl ester in 250 ml of methylene chloride is treated for 8½ minutes at $-70°$ C. with an oxygen-ozone mixture (0.265 mmol of ozone/minute) and 1 ml of dimethyl sulphide is added to the reaction mixture. The mixture is stirred for 30 minutes at $-70°$ C. and for 1½ hours at room temperature and is then evaporated to dryness under reduced pressure. The residue, containing a mixture of 7$\beta$-phenylacetylaminocepham-3-one-4$\xi$-carboxylic acid diphenylmethyl ester and of 7$\beta$-phenylacetylamino-cepham-3-one-4$\xi$-carboxylic acid diphenylmethyl ester 1-oxide is taken up in 50 ml of methanol and treated with an excess of diazomethane (in the form of a solution in diethyl ether) at 0° C. The whole is stirred for 15 minutes at 0° C. and then evaporated under reduced pressure. The residue is chromatographed on 50 g of silica gel. Elution with a 4:1 mixture of toluene and ethyl acetate yields 3-methoxy-7$\beta$-phenylacetylamino-2-cephem-4$\alpha$-carboxylic acid diphenylmethyl ester of Rf=0.57 (system: toluene/ethyl acetate, 1:1); melting point 174°–177° C. after recrystallization from a mixture of methylene chloride and pentane; ultraviolet absorption spectrum (in 95% strength aqueous ethanol): $\lambda_{max}=258$ m$\mu$ ($\epsilon=4,000$); infrared absorption spectrum (in methylene chloride): characteristic bands at 2.96$\mu$, 5.63$\mu$, 5.74$\mu$, 5.92$\mu$, 6.15$\mu$ and 6.66$\mu$; followed by 3-methoxy-7$\beta$-phenylacetylamino-3-cephem-4-carboxylic acid diphenylmethyl ester of Rf~0.37 (system: toluene/ethyl acetate 1:1): ultraviolet absorption spectrum (in 95% strength aqueous ethanol): $\lambda_{max}=258$ m$\mu$ ($\epsilon=6,340$), $\lambda_{max}=264$ m$\mu$ ($\epsilon=6,350$) and $\lambda_{shoulder}=281$ m$\mu$ ($\epsilon=5,600$); infrared absorption spectrum (in methylene chloride): characteristic bands at 2.94$\mu$, 3.02$\mu$, 5.62$\mu$, 5.83$\mu$, 5.93$\mu$, 6.26$\mu$ and 6.70$\mu$; elution with ethyl acetate yields 3-methoxy-7$\beta$-phenylacetylamino-3-cephem-4-carboxylic acid diphenylmethyl ester 1-oxide of Rf=0.31 (system: ethyl acetate); melting point 152°–155° C. after crystallisation from a mixture of acetone and diethyl ether; ultraviolet absorption spectrum (in 95% strength aqueous ethanol): $\lambda_{max}=288$ m$\mu$ ($\epsilon=3,610$) and $\lambda_{shoulder}=247$ m$\mu$; infrared absorption spectrum (in methylene chloride): characteristic bands at 2.94$\mu$, 5.59$\mu$, 5.81$\mu$, 5.95$\mu$, 6.22$\mu$ and 6.61$\mu$.

The starting material can be manufactured as follows:

A solution of 11.82 g of the crude sodium salt of 3-hydroxymethyl-7$\beta$-phenylacetylamino-3-cephem-4-carboxylic acid (manufactured by enzymatic desacetylation of the sodium salt of 3-acetoxymethyl-7$\beta$-phenylacetylamino-3-cephem-4-carboxylic acid with the aid of a purified enzyme extract from *Bacillus subtilis*, strain ATCC 6,633, and subsequent lyophilisation of the reaction solution) in 200 ml of water is covered with 400 ml of ethyl acetate and acidified to a pH value of 2 with concentrated aqueous phosphoric acid. the aqueous phase is separated off and twice re-extracted with 150 ml of ethyl acetate at a time. The combined organic mixture are washed four times with 50 ml of water at a time, dried over magnesium sulphate and then concentrated to about 400 ml. Excess diphenyldiazomethane is added to the solution, which is left to stand for 3 hours at room temperature, and the granular crystalline precipitate is then filtered off. The filtrate is concentrated to about 200 ml, cyclohexane is added whilst warm and after cooling to room temperature the mixture is left to stand for some time at about 4° C. The precipitate is filtered off and recrystallized from a mixture of acetone and cyclohexane; the 3-hydroxymethyl-7β-phenylacetylamino-3-cephem-4-carboxylic acid diphenylmethyl ester thus obtained melts at 176°–176.5° C. (uncorrected); $[\alpha]_D^{20} = -6° \pm 1°$ (c=1.231% in chloroform); thin layer chromatogram (silica gel; detection with iodine vapour or ultraviolet light, $\lambda_{254\ m\mu}$); Rf=0.42 (system: chloroform/acetone, 4:1), Rf=0.43 (system: toluene/acetone, 2:1), and Rf=0.41 (system: methylene choride/acetone, 6:1).

1.03 g of 3-hydroxymethyl-7β-phenylacetylamino-3-cephem-4-carboxylic acid diphenylmethyl ester and 1.05 g of N-methyl-N,N'-dicyclohexylcarbodiimidium iodide are dissolved in 25 ml of absolute tetrahydrofuran under a nitrogen atmosphere and warmed at 35° C. for one hour. Thereafter, a further 1.05 g of N-methyl-N,N'-dicyclohexylcarbodiimidium iodide, in 15 ml of absolute tetrahydrofurane, is added and the mixture is left to stand for 17 hours at room temperature under a nitrogen atmosphere. The reaction mixture is freed of the solvent on a rotary evaporator under reduced pressure. The residue is taken up in methylene chloride and filtered through a column of 50 g of silica gel (with addition of 10% of distilled water); the column is rinsed with 4 portions of methylene chloride, each of 100 ml. The eluate is concentrated to a small volume and chromatographed on a silica gel column (90 g; deactivated by adding 10% of distilled water). Non-polar impurities are eluted with a total of 900 ml of a 3:7 mixture of toluene and methylene chloride. Elution with 2 portions of methylene chloride, each of 200 ml, yields 3-iodomethyl-7β-phenylacetylamino-3-cephem-4-carboxylic acid diphenylmethyl ester; the fractions which according to a thin layer chromatogram are a single substance are lyophilised from benzene. Infrared absorption spectrum (in methylene chloride): characteristic bands at $3.00\mu$, $5.62\mu$, $5.82\mu$, $5.95\mu$, $6.70\mu$, $7.32\mu$ and $8.16\mu$.

The iodination reagent used above can be manufactured as follows:

42 g of freshly distilled N,N'-dicyclohexylcarbodiimide are dissolved in 90 ml of methyl iodide in a 250 ml round flask equipped with a magnetic stirrer and reflux condenser and fitted nitrogen bulb, at room temperature under a nitrogen atmosphere, and the colourless reaction mixture is stirred for 72 hours at a bath temperature of 70° C. At the end of the reaction time, the excess methyl iodide is distilled from the solution, which is now red-brown, under reduced pressure and the viscous red-brown residue is dissolved in 150 ml of absolute toluene at 40° C. The crystal mass, which crystallises out spontaneously within a few hours, is separated from the mother liquor with the aid of a glass suction filter with fitted nitrogen bulb, whilst excluding air, the reaction vessel is rinsed three times with 25 ml of absolute, ice-cold toluene at a time and the same toluene is used in order to wash the slightly yellowish crystal mass on the glass suction filter until it is colourless. After drying for 20 hours at 0.1 mm Hg and room temperature, the N-methyl-N,N'-dicyclohexylcarbodiimidium iodide is obtained in the form of colourless crystals, melting point 111°–113° C.; infrared absorption spectrum (in chloroform): characteristic bands at $4.72\mu$ and $6.00\mu$.

A solution of 0.400 g of 3-iodomethyl-7β-phenylacetylamino-3-cephem-4-carboxylic acid diphenylmethyl ester in 15 ml of 90% strength aqueous acetic acid is cooled to 0° C. in an ice bath and 2.0 g of zinc dust are added in portions whilst stirring well. After a reaction time of 30 minutes at 0° C. the unreacted zinc dust is filtered off by means of a suction filter covered with a layer of diatomaceous earth; the filter residue is repeatedly suspended in fresh methylene chloride and again filtered. The combined filtrates are concentrated under reduced pressure, mixed with absolute toluene and evaporated to dryness under reduced pressure. The residue is taken up in 50 ml of methylene chloride and 30 ml of an 0.5 molar aqueous dipotassium hydrogen phosphate solution, whilst stirring; the aqueous phase is separated off, re-extracted with two portions of methylene chloride, each of 30 ml, and discarded. The organic extracts are repeatedly washed with a saturated aqueous sodium chloride solution, dried over magnesium sulphate and evaporated under reduced pressure. The residue is chromatographed on a column of 22 g of silica gel (with addition of 10% of water). The 3-methylene-7β-phenylacetylamino-cepham-4α-carboxylic acid diphenylmethyl ester is eluted with methylene chloride, and with methylene chloride containing 2% of methyl acetate, and is crystallised from a mixture of methylene chloride and hexane, melting point 144°–147° C.; $[\alpha]_D^{20} = -18° \pm 1°$ (c=0.715 in chloroform); ultraviolet absorption spectrum (in 95% strength aqueous ethanol): $\lambda_{max} = 254\ m\mu$ ($\epsilon = 1,540$) and $260\ m\mu$ ($\epsilon = 1.550$); infrared absorption spectrum (in methylene chloride): characteristic bands at $2.94\mu$, $5.65\mu$, $5.74\mu$, $5.94\mu$, $6.26\mu$ and $6.67\mu$.

EXAMPLE 2

A solution of 0.50 g of 3-methylene-7β-phenylacetylamino-cepham-4α-carboxylic acid diphenylmethyl ester in 50 ml of methanol is treated with an oxygen-ozone mixture at $-70°$ C. until a blue colouration starts to appear. The excess ozone is driven off with nitrogen; 0.5 ml of dimethyl sulphide is added and the mixture is stirred for 1½ hours at room temperature. The reaction mixture, containing a mixture of 7β-phenylacetylamino-cepham-3-one-4ξ-carboxylic acid diphenylmethyl ester and of 7β-phenylacetylamino-cepham-3-one-4ξ-carboxylic acid diphenylmethyl ester 1-oxide is then evaporated to dryness under reduced pressure. The residue is taken up in 10 ml of pyridine, 5 ml of acetic anhydride are added and the mixture is left to stand for 16 hours at 0° C. It is evaporated to dryness under a high vacuum; the residue is taken up in ethyl acetate and the organic solution is washed with a saturated aqueous sodium bicarbonate solution and a saturated aqueous sodium chloride solution, dried over sodium sulphate and evaporated under reduced pressure. The residue is chromatographed on 30 g of silica gel, 3-acetoxy-7β-phenylacetylamino-3-cephem-4-carboxylic acid diphenylmethyl ester being eluted with a 4:1 mixture of toluene and ethyl acetate. The product is crystallised from a mixture of acetone and diethyl ether, melting point 158°–160° C.; ultraviolet absorption spectrum (in 95% strength aqueous ethanol): $\lambda_{max}=258$ m$\mu$ ($\epsilon=6,580$) and 264 m$\mu$ ($\epsilon=6,550$); infrared absorption spectrum (in methylene chloride): characteristic bands at 2.95$\mu$, 5.59$\mu$, 5.69$\mu$ (shoulder), 5.78$\mu$, 5.91$\mu$, 6.06$\mu$ (shoulder) and 6.67$\mu$.

EXAMPLE 3

A mixture of 0.06 g of 3-methoxy-7$\beta$-phenylacetylamino-3-cephem-4-carboxylic acid diphenylmethyl ester and 0.05 ml of anisole and 1 ml of trifluoroacetic acid is left to stand for 5 minutes at room temperature and is then evaporated under reduced pressure. The residue is twice evaporated to dryness together with a 1:1 mixture of chloroform and toluene and is chromatographed on 5 g of silica gel (containing about 5% of water). The amorphous 3-methoxy-7$\beta$-phenylacetylamino-3-cephem-4-carboxylic acid is eluted with methylene chloride containing 30–50% of acetone and is lyophilised from dioxane. Ultraviolet absorption spectrum (in 95% strength aqueous ethanol): $\lambda_{max}=265$ m$\mu$ ($\epsilon=5,800$); infrared absorption spectrum (in methylene chloride): characteristic bands at 3.03$\mu$, 5.60$\mu$, 5.74$\mu$, 5.92$\mu$, 6.24$\mu$ and 6.67$\mu$.

3-Methoxy-7$\beta$-(D-$\alpha$-phenylglycyl-amino)-3-cephem-4-carboxylic acid can be manufactured analogously by enzymatically splitting the acetoxymethyl group in 3-acetoxymethyl-7$\beta$-(D-$\alpha$-tert.-butoxycarbonylamino-$\alpha$-phenylacetyl-amino)-3-cephem-4-carboxylic acid, esterifying the 3-hydroxymethyl-7$\beta$-(D-$\alpha$-tert.-butoxycarbonylamino-$\alpha$-phenylacetyl-amino)-3-cephem-4-carboxylic acid thus obtainable with diphenyldiazomethane and replacing the hydroxyl group in the 3-hydroxymethyl group of 3-hydroxymethyl-7$\beta$-(D-$\alpha$-tert.-butoxycarbonylamino-$\alpha$-phenylacetylamino)-3-cephem-4-carboxylic acid diphenylmethyl ester by iodine by treatment with N-methyl-N,N'-dicyclohexyl-carbodiimidium iodide; the 3-iodomethyl group in the 3-iodomethyl-7$\beta$-(D-$\alpha$-tert.-butoxycarbonylamino-$\alpha$-phenylacetylamino)-3-cephem-4-carboxylic acid diphenylmethyl ester is converted into the methylene group by reduction, for example by treatment with zinc in the presence of 90% strength aqueous acetic acid, and the 3-methylene-7$\beta$-(D-$\alpha$-tert.-butoxycarbonylamino-$\alpha$-phenylacetylamino)-cepham-4$\alpha$-carboxylic acid diphenylmethyl ester is converted into a mixture of 7$\beta$-(D-$\alpha$-tert.-butoxycarbonylamino-$\alpha$-phenylacetyl-amino)-cepham-3-one-4$\xi$-carboxylic acid diphenylmethyl ester and its 1-oxide by treatment with ozone, followed by dimethyl sulphide; the 1-oxide is removed chromatographically, the 7$\beta$-(D-$\alpha$-tert.-butoxycarbonylamino-$\alpha$-phenylacetyl-amino)-cepham-3-one-4$\epsilon$-carboxylic acid diphenylmethyl ester is treated with diazomethane and after reaction with trifluoroacetic acid in the presence of anisole, the 3-methoxy-7$\beta$-(D-$\alpha$-tert.-butoxycarbonylamino-$\alpha$-phenylacetyl-amino)-3-cephem-4-carboxylic acid diphenylmethyl ester yields the desired 3-methoxy-7$\beta$-(D-$\alpha$-phenylglycyl-amino)-3-cephem-4-carboxylic acid.

3-Methoxy-7$\beta$-(D-$\alpha$-phenylglycyl-amino)-3-cephem-4-carboxylic acid can also be obtained if in 3-methoxy-7$\beta$-phenylacetylamino-3-cephem-4-carboxylic acid diphenylmethyl ester the phenylacetylamino group is split by treatment with phosphorus pentachloride in the presence of pyridine at about $-10°$ C., followed by methanol at about $-15°$ C., and hydrolysis at a pH value of about 2, the free amino group in the 7$\beta$-amino-3-methoxy-3-cephem-4-carboxylic acid diphenylmethyl ester is acylated by treatment with the mixed anhydride of $\alpha$-tert.-butoxycarbonylamino-$\alpha$-phenylacetic acid and chloroformic acid isobutyl ester and in the 3-methoxy-7$\beta$-(D-$\alpha$-tert.-butyloxycarbonylamino-$\alpha$-phenylacetyl-amino)-3-cephem-4-carboxylic acid diphenylmethyl ester the amino group and the carboxyl group are liberated by treatment with trifluoroacetic acid in the presence of anisole.

EXAMPLE 4

An oxygen-ozone stream, containing 0.21 mmol of ozone/minute, is passed into a solution, cooled to $-70°$ C., of 5.0 g of 3-methylene-7$\beta$-(D-$\alpha$-tert.-butoxycarbonylamino-$\alpha$-phenylacetylamino)-cepham-4$\alpha$-carboxylic acid diphenylmethyl ester in 500 ml of methylene chloride, whilst stirring vigorously. After a further 10 minutes, 3 ml of dimethyl sulphide are added to the reaction mixture, which is stirred for one hour at $-65°$ C. and for 2 hours at room temperature and then evaporated under reduced pressure. The crude product, which contains the 7$\beta$-(D-$\alpha$-tert.-butoxycarbonylamino-$\alpha$-phenylacetyl-amino)-cepham-3-one-4$\xi$-carboxylic acid diphenylmethyl ester, in 150 ml of methanol, is treated with an excess amount of a solution of diazomethane in diethyl ether, stirred for 15 minutes and subsequently evaporated. A yellowish foam is obtained, which is chromatographed on 200 g of silica gel. Amorphous 3-methoxy-7$\beta$-(D-$\alpha$-tert.-butoxycarbonylamino-$\alpha$-phenylacetylamino)-3-cephem-4-carboxylic acid diphenylmethyl ester is eluted with a 3:1 mixture of toluene and ethyl acetate. Thin layer chromatogram (silica gel): Rf=0.22 (system: toluene/ethyl acetate, 3:1), infrared absorption spectrum (in methylene chloride): characteristic bands at 2.94$\mu$, 5.62$\mu$, 5.85$\mu$, 6.23$\mu$ and 6.70$\mu$.

The starting material can be manufactured as follows:

A chromatography column (diameter: 3 cm) is filled with 350 g of zinc grit, which is amalgamated for 10 minutes with an 0.1 molar solution of mercury-II chloride in 0.1 N hydrochloric acid and is washed with a large amount of water and subsequently with a small amount of 1 N hydrochloric acid. A solution of 55 g of green chromium-III chloride hexahydrate in 55 ml of water and 11 ml of 2 N sulphuric acid is poured into the reduction tube and the outlet speed is regulated so that a chromium-II chloride solution of a pure blue colour drips into the reaction vessel, which is kept under a nitrogen atmosphere. The blue chromium-II chloride solution is subsequently treated with a solution of 92 g of sodium acetate in 180 ml of air-free water, whereupon the solution assumes a red discolouration and finely crystalline chromium-II acetate precipitates. After completion of the pecipitation, the supernatant solution is removed and the chromium-II acetate is twice washed with 250 ml of air-free water at a time. A solution of 10.0 g of 3-acetoxymethyl-7$\beta$-(D-$\alpha$-tert.-butoxycarbonyl-amino-$\alpha$-phenylacetyl-amino)-3-cephem-4-carboxylic acid in 200 ml of dimethylsulphoxide is added to the moist chromium-II acetate and the reaction mixture is stirred for 15 hours under a nitrogen atmosphere at room temperature. For working up, the reaction mixture is aerated for 30 minutes and after addition of 1,000 g of a polystyrenesulphonic ion exchanger in the Na$\oplus$ form (Dowex 50 W) and 1,000 ml of water, the whole is stirred for one hour. After removing the ion exchanger, the pH value of the solution is adjusted to 2 with 6 N hydrochloric acid and the aqueous phase is extracted three times with 2,000 ml of ethyl acetate at a time. The organic extracts are washed once with 1,000 ml of a saturated aqueous sodium chloride solution, dried over magnesium sulphate and evaporated.

The resulting crude product is dissolved in 100 ml of methanol and stirred with a solution of 6 g of diphenyldiazomethane in 30 ml of benzene for 1 hour at room temperature. The crude product obtained after the evaporation is chromatographed on 500 g of silica gel; 3-methylene-7β-(D-α-tert.-butoxycarbonylamino-α-phenylacetyl-amino)-cepham-4α-carboxylic acid diphenylmethyl ester is eluted with a 4:1 mixture of petroleum ether and diethyl ether; after crystallisation from a mixture of methylene dichloride and hexane, the product melts at 156°-158° C.; $[\alpha]_D = -50 \pm 1°$ (c=0.713, chloroform); ultraviolet absorption spectrum in 95% strength aqueous ethanol): $\lambda_{max} = 258\mu$ ($\epsilon = 990$); infrared absorption spectrum (in methylene chloride): characteristic bands at 2.94μ, 5.64μ, 5.74μ, 5.88μ (shoulder) and 6.71μ.

EXAMPLE 5

A mixture of 2.44 g of 3-methoxy-7β-(D-α-tert.-butoxycarbonylamino-α-phenylacetyl-amino)-3-cephem-4-carboxylic acid diphenylmethyl ester, 2.1 ml of anisole and 41 ml of trifluoroacetic acid is left to stand for 5 minutes at room temperature and is then evaporated. The residue is taken up in 200 ml of a 3:1 mixture of toluene and chloroform, evaporated and dried in a high vacuum. The brown residue is repeatedly digested with diethyl ether, filtered off and dried. The resulting light brown pulverulent trifluoroacetic of 3-methoxy-7β-(D-α-phenylglycyl-amino)-3-cephem-4-carboxylic acid is dissolved in 5 ml of methanol, 5 ml of diethyl ether and 0.5 ml of water and the pH value of the solution is adjusted to about 4 by dropwise addition of a 3% strength solution of triethylamine in diethyl ether; thereupon a fluocculent brownish precipitate separates out. The precipitation is completed by further addition of diethyl ether and the precipitate is filtered off and reprecipitated three times from a mixture of methanol and diethyl ether. The amorphous internal salt of 3-methoxy-7β-(D-α-phenylglycyl-amino)-3-cephem-4-carboxylic acid shows an Rf value of about 0.14 in a thin layer chromatogram (silica gel) (system: ethyl acetate/n-butanol/pyridine/acetic acid/water, 42:21:21:6:10).

EXAMPLE 6

A solution of 25.7 g of 3-methylene-7β-(D-α-tert.-butoxycarbonylamino-α-phenyl-acetylamino)-cepham-4α-carboxylic acid diphenylmethyl ester in 2,500 ml of methylene chloride is cooled to $-60°$ C. and treated for 110 minutes with a stream of a mixture of oxygen and ozone, containing 0.45 mmol of ozone per minute. 8 ml of dimethyl sulphide are then added to the reaction mixture, which is stirred for one hour at $-70°$ C. and 2 hours at room temperature and is evaporated under reduced pressure. The residue is dissolved in 200 ml of methanol and the solution, containing 7β-(D-α-tert.-butoxycarbonylamino-α-phenyl-acetylamino)-cepham-3-one-4ξ-carboxylic acid diphenylmethyl ester is treated, at 0° C., with a solution of diazomethane in diethyl ether until a yellow colouration persists. After stirring for 15 minutes, the mixture is evaporated under reduced pressure and the residue is chromatographed on 1,100 g of silica gel. 3-Methoxy-7β-(D-α-tert.-butoxycarbonylamino-α-phenyl-acetylamino)-2-cephem-4α-carboxylic acid diphenylmethyl ester is eluted with diethyl ether and crystallised from a mixture of methylene chloride and pentane, melting point 166°-168° C.; $[\alpha]_D^{20} = +178° \pm 1°$ (c=0.711 in chloroform); thin layer chromatogram (silica gel; development with iodine): Rf~0.61 (system: diethyl ether); ultraviolet absorption spectrum (in ethanol): $\lambda_{max} = 257$ mμ ($\xi = 3,550$); infrared absorption spectrum (in methylene chloride): characteristic bands at 2.96μ, 5.63μ, 5.74μ, 5.85μ (shoulder), 5.92μ, 6.16μ, 6.64μ (shoulder) and 6.72μ. Further elution with diethyl ether yields amorphous 3-methoxy-7β-(D-α-tert.-butoxycarbonylamino-α-phenylacetylamino)-3-cephem-4-carboxylic acid diphenylmethyl ester which can be lyophilised from dioxane. Thin layer chromatogram (silica gel; development with iodine): Rf~0.33 (system: diethyl ether); $[\alpha]_D^{20} = 1° \pm 1°$ (c=0.98 in chloroform); ultraviolet absorption spectrum (in ethanol) $\lambda_{max} = 264\mu$ ($\epsilon = 6,300$); infrared absorption spectrum (in methylene chloride): characteristic bands at 2.94μ, 5.62μ, 5.84μ, 5.88μ (shoulder), 6.25μ and 6.71μ.

EXAMPLE 7

A mixture of 8.8 g of 3-methoxy-7β-(D-α-tert.-butoxycarbonylamino-α-phenyl-acetylamino)-3-cephem-4-carboxylic acid diphenylmethyl ester, 8.6 ml of anisole and 145 ml of trifluoroacetic acid is stirred for 15 minutes at 0° C., 400 ml of precooled toluene are then added and the mixture is evaporated under reduced pressure. The residue is dried under high vacuum, digested with diethyl ether and filtered off. The trifluoroacetate of 3-methoxy-7β-(D-α-phenyl-glycylamino)-3-cephem-4-carboxylic acid is thus obtained in pulverulent form and is dissolved in 20 ml of water. The solution is twice washed with 25 ml of ethyl acetate at a time and the pH value is adjusted to about 5 with a 20% strength triethylamine solution in methanol, whereupon a colourless precipitate forms. The mixture is stirred for one hour in an ice bath, 20 ml of acetone are then added and the whole is left to stand for 16 hours at about 4° C. The colourless precipitate is filtered off, washed with acetone and diethyl ether and dried under reduced pressure. 3-Methoxy-7β-(D-α-phenyl-glycylamino)-3-cephem-4-carboxylic acid, as the internal salt, which furthermore is in the form of a hydrate, is thus obtained in the form of a micro-crystalline powder, melting point 174°-176° C. (with decomposition); $[\alpha]_D^{20} = +149°$ (c=1.03 in 0.1 N hydrochloric acid); thin layer chromatogram (silica gel; development with iodine): Rf~0.36 (system: n-butanol/pyridine/acetic acid/water, 40:24:6:30); ultraviolet absorption spectrum (in 0.1 N aqueous sodium bicarbonate solution): $\lambda_{max} = 267\mu$ ($\epsilon = 6,200$); infrared absorption spectrum (in mineral oil): characteristic bands inter alia at 5.72μ, 5.94μ, 6.23μ and 6.60μ.

EXAMPLE 8

A mixture of 0.063 g of 3-methoxy-7β-(D-α-tert.-butoxycarbonylamino-α-phenylacetylamino)-2-cephem-4α-carboxylic acid diphenylmethyl ester, 0.1 ml of anisole and 1.5 ml of trifluoroacetic acid is left to stand for 15 minutes at 0° C. and is then evaporated under reduced pressure. The residue is digested with diethyl ether, filtered off and dried. The colourless and pulverulent trifluoroacetate of 3-methoxy-7β-(D-α-phenyl-glycylamino)-2-cephem-4α-carboxylic acid thus obtainable, is dissolved in 0.5 ml of water and the pH value of the solution is adjusted to about 5 by dropwise addition of a 10% strength solution of triethylamine in methanol. The mixture is stirred for one hour in an ice bath and the colourless precipitate is filtered off and dried in a high vacuum. 3-Methoxy-7β-(D-α-phenyl-glycylamino)-2-cephem-4α-carboxylic acid is thus obtained as an internal salt. Thin layer chromatogram (silica gel; development with iodine): Rf~0.44 (system: n-butanol/pyridine/acetic acid/water, 40:24:6:30); ultraviolet absorption spectrum (in 0.1 N aqueous sodium bicarbonate solution): $\lambda_{shoulder}=260\mu$.

EXAMPLE 9

A solution of 0.20 g of 3-chloro-perbenzoic acid in 5 ml of methylene chloride is added to a solution, cooled to 0° C., of 0.63 g of 3-methoxy-7β-(D-α-tert.-butoxycarbonylamino-α-phenyl-acetylamino)-2-cephem-4α-carboxylic acid diphenylmethyl ester in 25 ml of methylene chloride. The mixture is stirred for 30 minutes at 0° C., mixed with 50 ml of methylene chloride and successively washed with 25 ml of a saturated aqueous sodium bicarbonate solution and 25 ml of a saturated aqueous sodium chloride solution. The organic phase is dried over sodium sulphate and evaporated under reduced pressure. The residue is crystallised from a mixture of methylene chloride and diethyl ether. 3-Methoxy-7β-(D-α-tert.-butoxycarbonylamino-α-phenyl-acetylamino)-3-cephem-4-carboxylic acid diphenylmethyl ester 1-oxide is thus obtained in the form of colourless needles, melting point 172°–175° C.; thin layer chromatogram (silica gel): Rf~0.44 (system: ethyl acetate; development with iodine vapour); ultraviolet absorption spectrum (in ethanol): $\lambda_{max}=277$ mμ ($\epsilon=7,200$); infrared absorption spectrum (in methylene chloride): characteristic bands at 2.96μ, 5.56μ, 5.71μ, 5.83μ, 5.90μ, 6.27μ and 6.67μ.

EXAMPLE 10

A solution, cooled to −10° C., of 1.30 g of 3-methoxy-7β-(D-α-tert.-butoxycarbonylamino-α-phenylacetyl-amino)-3-cephem-4-carboxylic acid diphenylmethyl ester 1-oxide in 30 ml of dimethylformamide is treated with 2.80 g of phosphorus trichloride, with exclusion of air. After leaving it to stand for 15 minutes, the reaction mixture is poured out onto a mixture of ice and an aqueous dipotassium hydrogen phosphate solution; the aqueous mixture is twice extracted with 100 ml of ethyl acetate at a time. The organic extract is washed with a saturated aqueous sodium chloride solution, dried over sodium sulphate and evaporated. The residue is chromatographed on silica gel; amorphous 3-methoxy-7β-(D-α-tert.-butoxycarbonylamino-α-phenyl-acetyl-amino)-3-cephem-4-carboxylic acid diphenylmethyl ester is eluted, with diethyl ether, as a substance which is pure according to thin layer chromatography, Rf~0.39 (system: diethyl ether; development with iodine vapour); $[\alpha]_D=1°\pm1°$ (c=0.981 in chloroform); ultraviolet absorption spectrum (in ethanol): $\lambda_{max}=264\mu$ ($\epsilon=6,300$); infrared absorption spectrum (in methylene chloride): characteristic bands at 2.94μ, 5.62μ, 5.84μ, 5.88μ, 6.25μ and 6.70μ.

EXAMPLE 11

A solution of 0.050 g of 7β-phenylacetylaminocepham-3-one-4ξ-carboxylic acid diphenylmethyl ester and 0.020 g of 1-methyl-3-(4-methylphenyl)-triazene in 5 ml of benzene is boiled under reflux for 2 hours. After cooling, the mixture is evaporated under reduced pressure and the residue is purified by thin layer chromatography (silica gel; 1×20 cm; system: toluene/ethyl acetate, 3:1). The zone (Rf~0.18) which is visible under ultraviolet light ($\lambda=254\mu$) is eluted with acetone and 3-methoxy-7β-phenylacetylamino-3-cephem-4-carboxylic acid diphenylmethyl ester is obtained, ultraviolet absorption spectrum (in ethanol): $\lambda_{max}=264\mu$ ($\epsilon=6,300$); infrared absorption spectrum (in methylene chloride): characteristic bands at 2.94μ, 5.63μ, 5.83μ, 5.94μ, 6.26μ and 6.68μ.

The starting material can be manufactured as follows:

A solution of 0.50 g of 3-methylene-7β-phenylacetylamino-cepham-4α-carboxylic acid diphenylmethyl ester in 100 ml of methanol is treated for 6.5 minutes at −70° C. with an oxygen-ozone stream containing 0.175 mmol of ozone/minute. The reaction mixture is mixed with 0.5 ml of dimethyl sulphide and stirred for one hour at −70° C., then for 2 hours at room temperature and evaporated to dryness. The residue, in methylene chloride is chromatographed on 15 g of silica gel. Elution with methylene chloride yields amorphous 7β-phenylacetylaminocepham-3-one-4ξ-carboxylic acid diphenylmethyl ester, thin layer chromatography (silica gel): Rf~0.47 (system: toluene/acetone/methanol/acetic acid, 80:10:5:5); infrared absorption spectrum (in methylene chloride): characteristic bands at 2.95μ, 5.61μ, 5.77μ, 5.85μ, 5.95μ, 6.21μ and 6.87μ; the compound shows a positive reaction with iron-III chloride.

EXAMPLE 12

A solution of 0.50 g of the 4-methylphenylsulphonate of 7β-amino-cepham-3-one-4ξ-carboxylic acid diphenylmethyl ester, which is predominantly present in the enol form, that is to say as the 4-methylphenylsulphonate of 7β-amino-3-cephem-3-ol-4-carboxylic acid diphenylmethyl ester, in 25 ml of methanol, is treated, at 0° C. with a solution of diazomethane in diethyl ether until the yellow colouration persists. The mixture is stirred for 10 minutes in an ice bath and is then evaporated. The residue is chromatographed on silica gel. Oily 7β-dimethylamino-3-methoxy-3-cephem-4-carboxylic acid diphenylmethyl ester is eluted with a 2:1 mixture of toluene and ethyl acetate, thin layer chromatogram (silica gel; development with iodine vapour): Rf~0.39 (system: ethyl acetate); ultraviolet absorption spectrum (in ethanol): $\lambda_{max}=265\mu$ ($\epsilon=6,100$); infrared absorption spectrum (in methylene chloride): characteristic bands at 3.33μ, 5.63μ, 5.81μ and 6.23μ.

Further elution with ethyl acetate yields oily 7β-amino-3-methoxy-3-cephem-4-carboxylic acid diphenylmethyl ester, thin layer chromatogram (silica gel; development with iodine vapour): Rf~0.20 (system: ethyl acetate); ultraviolet absorption spectrum (in ethanol): $\lambda_{max}=265\mu$ ($\epsilon=5,900$); infrared absorption spectrum (in methylene chloride): characteristic bands at 2.98μ, 3.33μ, 5.62μ, 5.81μ and 6.24μ.

The starting material can be manufactured as follows:

A solution, cooled to −15° C., of 2.0 g of 3-methylene-7β-phenylacetylamino-cepham-4α-carboxylic acid diphenylmethyl ester in 80 ml of absolute methylene chloride is mixed with 3.2 ml of absolute pyridine and 32 ml of an 8% strength solution of phosphorus pentachloride in methylene chloride and stirred for one hour under a nitrogen atmosphere at a temperature between −10° C. and −5° C. The reaction mixture is then cooled to −25° C., mixed with 25 ml of absolute methanol and stirred for one hour at −10° C. and then for 1.5 hours at room temperature. 80 ml of an 0.5 molar aqueous solution of potassium dihydrogen phosphate are then added, the pH value is adjusted to 2 with 20% strength aqueous phosphoric acid and the mixture is stirred for 30 minutes at room temperature.

The organic phase is separated off; the aqueous phase is twice re-extracted with 150 ml of methylene chloride at a time and the organic solutions are combined, dried over sodium sulphate and evaporated. The oily residue is taken up in 25 ml of ethyl acetate and a solution of 1.14 g of 4-methylphenylsulphonic acid monohydrate in 25 ml of ethyl acetate is added at 0° C. A voluminous precipitate separates out, which is filtered off, rinsed with cold ethyl acetate and diethyl ether, dried and recrystallised, from a mixture of methylene chloride and diethyl ether. The 4-methylphenylsulphonate of 7β-amino-3-methylenecepham-4α-carboxylic acid diphenylmethyl ester is thus obtained in the form of colourless needles, melting point 153°–155° C.; $[\alpha]_D = -14° \pm 1°$ (c=0.97 in methanol); ultraviolet absorption spectrum (in ethanol): $\lambda_{max} = 257\mu$ ($\epsilon = 1,500$); infrared absorption spectrum (in methylene chloride): characteristic bands at 3.5μ, 5.60μ, 5.73μ, 8.50μ, 9.68μ and 9.92μ.

A stream of oxygen and ozone (containing 0.35 mmol of ozone per minute) is passed for 4 minutes through a solution, cooled to −60° C., of 0.553 g of the 4-methylphenylsulphonate of 7β-amino-3-methylene-cepham-4α-carboxylic acid diphenylmethyl ester in 50 ml of methanol. After a further 5 minutes, the pale blue-coloured solution is treated with 0.3 ml of dimethyl sulphide. The mixture is stirred for 15 minutes at −70° C., for one hour at −12° C. and for one hour in an ice bath and is then evaporated. The residue is taken up in a small amount of methylene chloride, diethyl ether is then added until the mixture turns cloudy, and the mixture is left to stand. The microcrystalline, reddish-coloured pulverulent precipitate is filtered off and yields the 4-methylphenylsulphonate of 7β-amino-cepham-3-one-4ξ-carboxylic acid diphenylmethyl ester which is mainly present in the enol form as the 4-methylphenylsulphonate of 7β-amino-3-cephem-3-ol-4-carboxylic acid diphenylmethyl ester, melting point=143°–145° C. (with decomposition); thin layer chromatogram (silica gel) Rf∼0.28 (system: ethyl acetate/pyridine/water, 85:10:5); ultraviolet absorption spectrum (in ethanol): $\lambda_{max} = 262$ mμ ($\epsilon = 3,050$) and 282 mμ ($\epsilon = 3,020$); infrared absorption spectrum (in methylene chloride): characteristic bands at 5.58μ, 5.77μ (shoulder), 6.02μ and 6.22μ.

EXAMPLE 13

A solution, cooled to 0° C., of 2.0 g of 7β-phenylacetylamino-cepham-3-one-4ξ-carboxylic acid diphenylmethyl ester in 75 ml of methanol is treated with excess diazo-n-butane in diethyl ether. The mixture is stirred for 15 minutes at 0° C. and is then evaporated under reduced pressure. The oily residue is purified by means of preparative thin layer chromatography (silica gel plates, 6×100 cm; system: toluene/ethyl acetate, 3:1). The layer which is visible under ultraviolet light (λ=254 mμ) is removed and in each case eluted with acetone. This zone (Rf∼0.33) yields 3-n-butoxy-7β-phenylacetylamino-3-cephem-4-carboxylic acid diphenylmethyl ester which after crystallisation from a mixture of methylene chloride and diethyl ether is in the form of colourless flakes which melt at 168°–170° C., $[\alpha]_D^{20} = +55° \pm 1°$ (c=0.38 in chloroform); ultraviolet absorption spectrum (in 95% strength aqueous ethanol): $\lambda_{max} = 264$ mμ ($\epsilon = 7,300$); infrared absorption spectrum (in methylene chloride): characteristic bands at 2.98μ, 5.62μ, 5.81μ, 5.92μ, 6.25μ and 6.62μ.

EXAMPLE 14

A mixture of 5 g of 3-methylene-7β-(D-α-tert.-butoxycarbonylamino-α-phenylacetylamino)-cepham-4α-carboxylic acid diphenylmethyl ester and 500 ml of methylene chloride is treated, at −70° C., with 1.15 equivalents of ozone according to the process described in the preceding examples, 2 ml of dimethylsulphide are subsequently added and the mixture is stirred for one hour at −70° C. and 2 hours at room temperature and is then evaporated under reduced pressure. The residue, containing 7β-(D-α-tert.butoxycarbonylamino-α-phenylacetylamino)-cepham-3-one-4ξ-carboxylic acid diphenylmethyl ester, is dissolved in 150 ml of methanol and a solution of diazo-n-butane in diethyl ether is added at 0° C. until the yellow colouration persists. After 15 minutes, the solution is evaporated under reduced pressure and the residue is purified by means of preparative thin layer chromatography (silica gel; 1.5 mm thickness; plates of size 16×100 cm; system: toluene/ethyl acetate, 72:25). The zone which is visible under ultraviolet light, and has an Rf value of about 0.35, yields 3-n-butoxy-7β-(D-α-tert.-butoxycarbonylamino-α-phenylacetylamino)-3-cephem-4-carboxylic acid diphenylmethyl ester, which is again purified by renewed chromatography on silica gel and is lyophilised from dioxane, $[\alpha]_D^{20} = +11° \pm 1°$ (c=0.98 in chloroform); ultraviolet absorption spectrum (in 95% strength aqueous ethanol): $\lambda_{max} = 264$ mμ ($\epsilon = 6,100$); infrared absorption spectrum (in methylene chloride): characteristic bands at 2.88μ, 5.63μ, 5.84μ (shoulder), 5.88μ, 6.26μ and 6.71μ.

EXAMPLE 15

A mixture of 0.5 g of 3-n-butoxy-7β-(D-α-tert.-butoxycarbonylamino-α-phenylacetylamino)-3-cephem-4-carboxylic acid diphenylmethyl ester, 1 ml of anisole and 15 ml of trifluoroacetic acid is left to stand for 15 minutes at 0° C. and is then diluted with 200 ml of cold toluene and evaporated under reduced pressure. The residue is stirred with diethyl ether and the pulverulent colourless residue is filtered off, washed with diethyl ether and dried under a high vacuum. The trifluoroacetate salt of 3-n-butoxy-7β-(D-α-phenyl-glycylamino)-3-cephem-4-carboxylic acid is thus obtained, and is dissolved in 5 ml of water. The solution is twice washed with 10 ml of ethyl acetate at a time and the pH value of the aqueous phase is adjusted to 5.0 by adding a solution of triethylamine in methanol. Thereafter the solution is evaporated under reduced pressure; the residue is taken up in a small amount of acetone and is diluted with diethyl ether until the mixture is turbid. The 3-n-butoxy-7β-(D-α-phenyl-glycylamino)-3-cephem-4-carboxylic acid, which is present in the form of the internal salt, is obtained as a crystalline precipitate and filtered off, melting point 141°–142° C.; thin layer chromatogram (silica gel): Rf∼0.21 (system: ethyl acetate/pyridine/acetic acid/water, 62:21:6:11); ultraviolet absorption spectrum (in 0.1 N aqueous sodium bicarbonate solution): $\lambda_{max} = 267$ mμ ($\epsilon = 7,300$).

EXAMPLE 16

A solution of 0.258 g of 3-methylene-7β-phenylacetylamino-cepham-4α-carboxylic acid diphenylmethyl ester 1-oxide in 50 ml of methanol is treated with an oxygen/ozone mixture (20 mmols of ozone per minute) at −65° C. until the blue colouration persists. The reaction mixture is thereafter treated with 0.5 ml of dimethylsulphide, stirred for 20 minutes at −65° C. and 30 minutes at room temperature and evaporated under reduced pressure. The residue, containing 7β-phenylacetylamino-cepham-3-one-4ξ-carboxylic acid diphenylmethyl ester 1-oxide is taken up in 20 ml of methanol and treated, at 0° C., with an ethereal solution of diazomethane in diethyl ether until the yellow colouration persists. After standing for 15 minutes, the reaction mixture is evaporated under reduced pressure. The residue is purified by means of preparative thin layer chromatography; the zone which is visible under ultraviolet light ($\lambda=254$ mμ), of Rf~0.20 (system: ethyl acetate; identification with iodine) is eluted with a 1:1 mixture of acetone and methanol and 3-methoxy-7β-phenylacetylamino-3-cephem-4-carboxylic acid diphenylmethyl ester 1-oxide is thus obtained, ultraviolet absorption spectrum (in 95% strength aqueous ethanol): $\lambda_{max}=276$ mμ ($\epsilon=7,500$); infrared absorption spectrum (in methylene chloride): characteristic bands at 2.94μ, 5.56μ, 5.81μ, 5.92μ, 6.22μ and 6.67μ.

3-Methoxy-7β-phenylacetylamino-3-cephem-4-carboxylic acid methyl ester is obtained analogously, melting point 171°-174° C. after recrystallisation from methylene chloride and hexane; $[\alpha]_D^{20}=+102°\pm1°$ (c=0.95 in chloroform); ultraviolet absorption spectrum (in 95% strength aqueous ethanol): $\lambda_{max}=265$ mμ ($\epsilon=6,250$); infrared absorption spectrum (in methylene chloride): characteristic bands at 2.94μ, 5.62μ, 5.76μ, 5.93μ, 6.24μ and 6.65μ.

The starting material used in the above example can be manufactured as follows: a solution, cooled to 0° C., of 0.50 g of 3-methylene-7β-phenylacetylamino-cepham-4α-carboxylic acid diphenylmethyl ester in 50 ml of methylene chloride is mixed with a solution of 0.19 g of 3-chloroperbenzoic acid in 10 ml of methylene chloride and the mixture is stirred for 30 minutes in an ice bath under a nitrogen atmosphere. The reaction mixture is diluted with 100 ml of methylene chloride, washed twice with 50 ml of a saturated aqueous sodium bicarbonate solution and with 50 ml of a saturated aqueous sodium chloride solution, dried over sodium sulphate and evaporated under reduced pressure. The residue is chromatographed on 50 g of silica gel. 3-Methylene-7β-phenylacetylaminocepham-4α-carboxylic acid diphenylmethyl ester 1-oxide is eluted with methylene chloride, containing 3-5% of acetone, and crystallised from a mixture of acetone, diethyl ether and hexane, melting point=172°-175° C.; $[\alpha]_D^{20}=-68°$ (c=0.925 in chloroform); thin layer chromatogram (silica gel; identification with iodine): Rf~0.25 (system: toluene/ethyl acetate, 1:1); ultraviolet absorption spectrum (in 95% strength aqueous ethanol): no specific absorption; infrared absorption spectrum (in methylene chloride): characteristic bands at 2.96μ, 5.60μ, 5.74μ, 5.92μ, 6.24μ, 6.63μ and 9.60μ.

EXAMPLE 17

A solution of 0.2 g of 3-methoxy-7β-phenylacetylamino-3-cephem-4-carboxylic acid in 10 ml of methanol is treated with a solution of diazomethane in diethyl ether until the yellow colouration persists and is then evaporated under reduced pressure. The residue is chromatographed on silica gel. 3-Methoxy-7β-phenylacetylamino-3-cephem-4-carboxylic acid methyl ester is eluted with a 3:1 mixture of toluene and ethyl acetate and recrystallised from a mixture of methylene chloride and hexane, melting point 171°-174° C.; $[\alpha]_d^{20}=+102°\pm1°$ (c=0.95 in chloroform); ultraviolet absorption spectrum (in 95% strength aqueous ethanol): $\lambda_{max}=265$ mμ ($\epsilon=6,250$); infrared absorption spectrum (in methylene chloride): characteristic bands at 2.94μ, 5.62μ, 5.76μ, 5.93μ, 6.24μ and 6.65μ.

EXAMPLE 18

A mixture of 0.02 g of crude 7β-(D-α-tert.-butoxycarbonylamino-α-phenylacetylamino)-cepham-3-one-4ξ-carboxylic acid diphenylmethyl ester and 2 ml of acetone is treated with 0.1 ml of dimethyl sulphate and 0.005 g of anhydrous potassium carbonate and stirred for 16 hours under a nitrogen atmosphere, at room temperature. The reaction mixture is evaporated under reduced pressure, the residue is taken up in methylene chloride, and the solution is washed with a saturated aqueous sodium chloride solution, dried over sodium sulphate and evaporated under reduced pressure. The residue is purified by preparative layer chromatography (silica gel). The two zones which are visible under ultraviolet light ($\lambda=254$ mμ) are isolated. At Rf~0.61 (silica gel; system: diethyl ether), 3-methoxy-7β-(D-α-tert.-butoxycarbonylamino-α-phenylacetylamino)-2-cephem-4α-carboxylic acid diphenylmethyl ester, melting point 166°-168° C. after recrystallisation from a mixture of methylene chloride and pentane, is obtained; at Rf~0.31 (silica gel; system: diethyl ether), amorphous 3-methoxy-7β-(D-α-tert.-butoxycarbonylamino-α-phenylacetylamino)-3-cephem-4-carboxylic acid diphenylmethyl ester is obtained.

EXAMPLE 19

A solution, cooled to −70° C., of 8.2 g of 7β-(D-α-tert.-butoxycarbonylamino-α-phenylacetylamino)-3-methylene-cepham-4α-carboxylic acid diphenylmethyl ester in 800 ml of methylene chloride is treated for 34 minutes with a stream of oxygen/ozone (0.49 mmol of ozone per minute), and is then treated with 3.5 ml of dimethylsulphide and stirred for one hour at −70° C. and for 2 hours at room temperature. After evaporation under reduced pressure, the oily residue containing the 7β-(D-α-tert.-butoxycarbonylamino-α-phenylacetylamino)-cepham-3-one-4ξ-carboxylic acid diphenylmethyl ester is dissolved in 300 ml of benzene, 3.28 g of 1-ethyl-3-(4-methylphenyl)-triazene are added and the whole is boiled for one hour under reflux in a nitrogen atmosphere and is then evaporated under reduced pressure. The residue is chromatographed on 360 g of silica gel. The amorphous 3-ethoxy-7β-(D-α-tert.-butoxycarbonylamino-α-phenylacetylamino)-3-cephem-4-carboxylic acid diphenylmethyl ester is eluted with a 4:1 mixture of toluene and ethyl acetate, thin layer chromatography (silica gel): Rf~0.28 (system: toluene/ethyl acetate, 3:1); ultraviolet absorption spectrum (in 95% strength aqueous ethanol): $\lambda_{max}=258$ mμ ($\epsilon=7,000$) and $\lambda_{max}264$ mμ ($\epsilon=6,900$); infrared absorption spectrum (in methylene chloride): characteristic bands at 2.96μ, 5.64μ, 5.90μ, 6.28μ and 6.73μ.

EXAMPLE 20

A mixture of 2.70 g of 3-ethoxy-7β-(D-α-tert.-butoxycarbonylamino-α-phenylacetylamino)-3-cephem-4-carboxylic acid diphenylmethyl ester, 6.7 ml of anisole and 67 ml of formic acid is stirred for one hour at room temperature, diluted with 200 ml of toluene and then evaporated under reduced pressure, and the residue is dried under a high vacuum, digested with diethyl ether and filtered off. The formate of 3-ethoxy-7β-(D-α-phenyl-glycylamino)-3-cephem-4-carboxylic acid, which is obtained as a brownish powder, is dissolved in 8 ml of water and the aqueous phase is acidified with 2 N aqueous hydrochloric acid, washed with 10 ml of ethyl acetate, adjusted to a pH value of about 5 with a 10% strength solution of triethylamine in methanol and evaporated under reduced pressure. The residue is taken up in a small amount of methanol and the amorphous light yellowish 3-ethoxy-7β-(D-α-phenyl-glycylamino)-3-cephem-4-carboxylic acid is precipitated as the internal salt by addition of methylene chloride and diethyl ether; thin layer chromatogram (silica gel): Rf∼0.17 (system: ethyl acetate/pyridine/acetic acid/water, 62:21:6:11); ultraviolet absorption spectrum (in 0.1 molar aqueous sodium bicarbonate solution): $\lambda=263$ mµ ($\epsilon=5,500$).

EXAMPLE 21

A solution of 15 g of 3-methylene-7β-(D-α-tert.-butoxycarbonylamino-α-phenylacetylamino)-cepham-4α-carboxylic acid diphenylmethyl ester in 1,500 ml of methylene chloride is treated for 62 minutes, at −65° C., with a mixture of oxygen and ozone, containing 0.5 mmol of ozone per minute, and is then mixed with 8.7 ml of dimethylsulphide at −70° C. The mixture is stirred for 1 hour at −70° C. and for 2 hours at room temperature and is evaporated under reduced pressure. The residue, containing the crude 7β-(D-α-tert.-butoxycarbonylamino-α-phenylacetylamino)-cepham-3-one-4ξ-carboxylic acid diphenylmethyl ester, is dissolved in 350 ml of benzene, 11 g of 1-benzyl-3-(4-methylphenyl)-triazene are added and the whole is then boiled for 4 hours under reflux. After cooling, it is washed with 100 ml of 2 N aqueous hydrochloric acid and with a saturated aqueous sodium chloride solution; the organic phase is dried over sodium sulphate and evaporated under reduced pressure. The residue is chromatographed on 650 g of silica gel; with toluene, containing 15% of ethyl acetate, amorphous 3-benzyloxy-7β-(D-α-tert.-butoxycarbonylamino-α-phenylacetylamino)-3-cephem-4-carboxylic acid diphenylmethyl ester, which according to thin layer chromatography is a single substance, is eluted; thin layer chromatogram (silica gel; development with iodine): Rf∼0.34 (system: toluene/ethyl acetate 3:1); $[\alpha]_D^{20}=+7°\pm1°$ (c=0.97 in chloroform); ultraviolet absorption spectrum (in 95% strength aqueous ethanol): $\lambda_{max}=258$ mµ ($\epsilon=6,800$), and 264 mµ ($\epsilon=6,800$), and $\lambda_{shoulder}=280$ mµ ($\epsilon=6,300$); infrared absorption spectrum (in methylene chloride): characteristic bands at 2.96µ, 5.63µ, 5.88µ, 6.26µ and 6.72µ.

EXAMPLE 22

A mixture of 4.6 g of 3-benzyloxy-7β-(D-α-tert.-butoxycarbonylamino-α-phenylacetylamino)-3-cephem-4-carboxylic acid diphenylmethyl ester, 10 ml of anisole and 100 ml of trifluoroacetic acid is stirred for 15 minutes at 0° C., then diluted with 250 ml of pre-cooled toluene and evaporated under reduced pressure, and the residue is dried in a high vacuum. The product is stirred with diethyl ether and the pulverulent trifluoroacetate of 3-benzyloxy-7β-(D-α-phenyl-glycylamino)-3-cephem-4-carboxylic acid is thus obtained; this is filtered off and dissolved in a 9:1 mixture of water and methanol. The pH value is adjusted to 1.7 with 2 N aqueous hydrochloric acid; the mixture is twice washed with 30 ml of ethyl acetate at a time (the organic wash solutions are discarded) and the pH value of the aqueous phase is adjusted to 5 by addition of a 10% strength solution of triethylamine in methanol. The aqueous phase is evaporated under reduced pressure, the residue is stirred with a mixture of acetone and diethyl ether, and the pulverulent product is filtered off and rinsed with acetone and with diethyl ether. 3-Benzyloxy-7β-(D-α-phenyl-glycylamino)-3-cephem-4-carboxylic acid is thus obtained in the form of a zwitter-ion, thin layer chromatogram (silica gel): Rf=0.17 (system: ethyl acetate/pyridine/acetic acid/water, 62:21:6:11); ultraviolet absorption spectrum (in 0.1 N aqueous sodium bicarbonate solution): $\lambda_{max}=266$ mµ ($\epsilon=6,500$).

EXAMPLE 23

A solution of 0.514 g of 3-methoxy-7β-phenylacetylamino-3-cephem-4-carboxylic acid diphenylmethyl ester in 30 ml of methylene chloride is cooled to −10° C. and 0.8 ml of absolute pyridine and 8.0 ml of an 8% strength solution of phosphorus pentachloride in methylene chloride are added. The reaction mixture is stirred for one hour at −10° C. to −5° C. and is then cooled to −30° C., and 5 ml of methanol are added. The whole is stirred for one hour at −10° C. to −5° C., one hour at 0° C. and one hour at room temperature. 20 ml of an 0.5 molar aqueous potassium dihydrogen phosphate solution are added, the mixture is stirred at pH 2.4 for 30 minutes and diluted with methylene chloride and the aqueous phase is separated off and extracted with methylene chloride. The combined organic phases are washed with a saturated aqueous sodium chloride solution, dried over sodium sulphate and evaporated under reduced pressure. The residue is digested with diethyl ether and left to stand for 16 hours at 0° C.; the precipitate is filtered off, washed with diethyl ether and dried. 7β-Amino-3-methoxy-3-cephem-4-carboxylic acid diphenylmethyl ester is obtained as a light beige powder, thin layer chromatogram (silica gel; developing with iodine vapour): Rf∼0.17 (system: ethyl acetate); ultraviolet absorption spectrum (in 95% strength aqueous ethanol): $\lambda_{max}=258$ mµ ($\epsilon=5,250$) and 264 mµ ($\epsilon=5,300$), and $\lambda_{shoulder}=290$ mµ ($\epsilon=5,200$); infrared absorption spectrum (in dioxane): characteristic bands at 287µ (broad), 5.62µ, 5.85µ and 6.26µ.

EXAMPLE 24

A suspension of 0.250 g of 7β-amino-3-methoxy-3-cephem-4-carboxylic acid diphenylmethyl ester in 25 ml of methylene chloride is treated with 1 ml of pyridine and 0.5 ml of phenylacetic acid chloride at 0° C. under a nitrogen atmosphere and stirred for 30 minutes at this temperature. The reaction mixture is evaporated under reduced pressure; the residue is stirred for 10 minutes with 20 ml of a 1:1 mixture of dioxane and water and the mixture is diluted with methylene chloride. The aqueous phase is separated off and extracted with methylene chloride. The combined organic phases are washed with a saturated aqueous sodium bicarbonate solution and a saturated aqueous sodium chloride solution, dried over sodium sulphate and evaporated under reduced pressure. The crude product is purified by means of preparative thin layer chromatography, using a 1:1 mixture of toluene and ethyl acetate as the solvent. The zone visible under ultraviolet light of $\lambda=254$ mµ (Rf∼0.35) is eluted with a 4:1 mixture of acetone and methanol and yields 3-methoxy-7β-phenylacetylamino-3-cephem-4-carboxylic acid diphenylmethyl ester, which is identical with the product obtainable according to the process of Example 1.

EXAMPLE 25

A solution of 1.59 g of 7β-(5-benzoylamino-5-diphenylmethoxycarbonyl-valeryl-amino)-3-methylene-cepham-4α-carboxylic acid diphenylmethyl ester in 150 ml of methylene chloride is cooled to −70° C. and treated for 12 minutes and 43 seconds, whilst stirring vigorously, with a mixture of oxone and oxygen, containing 0.2 mmol of ozone per minute, and then with 1 ml of dimethylsulphide. The mixture is stirred for 5 minutes at −70° C. and for 30 minutes at room temperature and is evaporated under reduced pressure. The residue, containing 7β-(5-benzoylamino-5-diphenylmethoxycarbonyl-valeryl-amino)-cepham-3-one-4ξ-carboxylic acid diphenylmethyl ester, is dissolved in 40 ml of methanol, cooled in an ice bath, and treated with a solution of diazomethane in diethyl ether until the yellow colouration persists. The reaction mixture is evaporated under reduced pressure and the residue is chromatographed on 100 g of silica gel. 7β-(5-Benzoylamino-5-diphenylmethoxycarbonyl-valeryl-amino)-3-methoxy-3-cephem-4-carboxylic acid diphenylmethyl ester is eluted with a 1:1 mixture of toluene and ethyl acetate and obtained as an amorphous product, thin layer chromatogram (silica gel): Rf=0.45 (system: toluene/ethyl acetate, 1:1); ultraviolet absorption spectrum (in 95% strength aqueous ethanol): $\lambda_{shoulder}$=258 mμ (ε=7,450), 264 mμ (ε=7,050) and 268 mμ (ε=6,700); infrared absorption spectrum (in methylene chloride): characteristic bands at 5.65μ, 5.78μ, 6.03μ and 6.64μ.

The starting material can be manufactured as follows:

A solution of 50 g of the sodium salt of cephalosporin C in 1,500 ml of 10% strength aqueous dipotassium hydrogen phosphate is diluted with 1,200 ml of acetone and 21 g of benzoyl chloride are added at 0° C. The mixture is stirred for 30 minutes at 0° C. and for 45 minutes at 20° C., whilst keeping the pH value constant at 8.5 by addition of a 50% strength aqueous tripotassium phosphate solution. It is concentrated to about half its volume under reduced pressure, washed with ethyl acetate, acidified to pH 2.0 with 20% strength aqueous phosphoric acid and extracted with ethyl acetate. The organic phase is dried and evaporated under reduced pressure; the residue, recrystallised from acetone, yields N-benzoyl-cephalosporin C, melting point 117°–119° C.; thin layer chromatogram (silica gel): Rf=0.37 (system: n-butanol/acetic acid/water, 75:7.5:21) and Rf: 0.08 (system: ethyl acetate/pyridine/acetic acid/water, 62:21:6:11).

A solution of 4.7 g of N-benzoyl-cephalosporin C in 85 ml of 0.5 M molar aqueous dipotassium hydrogen phosphate solution and 9 ml of dimethylformamide is stirred with 4.7 g of aluminium amalgam for 45 minutes at pH 6.0 and 45° C., whilst keeping the pH value constant by addition of 20% strength aqueous phosphoric acid. 100 ml of ice are added, and the mixture is covered with cold ethyl acetate and adjusted to pH 2.0 with concentrated phosphoric acid. The mixture is saturated with sodium chloride, the organic phase is separated off and the aqueous phase is twice rinsed with ethyl acetate.

The combined organic extracts are washed with saturated aqueous sodium chloride solution and dried over sodium sulphate and on evaporation under reduced pressure yield a residue which is caused to crystallise in ethyl acetate. It is slowly diluted with 15 ml of a 2:3 mixture of ethyl acetate and hexane and filtered after standing for 2 hours at −5° C., and after crystallisation from a 1:4 mixture of ethyl acetate and diethyl ether, 7β-(5-benzoylamino-5-carboxy-valerylamino)-3-methylene-cepham-4α-carboxylic acid is obtained, melting point 82°–89° C. (with decomposition); thin layer chromatogram (silica gel): Rf=0.53 (system: n-butanol/acetic acid/water, 75:7.5:21), and Rf=0.08 (system: ethyl acetate/pyridine/acetic acid/water, 62:21:6:11).

The aluminium amalgam used above can be manufactured as follows: a mixture of 3.3 g of aluminium grit and 100 ml of 50% strength aqueous sodium hydroxide solution is shaken for 30 seconds and after decanting the supernatant liquid the aluminium is washed three times with 300 ml of water at a time. The residue is treated for 3 minutes with 130 ml of an 0.3% strength aqueous mercury-II chloride solution and is washed three times with 300 ml of water at a time. The entire treatment is repeated once and the aluminium amalgam is finally washed three times with tetrahydrofurane. About 15 ml of ethyl acetate are used to transfer the product into the reaction vessel.

A solution of 2.3 g of 7β-(5-benzoylamino-5-carboxy-valeryl-amino)-3-methylene-cepham-4α-carboxylic acid in 25 ml of dioxane is treated dropwise, over the course of 10 minutes, with a solution of 2.5 g of diphenyldiazomethane in 10 ml of n-pentane. It is stirred for 30 minutes at room temperature, the excess diphenyldiazomethane is decomposed by adding a few drops of acetic acid (glacial acetic acid) and the solution is evaporated under reduced pressure. The residue is chromatographed on 80 g of silica gel, 7β-(5-benzoylamino-5-diphenylmethoxycarbonyl-valeryl-amino)-3-methylene-cepham-4α-carboxylic acid diphenylmethyl ester being eluted with a 3:1 mixture of toluene and ethyl acetate and then crystallised from a mixture of methyl acetate and cyclohexane, melting point 180°–181° C.; thin layer chromatogram (silica gel): Rf=0.24 (system: toluene/ethyl acetate, 2:1); ultraviolet absorption spectrum (in 95% strength aqueous ethanol): no characteristic bands; infrared absorption spectrum (in methylene chloride): characteristic bands at 5.66μ, 5.76μ, 5.95μ, 6.03μ, 6.64μ and 6.70μ.

EXAMPLE 26

A solution of 0.263 g of 7β-(5-benzoylamino-5-diphenylmethoxycarbonyl-valeryl-amino)-3-methoxy-3-cepham-4-carboxylic acid diphenylmethyl ester in 13 ml of methylene chloride is cooled to −10° C. and 0.132 ml of pyridine and 3.52 ml of an 8% strength solution of phosphorus pentachloride in methylene chloride are added. The mixture is stirred for one hour at −10° C. and is then cooled to −30° C., 2.2 ml of methanol cooled to −30° C. are added rapidly and the whole is stirred further for 30 minutes at −10° C. and 30 minutes at −5° C. Thereafter, 6.5 ml of an 0.5 molar aqueous solution of potassium dihydrogen phosphate are added to the reaction mixture, which is stirred for 5 minutes at room temperature, and the phases are separated. The aqueous phase is washed with methylene chloride; the combined methylene chloride phases are washed with concentrated aqueous sodium chloride solution, dried over sodium sulphate and evaporated under reduced pressure. The residue is dissolved in methanol and the solution is treated with diethyl ether until it is slightly turbid. 7β-Amino-3-methoxy-3-cephem-4-carboxylic acid diphenylmethyl ester is thus obtained as an amorphous precipitate, thin layer chromatogram (silica gel):

Rf=0.17 (system: ethyl acetate; development with iodine): ultraviolet absorption spectrum (in 95% strength aqueous ethanol): $\lambda_{max}=258$ mµ ($\epsilon=5,700$); infrared absorption spectrum (in dioxane): characteristic bands at 2.87µ, 5.62µ, 5.85µ and 6.26µ.

EXAMPLE 27

A solution, cooled to 0° C., and 0.400 g of 7β-(D-α-tert.-butoxycarbonylamino-α-phenylacetylamino)-3-methylene-cepham-4α-carboxylic acid diphenylmethyl ester in 40 ml of methylene chloride is treated for 3.6 minutes with an ozone-oxygen mixture containing 0.21 mmol of ozone per minute, and is then mixed with 0.5 ml of dimethylsulphide and subsequently evaporated under reduced pressure. The residue, containing 7β-(D-α-tert.-butoxycarbonylamino-α-phenylacetylamino)-cepham-3-one -4ξ-carboxylic acid diphenylmethyl ester, is dissolved in 10 ml of methanol and treated with a solution of diazomethane in diethyl ether until the yellow colouration persists. The mixture is evaporated under reduced pressure and the residue is subjected to preparative layer chromatography (silica gel; system: toluene/ethyl acetate, 1:1, identification with ultraviolet light, λ=2.54). A mixture of 7β-(D-α-tert.-butoxycarbonylamino-α-phenylacetylamino)-3-methylene-cepham-4α-carboxylic acid diphenylmethyl ester and of 7β-(D-α-tert.-butoxycarbonylamino-α-phenylacetylamino)-3-methoxy-2-cephem-4α-carboxylic acid diphenylmethyl ester, both of Rf value 0.55, is thus obtained, followed by 7β-(D-α-tert.-butoxycarbonylamino-α-phenylacetylamino)-3-methoxy-3-cephem-4-carboxylic acid diphenylmethyl ester of Rf value 0.45 and finally by a mixture of 7β-(D-α-tert.-butoxycarbonylamino-α-phenylacetylamino)-3-methoxy-3-cephem-4-carboxylic acid diphenylmethyl ester 1β-oxide of Rf value 0.17 and 1α-oxide of Rf value 0.07.

Instead of 7β-(D-α-tert.-butoxycarbonylamino-α-phenylacetylamino)-3-methylene-cepham-4α-carboxylic acid diphenylmethyl ester it is possible to use, as starting substances in the above process, 7β-(D-α-tert.-butoxycarbonylamino-α-phenylacetylamino)-3-methylene-cepham-4α-carboxylic acid 4-nitrobenzyl ester or 7β-(D-α-tert.-butoxycarbonylamino-α-phenylacetylamino)-3-methylene-cepham-4α-carboxylic acid 2,2,2-trichloroethyl ester, which can be respectively obtained by treatment of the sodium salt of 7β-(D-α-tert.-butoxycarbonylamino-α-phenylacetylamino)-3-methylene-cepham-4α-carboxylic acid with 4-nitrobenzyl bromide or of a reactive mixed anhydride of 7β-(D-α-tert.-butoxycarbonylamino-α-phenylacetylamino)-3-methylene-cephem-4α-carboxylic acid with 2,2,2-trichloroethanol, and from these starting substances to obtain, via 7β-(D-α-tert.-butoxycarbonylamino-α-phenylacetylamino)-cepham-3-one-4ξ-carboxylic acid 4-nitrobenzyl ester and 7β-(D-α-tert.-butoxycarbonylamino-α-phenylacetylamino)-cepham-3-one-4ξ-carboxylic acid 2,2,2-trichloroethyl ester respectively, 7β-(D-α-tert.-butoxycarbonylamino-α-phenylacetylamino)-3-methoxy-3-cephem-4-carboxylic acid 4-nitrobenzyl ester and 7β-(D-α-tert.-butoxycarbonylamino-α-phenylacetylamino)-3-methoxy-3-cephem-4-carboxylic acid 2,2,2-trichloroethyl ester respectively.

EXAMPLE 28

A solution, cooled to −10° C., of 0.61 g of crude 7β-(D-α-tert.-butoxycarbonylamino-α-phenylacetylamino)-cepham-3-one-4ξ-carboxylic acid diphenylmethyl ester (which can be obtained, for example, according to the process of Example 4) in 30 ml of absolute methylene chloride is mixed with 0.12 ml of diisopropyl-ethyl-amine and 0.192 g of trimethyloxonium tetrafluoborate and the mixture is stirred for 30 minutes at −10° C., under a nitrogen atmosphere; in the course thereof, the oxonium salt gradually dissolves. The reaction mixture is poured out onto a mixture of ice and a saturated aqueous sodium chloride solution; the aqueous mixture is twice extracted with 100 ml of methylene chloride at a time and the organic phase is separated off, dried over sodium sulphate and evaporated under reduced pressure. The residue is purified by means of preparative thin layer chromatography (silica gel; system: diethyl ether). The zone visible under ultraviolet light (λ=254 mµ), which according to thin layer chromatography is a single substance, is isolated and stirred with 20 ml of diethyl ether; after stirring for 16 hours, 7β-(D-α-tert.-butoxycarbonylamino-α-phenylacetylamino)-3-methoxy-3-cephem-4-carboxylic acid diphenylmethyl ester is obtained in a finely crystalline form. Melting point 118°–120° C.

EXAMPLE 29

A solution of 0.100 g of crude 7β-(D-α-tert.-butoxycarbonylamino-α-phenylacetylamino)-cepham-3-one-4ξ-carboxylic acid diphenylmethyl ester (which can be obtained, for example, according to the process of Example 4) in 5 ml of nitromethane is mixed with 0.03 ml of diisopropyl-ethyl-amine and a solution of 0.036 g of trimethyloxonium tetrafluoborate in 0.5 ml of nitromethane and the mixture is stirred for 30 minutes under a nitrogen atmosphere at −10° C. The reaction mixture is worked up according to the process described in Example 28 and the crude product is purified by means of preparative layer chromatography. 7β-(D-α-tert.-Butoxycarbonylamino-α-phenylacetylamino)-3-methoxy-3-cephem-4-carboxylic acid diphenylmethyl ester, melting point 118°–120°, is thus obtained.

EXAMPLE 30

A solution of 0.1 g of crude 7β-(D-α-tert.-butoxycarbonylamino-α-phenylacetylamino)-cepham-3-one-4ξ-carboxylic acid diphenylmethyl ester (which can be obtained, for example, according to the process of Example 4) in 5 ml of methylene chloride is mixed with 0.045 ml of diisopropyl-ethyl-amine and 0.03 ml of trifluoromethanesulphonic acid methyl ester and the mixture is stirred for 30 minutes under a nitrogen atmosphere at room temperature. The reaction mixture is worked up according to the process described in Example 28 and is purified by means of preparative layer chromatography, whereby 7β-(D-α-tert.-butoxycarbonylamino-α-phenylacetylamino)-3-methoxy-3-cephem-4-carboxylic acid diphenylmethyl ester, melting point 118°–120° C., is obtained.

Instead of the trifluoromethanesulphonic acid methyl ester, it is possible to use the fluorosulphonic acid methyl ester as the methylating agent.

EXAMPLE 31

A solution of 0.100 g of 7β-(D-α-tert.-butoxycarbonylamino-α-phenylacetylamino)-3-methoxy-3-cephem-4-carboxylic acid diphenylmethyl ester in 0.5 ml of methylene chloride is mixed with 0.09 ml of anisole and 0.100 ml of trifluoroacetic acid and the mixture is stirred for 10 minutes at 0° C. and subsequently diluted with 20 ml of a 1:1 mixture of diethyl ether and pentane. The fine precipitate is filtered off, washed with a mixture of diethyl ether and pentane and dried under reduced pressure. 7β-(D-α-tert.-Butoxycarbonylamino-α-phenylacetylamino)-3-methoxy-3-cephem-4-carboxylic acid is thus obtained in the form of a colourless powder, thin layer chromatogram (silica gel; identification with iodine): Rf~0.64 (system: n-butanol/acetic acid/water, 67:10:23); ultraviolet absorption spectrum (in 95% strength aqueous ethanol): $\lambda_{max}=264$ mμ ($\epsilon=4,100$); infrared absorption spectrum (in methylene chloride): characteristic bands at 3.00μ, 5.64μ, 5.92μ, 6.25μ and 6.72μ.

If 7β-(D-α-tert.-butoxycarbonylamino-α-phenylacetylamino)-3-methoxy-3-cephem-4-carboxylic acid 4-nitrobenzyl ester is treated with hydrogen in the presence of a palladium-on-charcoal catalyst or 7β-(D-α-tert.-butoxycarbonylamino-α-phenylacetylamino)-3-methoxy-3-cephem-4-carboxylic acid 2,2,2-trichloroethyl ester is treated with zinc in the presence of 90% strength aqueous acetic acid, 7β-(D-α-tert.-butoxycarbonylamino-α-phenylacetylamino)-3-methoxy-3-cephem-4-carboxylic acid is obtained, which is identical with the above product.

EXAMPLE 32

A solution, cooled to 0° C., of 0.257 g of D-α-tert.-butoxycarbonylamino-α-(2-thienyl)-acetic acid in 25 ml of methylene chloride is mixed with 0.097 ml of N-methylmorpholine and 0.129 ml of chloroformic acid isobutyl ester and the mixture is stirred for 30 minutes under a nitrogen atmosphere, then cooled to −10° C. and treated successively with 0.300 g of 7β-amino-3-methoxy-3-cephem-4-carboxylic acid diphenylmethyl ester and 0.085 ml of N-methyl-morpholine. The reaction mixture is stirred for 30 minutes at −10° C. and for 30 minutes at 0° C. and is then treated with 20 ml of water, and the pH value is adjusted to 7.9 by adding a 40% strength aqueous dipotassium hydrogen phosphate solution. The phases are separated, the aqueous solution is extracted with methylene chloride and the combined organic solutions are washed with a saturated aqueous sodium chloride solution, dried over sodium sulphate and evaporated under reduced pressure. The oily residue is purified by means of preparative layer chromatography (silica gel; system: diethyl ether; identification with ultraviolet light, $\lambda=254$ mμ). Amorphous 7β-[D-α-tert.-butoxycarbonylamino-α-(2-thienyl)-acetylamino]-3-methoxy-3-cephem-4-carboxylic acid diphenylmethyl ester is thus obtained as a single product according to thin layer chromatography, thin layer chromatogram (silica gel; identification with ultraviolet light, $\lambda=254$ mμ): Rf~0.34 (system: diethyl ether); $[\alpha]_D^{20}=+26°\pm1°$ (c=0.86 in chloroform); ultraviolet absorption spectrum (in 95% strength aqueous ethanol): $\lambda_{max}=240$ mμ ($\epsilon=12,500$) and 280 mμ ($\epsilon=6,000$); infrared absorption spectrum (in methylene chloride): characteristic bands at 2.94μ, 5.62μ, 5.85μ, 6.26μ and 6.72μ.

EXAMPLE 33

A mixture of 0.200 g of 7β-[D-α-tert.-butoxycarbonylamino-α-(2-thienyl)-acetylamino]-3-methoxy-3-cephem-4-carboxylic acid diphenylmethyl ester, 0.5 ml of anisole and 10 ml of pre-cooled trifluoroacetic acid is stirred for 15 minutes at 0° C. and is subsequently mixed with 50 ml of cold toluene and evaporated under reduced pressure. The residue is stirred with diethyl ether and the pulverulent precipitate is filtered off and dried.

The salt, thus obtained, of 7β-[D-α-amino-α-(2-thienyl)-acetylamino]-3-methoxy-3-cephem-4-carboxylic acid with trifluoroacetic acid is dissolved in about 6 ml of water, the pH value of the solution is adjusted to 1.5 by adding 2 N hydrochloric acid and the aqueous solution is washed with 20 ml of ethyl acetate and its pH value is adjusted to 5.0 by dropwise addition of a 20% strength solution of triethylamine in methanol. The mixture is diluted with 20 ml of acetone and left to stand for 16 hours at 0° C. The fine, colourless and microcrystalline powder is filtered off, washed with acetone and dried and yields 7β-[D-α-amino-α-(2-thienyl)-acetylamino]-3-methoxy-3-cephem-4-carboxylic acid in the form of the internal salt, melting point 140° C. (with decomposition); thin layer chromatogram (silica gel; identification with iodine): Rf~0.22 (system: n-butanol-/acetic acid/water, 67:10:23) and Rf~0.53 (system: isopropanol/formic acid/water, 77:4:19); ultraviolet absorption spectrum: $\lambda_{max}=235$ mμ ($\epsilon=11,400$) and $\lambda_{shoulder}=272$ mμ ($\epsilon=6,100$) in 0.1 N hydrochloric acid, and $\lambda_{max}=238$ mμ ($\epsilon=11,800$) and $\lambda_{shoulder}=267$ mμ ($\epsilon=6,500$) in 0.1 N aqueous sodium bicarbonate solution.

EXAMPLE 34

A solution, cooled to 0° C., of 0.353 g of D-α-tert.-butoxycarbonylamino-α-(4-hydroxy-phenyl)-acetic acid in 100 ml of methylene chloride is stirred for 30 minutes with 0.132 ml of N-methyl-morpholine and 0.180 ml of chloroformic acid isobutyl ester under a nitrogen atmosphere and the mixture is then cooled to −10° C. and 0.400 g of 7β-amino-3-methoxy-3-cephem-4-carboxylic acid diphenylmethyl ester and 0.110 ml of N-methyl-morpholine are added successively. The reaction mixture is stirred for 30 minutes at −10° C. and for 30 minutes at 0° C., 30 ml of water are added and the pH value is adjusted to 7.9 by adding 40% strength aqueous dipotassium hydrogen phosphate solution. The phases are separated, the aqueous solution is extracted with methylene chloride and the combined organic solutions are washed with a saturated aqueous sodium chloride solution, dried over sodium sulphate and evaporated under reduced pressure. The residue is purified by means of preparative layer chromatography (silica gel; system: toluene/ethyl acetate, 1:1; identification with ultraviolet light, $\lambda=254$ mμ; Rf~0.32). 7β-[D-α-tert.-Butoxycarbonyl-amino-α-(4-hydroxy-phenyl)-acetylamino]-3-methoxy-3-cephem-4-carboxylic acid diphenylmethyl ester, which according to thin layer chromatography is a single substance is obtained; thin layer chromatogram (silica gel; identification with iodine): Rf~0.35 (system: toluene/ethyl acetate, 1:1); $[\alpha]_D^{20}\sim-1°\pm1°$ (c=0.566 in chloroform); ultraviolet absorption spectrum (in 95% strength aqueous ethanol): $\lambda_{max}=276$ mμ ($\epsilon=7,400$); infrared absorption spectrum (in methylene chloride): characteristic bands at 2.83μ, 2.96μ, 5.64μ, 5.86μ, 5.91μ (shoulder), 6.23μ, 6.28μ, 6.65μ and 6.72μ.

EXAMPLE 35

A mixture of 0.095 g of 7β-[D-α-tert.-butoxycarbonylamino-α-(4-hydroxy-phenyl)-acetylamino]-3-methoxy-3-cephem-4-carboxylic acid diphenylmethyl ester, 0.25 ml of anisole and 5 ml of pre-cooled trifluoroacetic acid is stirred for 15 minutes at 0° C., 50 ml of cold toluene are then added and the mixture is evaporated under reduced pressure. The residue is stirred with diethyl ether and the pulverulent precipitate is filtered off and dried. The salt, thus obtained, of 7β-[D-α-amino-α-(4-hydroxy-phenyl)-acetylamino]-3-methoxy-3-cephem-4-carboxylic acid with trifluoroacetic acid is dissolved in about 5 ml of water, the pH value of the solution is adjusted to 1.5 by adding 2 N hydrochloric acid, the aqueous solution is washed with 20 ml of ethyl acetate and its pH value is adjusted to 5.0 by dropwise addition of a 20% strength solution of triethylamine in methanol, whereupon a colourless precipitate forms. The mixture is diluted with 8 ml of acetone and left to stand for 16 hours at 0° C. The precipitate is filtered off, washed with acetone and diethyl ether and dried under reduced pressure. 7β-[D-α-Amino-α-(4-hydroxy-phenyl)-acetylamino]-3-methoxy-3-cephem-4-carboxylic acid is thus obtained in the form of the internal salt, melting point = 180° C. (with decomposition); thin layer chromatogram (silica gel; identification with iodine): Rf∼0.24 (system: n-butanol/acetic acid/water, 67:10:23) and Rf∼0.57 (system: isopropanol/formic acid/water, 77:4:19); ultraviolet absorption spectrum: $\lambda_{max}$=228 mμ ($\epsilon$=12,000) and 271 mμ ($\epsilon$=6,800) in 0.1 N hydrochloric acid, and $\lambda_{max}$=227 mμ ($\epsilon$=10,500) and $\lambda_{shoulder}$=262 mμ ($\epsilon$=8,000) in 0.1 N aqueous sodium bicarbonate solution.

EXAMPLE 36

A solution, cooled to 0° C., of 0.336 g of D-α-tert.-butoxycarbonylamino-α-(4-isothiazolyl)-acetic acid in 100 ml of methylene chloride is stirred for 30 minutes with 0.132 g of N-methyl-morpholine and 0.180 ml of chloroformic acid isobutyl ester under a nitrogen atmosphere, the mixture is then cooled to −10° C. and 0.400 g of 7β-amino-3-methoxy-3-cephem-4-carboxylic acid diphenylmethyl ester and 0.110 ml of N-methyl-morpholine are added successively. The reaction mixture is stirred for 30 minutes at −10° C. and for 60 minutes at 0° C. and is diluted with 30 ml of water, and the pH value is adjusted to 7.9 by addition of 40% strength aqueous dipotassium hydrogen phosphate solution. The phases are separated, the aqueous solution is extracted with methylene chloride and the combined organic solutions are washed with a saturated aqueous sodium chloride solution, dried over sodium sulphate and evaporated under reduced pressure. The residue is purified by means of preparative layer chromatography (silica gel; system: toluene/ethylacetate, 1:1; identification by ultraviolet light, λ=254 mμ). At Rf∼0.68, 7β-[D-α-tert.-butoxycarbonylamino-α-(4-isothiazolyl)-acetylamino]-3-methoxy-2-cephem-4α-carboxylic acid diphenylmethyl ester is thus obtained, melting point = 170° C. after crystallisation from a mixture of methylene chloride and pentane; $[\alpha]_D^{20}$= +147±1° (c=0.79 in chloroform); thin layer chromatogram (silica gel; identification with iodine): Rf∼0.68 (system: toluene/ethyl acetate, 1:1); ultraviolet absorption spectrum (in 95% strength aqueous ethanol): $\lambda_{max}$=248 mμ ($\epsilon$=10,700); infrared absorption spectrum (in methylene chloride): characteristic bands at 2.96μ, 5.63μ, 5.75μ, 5.87μ, 6.18μ and 6.72μ; whilst at Rf∼0.43, amorphous 7β-[D-α-tert.-butoxycarbonylamino-α-(4-isothiazolyl)-acetylamino]-3-methoxy-3-cephem-4-carboxylic acid diphenylmethyl ester is obtained, $[\alpha]_D^{20}$= +26°±1° (c=0.65 in chloroform); thin layer chromatogram (silica gel; identification with iodine): Rf∼0.43 (system: toluene/ethyl acetate, 1:1); ultraviolet absorption spectrum (in 95% strength aqueous ethanol): $\lambda_{max}$=250 mμ ($\epsilon$=12,200) and 280 mμ ($\epsilon$=5,900); infrared absorption spectrum (in methylene chloride): characteristic bands at 2.94μ, 5.65μ, 5.71μ (shoulder), 5.88μ, 6.28μ and 6.73μ.

EXAMPLE 37

A suspension of 1.65 g of 7β-amino-3-methoxy-3-cephem-4-carboxylic acid diphenylmethyl ester and 2 ml of anisole is mixed with 20 ml of pre-cooled trifluoroacetic acid and stirred for 15 minutes in an ice bath. It is diluted with 100 ml of cold toluene and the reaction mixture is evaporated under reduced pressure. The dark brown residue is dried under a high vacuum and stirred with diethyl ether; the precipitate is filtered off, washed with acetone and diethyl ether and dried. The salt, thus obtainable, of 7β-amino-3-methoxy-3-cephem-4-carboxylic acid and of trifluoroacetic acid is dissolved in 10 ml of water; the aqueous solution is twice washed with 10 ml of ethyl acetate at a time and brought to a pH of 4.5 by adding a 10% strength solution of triethylamine in methanol. The mixture is diluted with 10 ml of acetone and stirred for one hour at 0° C. The precipitate is filtered off, washed with a 1:2 mixture of acetone and diethyl ether and dried in a high vacuum and yields 7β-amino-3-methoxy-3-cephem-4-carboxylic acid in the form of the internal salt, thin layer chromatogram (silica gel): Rf∼0.16 (system: n-butanol/acetic acid/water, 67:10:23); ultraviolet absorption spectrum (in 0.1 N hydrochloric acid): $\lambda_{max}$=261 mμ ($\epsilon$=5,400).

In the 7β-amino-3-methoxy-3-cephem-4-carboxylic acid which can be prepared according to the above process, it is possible, by treatment with trimethylchlorosilane, to convert the carboxyl group, and, if using an excess of the silylating agent, also the amino group, into the carboxyl group protected by a trimethylsilyl group and, where applicable, into the amino group protected in the same way, and in the trimethylsilylated 7β-amino-3-methoxy-3-cephem-4-carboxylic acid the amino group can be acylated by treatment with phenylacetyl chloride; after the customary working up in the presence of water, 3-methoxy-7β-phenylacetylamino-3-cephem-4-carboxylic acid is obtained.

EXAMPLE 38

A mixture of 0.251 g of crude 7β-(D-α-tert.-butoxycarbonylamino-α-phenylacetylamino)-cepham-3-one-4ξ-carboxylic acid diphenylmethyl ester and 12.5 ml of methylene chloride is mixed, at 0° C., with 0.044 ml of diisopropyl-ethyl-amine and 0.038 ml of chloroformic acid methyl ester and the mixture is stirred under a nitrogen atmosphere for 30 minutes at 0° C. and for 1½ hours at room temperature. The organic layer is separated off, washed with a saturated aqueous sodium chloride solution, dried over sodium sulphate and evaporated under reduced pressure. The residue is chromatographed on 20 g of silica gel, and 7β-(D-α-tert.-butoxycarbonylamino-α-phenylacetylamino)-3-methoxy-carbonyloxy-3-cephem-4-carboxylic acid diphenylmethyl ester is eluted with toluene containing 20% of ethyl acetate. The compound, which is a single substance according to thin layer chromatography, is lyophilised from benzene, thin layer chromatogram (silica gel; identification: iodine): Rf∼0.31 (system: toluene/ethyl acetate, 3:1); ultraviolet absorption spectrum (in 95% strength aqueous ethanol): $\lambda_{max}$=252 mμ ($\epsilon$=5,100) and 257 mμ ($\epsilon$=5,100); infrared absorption spectrum (in methylene chloride): characteristic bands at 2.94μ, 5.58μ, 5.64μ (shoulder), 5.81μ (shoulder), 5.88μ and 6.68μ.

EXAMPLE 39

The 7β-amino-3-methoxy-3-cephem-4-carboxylic acid described in Example 37 can be N-acylated in accordance with the following general processes and be converted into corresponding 7β-Ac-amino-3-methoxy-3-cephem-4-carboxylic acids, wherein Ac represents an acyl radical:

Variant A: 0.5 mmol of an acid (AcOH) is dissolved in 10 ml of absolute methylene chloride, with the addition of 0.070 ml (0.5 mmol) of triethylamine [stock solution: 28.0 ml (200 mmols) of triethylamine, diluted to 100 ml with methylene chloride]. 0.0565 ml (0.5 mmol) of trichloroacetic acid chloride in 0.2 ml of methylene chloride [stock solution 22.6 ml (200 mmols) of trichloroacetic acid chloride diluted to 100 ml with methylene chloride] is added to the solution cooled to $-15°$ C. and the mixture is stirred for 30 minutes at $-15°$ C. The solution containing the mixed anhydride [Ac—O—C(=O)—CCl$_3$] is mixed with a finely dispersed suspension, cooled to $-15°$ C., of 0.057 g (0.25 mmol) of 7β-amino-3-methoxy-3-cephem-4-carboxylic acid and 0.070 ml (0.5 mmol) of triethylamine in 5 ml of methylene chloride and the mixture is vibrated for 30 minutes at $-15°$ C. and then for 30 minutes at 20° C. in an ultrasonic bath. The reaction solution, which is usually brown, is evaporated to dryness under reduced pressure and the resulting residue is partitioned between 10 ml of a 10% strength aqueous dipotassium hydrogen phosphate solution (pH 8.9) and 5 ml of ethyl acetate. The aqueous phase is adjusted to pH 2.6 with 20% strength aqueous phosphoric acid and is thereafter exhaustively extracted with ethyl acetate. The ethyl acetate extract (30–50 ml) is washed with water, dried over sodium sulphate and evaporated under reduced pressure. The residue is preparatively chromatographed for 2–5 hours on a silica gel layer plate, in a suitable solvent system. After drying the plate at room temperature in a nitrogen atmosphere, the silica gel zone which absorbs under ultraviolet light ($\lambda=254$ mμ) is mechanically detached from the plate and extracted three times with 10 to 20 ml of ethanol or methanol. After evaporating the extract under reduced pressure, 7βacyl-amino-3-methoxy-3-cephem-4-carboxylic acid is obtained as a beige or almost colourless residue.

If the layer plate possesses more than one zone which absorbs in ultraviolet light, the individual zones are worked up separately as described above. A sample of the material resulting from the various zones is tested in the plate diffusion test against *Staphylococcus aureus*. The material from the microbiologically most active zone is subjected to a renewed preparative layer separation, from which the product which is chromatographically a single substance can be isolated.

Variant B: 0.2 mmol of the sodium salt of an acid [AcONa] in 5 ml of absolute dimethylformamide is treated with 0.2 mmol of trichloroacetyl chloride as in Variant A and reacted with a solution of 0.2 mmol of 7β-amino-3-methoxy-3-cephem-4-carboxylic acid and 0.2 mmol of triethylamine in 2 ml of dimethylformamide, and worked up, as in Variant A.

Variant C: A mixture of 0.25 mmol of an acid chloride [AcCl] in 4 ml of methylene chloride is added to a solution, cooled to $-15°$ C., of 0.058 g (0.25 mmol) of 7β-amino-3-methoxy-3-cephem-4-carboxylic acid and 0.070 ml (0.5 mmol) of triethylamine in 5 ml of methylene chloride, and reacted, and worked up, as in Variant A.

In the above process variants A, B and C, trimethylchlorosilane in the presence of pyridine can be used instead of triethylamine.

EXAMPLE 40

If in the process of Example 39, Variant B, the sodium salt of the methyl half-ester of malonic acid is used as the acylating starting material, 3-methoxy-7β-methoxycarbonylacetyl-amino-3-cephem-4-carboxylic acid is obtained, which shows an Rf value of 0.5–0.6 in a thin layer chromatogram (silica gel; system: ethyl acetate/acetic acid, 9:1); ultraviolet absorption spectrum (in methanol): $\lambda_{max}$ at 265 mμ; infrared absorption spectrum (in mineral oil): characteristic band at 5.66μ.

EXAMPLE 41

If in the process of Example 39, Variant C, bromoacetic acid chloride is used as the acylating starting material, 7β-bromoacetyl-amino-3-methoxy-3-cephem-4-carboxylic acid is obtained, which in a thin layer chromatogram (silica gel; system: n-butanol/acetic acid/water, 75:7.5:21) shows an Rf value of 0.25–0.35; ultraviolet absorption spectrum (in 95% strength aqueous ethanol): $\lambda_{max}$ at 264 mμ.

EXAMPLE 42

If in Example 39, Variant C, phenoxyacetyl chloride is used as the acylating starting material, 3-methoxy-7β-phenoxyacetyl-amino-3-cephem-4-carboxylic acid is obtained, which shows an Rf value of 0.3–0.4 in a thin layer chromatogram (silica gel; system: n-butanol/acetic acid/water, 75:7.5:21); ultraviolet absorption spectrum (in 95% strength aqueous ethanol): $\lambda_{max}=266$ mμ; infrared absorption spectrum (in mineral oil): characteristic band at 5.66μ.

EXAMPLE 43

If in Example 39, Variant C, 2-thienylacetyl chloride is used as the acylating starting material, 3-methoxy-7β-(2-thienyl)-acetylamino-3-cephem-4-carboxylic acid is obtained, which in a thin layer chromatogram (silica gel; system: n-butanol/pyridine/acetic acid/water, 38:24:8:30) shows an Rf value of 0.5–0.6; ultraviolet absorption spectrum (in 95% strength aqueous ethanol): $\lambda_{max}$ at 235 and 264 mμ.

EXAMPLE 44

If in the process of Example 39, Variant A, α-phenylmalonic acid is used as the acylating starting material, 7β-(α-carboxy-α-phenylacetylamino)-3-methoxy-3-cephem-4-carboxylic acid is obtained, which in a thin layer chromatogram (silica gel; system: n-butanol/pyridine/acetic acid/water, 40:24:6:30) shows two zones: the more rapidly migrating zone, with Rf=0.4–0.5, contains 7β-phenylacetylamino-3-methoxy-3-cephem-4-carboxylic acid and the more slowly migrating zone, with Rf=0.2–0.3, contains the desired 7β-(α-carboxy-α-phenylacetylamino)-3-methoxy-3-cephem-4-carboxylic acid.

EXAMPLE 45

A 10% strength suspension of 0.046 g of 7β-amino-3-methoxy-3-cephem-4-carboxylic acid and 0.020 g (0.2 mmol) of triethylamine in methylene chloride is mixed with a 10% strength solution of 0.0218 g (0.26 mmol) of diketene in methylene chloride and the mixture is vibrated in an ultrasonic bath for one hour at 22° C.; after about 30 minutes, a clear solution is obtained. The reaction mixture is worked up according to the process of Example 39, Variant A, and 7β-acetoacetylamino-3-methoxy-3-cephem-4-carboxylic acid is thus obtained, which in a thin layer chromatogram (silica gel; system: n-butanol/acetic acid/water, 75:5:21) shows an Rf value of 0.3–0.4; ultraviolet absorption spectrum (in 95% strength aqueous ethanol): $\lambda_{max}$ at 238 mμ and 265 mμ.

EXAMPLE 46

If in the process of Example 39, Variant A, cyanoacetic acid is used as the acylating starting material, 7β-cyanoacetylamino-3-methoxy-3-cephem-4-carboxylic acid is obtained, which in a thin layer chromatogram (silica gel; system: n-butanol/pyridine/acetic acid/water, 38:24:8:30) shows an Rf value of 0.35–0.45; ultraviolet absorption spectrum (in 95% strength aqueous ethanol): $\lambda_{max}$ at 264 mμ; infrared absorption spectrum (in mineral oil): characteristic bands at 4.32μ and 5.65μ.

EXAMPLE 47

If in Example 41, Variant C, α-cyano-propionic acid chloride is used as the acylating starting material, 7β-(α-cyanopropionylamino)-3-methoxy-3-cephem-4-carboxylic acid is obtained, which in a thin layer chromatogram (silica gel; system: n-butanol/pyridine/acetic acid/water, 38:24:8:30) shows an Rf value of 0.4–0.5; ultraviolet absorption spectrum (in 95% strength aqueous ethanol): $\lambda_{max}$ at 265 mμ; infrared absorption spectrum (in mineral oil): characteristic bands at 4.44μ and 5.66μ.

EXAMPLE 48

If in the process of Example 39, Variant A, α-cyanophenylacetic acid is used as the acylating starting material, 7β-(α-cyano-α-phenylacetylamino)-3-methoxy-3-cephem-4-carboxylic acid is obtained, which in a thin layer chromatogram (silica gel; system: n-butanol/acetic acid/water, 75:7.5:21) shows an Rf value of 0.3–0.4; ultraviolet absorption spectrum (in 95% strength aqueous ethanol): $\lambda_{max}$ at 267 mμ; infrared absorption spectrum (in mineral oil): characteristic bands at 4.42μ and 5.65μ.

EXAMPLE 49

A 10% strength suspension of 0.046 g of 7β-amino-3-methoxy-3-cephem-4-carboxylic acid and 0.0429 g (0.3 mmol) of tri-n-butylamine in dimethylformamide is mixed with a 10% strength solution of 0.0422 g (0.4 mmol) of 2-chloroethylisocyanate in dimethylformamide and the mixture is vibrated in an ultrasonic bath for one hour at 22° C. It is then worked up according to the process described in Example 41, Variant A, and 7β-(2-chloroethylamino-carbonylamino)-3-methoxy-3-cephem-4-carboxylic acid is thus obtained, which in a thin layer chromatogram (silica gel) shows Rf values of 0.3–0.4 (system: n-butanol/acetic acid/water, 75:7.5:21); ultraviolet absorption spectrum (in 0.1 molar hydrochloric acid): $\lambda_{max}$ at 266 mμ.

EXAMPLE 50

If in the process of Example 39, Variant A, dichloroacetic acid is used as the acylating starting material, 7β-dichloroacetylamino-3-methoxy-3-cephem-4-carboxylic acid is obtained, which in a thin layer chromatogram (silica gel; system: n-butanol/acetic acid/water, 75:7.5:21) shows an Rf value of 0.40; ultraviolet absorption spectrum (in 95% strength aqueous ethanol): $\lambda_{max}$ at 264 mμ; infrared absorption spectrum (in mineral oil): characteristic band at 5.67μ.

EXAMPLE 51

A suspension of 0.110 g of 7β-amino-3-methoxy-3-cephem-4-carboxylic acid in 2 ml of water is dissolved by addition of 0.0635 g of sodium bicarbonate and 0.142 g of α-sulpho-α-phenylacetyl chloride in 5 ml of diethyl ether is added dropwise at 0° C. The mixture is stirred for 1 hour at 0°–5° C. and is subsequently treated with 1.5 mmols of sodium α-ethyl-hexanoate and the product which has separated out is filtered off. After washing with methylene chloride and diethyl ether, the pulverulent precipitate, consisting of the disodium salt of 3-methoxy-7β-(α-sulpho-α-phenylacetylamino)-3-cephem-4-carboxylic acid, is dried under a high vacuum; thin layer chromatogram (silica gel): Rf~0.10–0.20 (system: n-butanol/acetic acid/water, 67:10:23).

EXAMPLE 52

If in the process of Example 39, Variant A, malonic acid N-phenyl-half-amide is used as the acylating starting material, 3-methoxy-7β-(α-phenylaminocarbonylacetylamino)-3-methoxy-3-cephem-4-carboxylic acid is obtained, which in a thin layer chromatogram (silica gel; system: n-butanol/acetic acid/water, 67:10:23) shows an Rf value of 0.30; ultraviolet absorption spectrum (in ethanol): $\lambda_{max}$ at 241 mμ and 266 mμ; infrared absorption spectrum (in mineral oil): characteristic band at 5.65μ.

EXAMPLE 53

If in Example 39, Variant C, methoxyacetic acid chloride is used as the acylating starting material, 3-methoxy-7β-methoxyacetylamino-3-cephem-4-carboxylic acid is obtained, which in a thin layer chromatogram (silica gel; system: ethyl acetate/pyridine/acetic acid/water, 60:20:6:11) shows an Rf value of 0.30; ultraviolet absorption spectrum (in mineral oil): characteristic band at 5.64μ.

EXAMPLE 54

If in Example 39, Variant C, 4-methylphenyl-thioacetic acid chloride is used as the acylating starting material, 3-methoxy-7β-(α-4-methylphenylthioacetylamino)-3-cephem-4-carboxylic acid is obtained, which in a thin layer chromatogram (silica gel; system: n-butanol/acetic acid/water, 67:10:23) shows an Rf value of 0.45; ultraviolet absorption spectrum (in ethanol): $\lambda_{max}$ at 264 mμ; infrared absorption spectrum (in mineral oil): characteristic band at 5.63μ.

EXAMPLE 55

If in the process of Example 39, Variant A, benzoylacetic acid is used as the acylating starting material, 7β-benzoylacetylamino-3-methoxy-3-cephem-4-carboxylic acid is obtained, which in a thin layer chromatogram (silica gel; system: n-butanol/pyridine/acetic acid/water, 38:24:8:30) shows an Rf value of 0.40; ultraviolet absorption spectrum (in 95% strength aqueous ethanol): $\lambda_{max}$=267 mμ; infrared absorption spectrum (in mineral oil): characteristic band at 5.66μ.

EXAMPLE 56

If in Example 39, Variant C, 3-chloropropionic acid chloride is used as the acylating starting material, 7β-(3-chloropropionylamino)-3-methoxy-3-cephem-4-carboxylic acid is obtained, which in a thin layer chromatogram (silica gel; system: n-butanol/acetic acid/water, 75:7.5:21) shows an Rf value of 0.30; ultraviolet absorption spectrum (in 95% strength aqueous ethanol): $\lambda_{max}$ at 265 m$\mu$; infrared absorption spectrum (in mineral oil): characteristic band at 5.65$\mu$.

EXAMPLE 57

If in Example 39, Variant C, chloroacetic acid chloride is used as the acylating starting material, 7$\beta$-chloroacetylamino-3-methoxy-3-cephem-4-carboxylic acid is obtained, which is a thin layer chromatogram (silica gel; system: n-butanol/pyridine/acetic acid/water, 38:24:8:30) shows an Rf value of 0.50; ultraviolet absorption spectrum (in 95% strength aqueous ethanol): $\lambda_{max}$ at 266 m$\mu$; infrared absorption spectrum (in mineral oil): characteristic band at 5.65$\mu$.

EXAMPLE 58

If in Example 39, Variant C, 2-propenecarboxylic acid chloride is used as the acylating starting material, 7$\beta$-(3-butenoyl-amino)-3-methoxy-3-cephem-4-carboxylic acid is obtained, which in a thin layer chromatogram (silica gel; system: n-butanol/pyridine/acetic acid/water, 38:24:8:30) shows an Rf value of 0.65.

EXAMPLE 59

If in the process of Example 39, Variant A, methylthioacetic acid is used as the acylating starting material, 3-methoxy-7$\beta$-($\alpha$-methylthio-acetylamino)-3-cephem-3-cephem-4-carboxylic acid is obtained, which in a thin layer chromatogram (silica gel; system: n-butanol/pyridine/acetic acid/water, 38:24:8:30) shows an Rf value of 0.60; ultraviolet absorption spectrum (in 95% strength aqueous ethanol): $\lambda_{max}$ at 266 m$\mu$; infrared absorption spectrum (in mineral oil): characteristic band at 5.7$\mu$.

EXAMPLE 60

If in Example 39, Variant C, bis-methoxycarbonylacetic acid chloride is used as the acylating starting material, 7$\beta$-(bis-methoxycarbonyl-acetylamino)-3-methoxy-3-cephem-4-carboxylic acid is obtained, which in a thin layer chromatogram (silica gel; system: n-butanol/pyridine/acetic acid/water, 38:24:8:30) shows an Rf value of 0.45; ultraviolet absorption spectrum (in 0.1 molar aqueous sodium bicarbonate solution): $\lambda_{max}$ at 268 m$\mu$; infrared absorption spectrum (in mineral oil): characteristic band at 5.64$\mu$.

The bis-methoxycarbonyl-acetic acid chloride used as the acylating agent is prepared by reaction of the sodium salt of malonic acid dimethyl ester in tetrahydrofurane with phosgene at $-10°$ C.

EXAMPLE 61

If in Example 39, Variant C, dibromoacetic acid chloride is used as the acylating starting material, 7$\beta$-dibromoacetylamino-3-methoxy-3-cephem-4-carboxylic acid is obtained, which in a thin layer chromatogram (silica gel; system: n-butanol/acetic acid/water, 75:7.5:21) shows an Rf value of 0.3 to 0.4; ultraviolet absorption spectrum (in 0.1 molar aqueous sodium bicarbonate solution): $\lambda_{max}$ at 264 m$\mu$; infrared absorption spectrum (in mineral oil): characteristic band at 5.63$\mu$.

EXAMPLE 62

If in the process of Example 39, Variant C, pivalic acid chloride is used as the acylating agent, 3-methoxy-7$\beta$-pivalylamino-3-cephem-4-carboxylic acid is obtained, thin layer chromatogram (silica gel): Rf~0.5–0.6 (system: n-butanol/pyridine/acetic acid/water, 38:24:8:30); ultraviolet absorption spectrum (in 95% strength aqueous ethanol): $\lambda_{max}$~265 m$\mu$; infrared absorption spectrum (in mineral oil): characteristic band at 5.66$\mu$.

EXAMPLE 63

If in the process of Example 39, Variant C, $\alpha$-azido-$\alpha$-phenylacetic acid chloride is used as the acylating agent, 7$\beta$-($\alpha$-azido-$\alpha$-phenylacetylamino)-3-methoxy-3-cephem-4-carboxylic acid is obtained, thin layer chromatogram (silica gel): Rf~0.4–0.5 (system: n-butanol/pyridine/acetic acid/water, 38:24:8:30); ultraviolet absorption spectrum (in 95% strength aqueous ethanol): $\lambda_{max}$~267 m$\mu$; infrared absorption spectrum (in mineral oil): characteristic bands at 4.66$\mu$ and 5.65$\mu$.

EXAMPLE 64

If in the process of Example 39, Variant C, $\alpha$-O,O-dimethylphosphono-$\alpha$-phenylacetic acid chloride is used as the acylating agent, 7$\beta$-$\alpha$-O,O-dimethyl-phosphono-$\alpha$-phenylacetylamino)-3-methoxy-3-cephem-4-carboxylic acid is obtained, thin layer chromatogram (silica gel): Rf~0,4 (system: n-butanol/acetic acid/water, 67:10:23); ultraviolet absorption spectrum (in 95% strength ethanol): $\lambda_{max}$~266 m$\mu$; infrared absorption spectrum (in mineral oil): characteristic band at 5.66$\mu$.

EXAMPLE 65

If in the process of Example 39, Variant C, 5-methyl-3-phenyl-3-isoxazolecarboxylic acid chloride is used as the acylating agent, 3-methoxy-7$\beta$-(5-methyl-3-phenyl-4-isoxazolylcarbonylamino)-3-cephem-4-carboxylic acid is obtained, thin layer chromatogram (silica gel): Rf~0.3–0.4 (system: n-butanol/acetic acid/water, 67:10:23); infrared absorption spectrum (in mineral oil): characteristic band at 5.65$\mu$.

EXAMPLE 66

If in the process of Example 39, Variant C, 4-aminomethyl-phenylacetic acid chloride hydrochloride is used as the acylating agent, evaporation of the reaction mixture, stirring the residue with a 1:1 mixture of acetone and diethyl ether, filtration and thorough rinsing yields amorphous 7$\beta$-(4-aminomethyl-phenylacetylamino)-3-methoxy-3-cephem-4-carboxylic acid, thin layer chromatogram (silica gel): Rf~0.25–0.3 (system: n-butanol/acetic acid/water, 67:10:23); ultraviolet absorption spectrum (in 0.1 N hydrochloric acid): $\lambda_{max}$~265 m$\mu$; infrared absorption spectrum (in mineral oil); characteristic band at 5.68$\mu$.

EXAMPLE 67

If in the process of Example 39, Variant C, 2,6-dimethoxy-benzoic acid chloride is used as the acylating agent, 7$\beta$-(2,6-dimethoxy-benzoylamino)-3-methoxy-3-cephem-4-carboxylic acid is obtained, thin layer chromatogram (silica gel): Rf 0.50 (system: n-butanol/pyridine/acetic acid/water, 40:24:6:30); ultraviolet absorption spectrum (in 95% strength aqueous ethanol): $\lambda_{max}$=265 m$\mu$; infrared absorption spectrum (in mineral oil): characteristic band at 5.64$\mu$.

EXAMPLE 68

If in the process of Example 39, Variant A, D-$\alpha$-tert.-butoxycarbonylamino-$\alpha$-(3-thienyl)-acetic acid is used as the acylating agent, 7$\beta$-[D-$\alpha$-tert.-butoxycarbonylamino-α-(3-thienyl)-acetylamino]-3-methoxy-3-cephem-4-carboxylic acid diphenylmethyl ester is obtained; thin layer chromatogram (silica gel): Rf~0.3–0.4 (system: diethyl ether); ultraviolet absorption spectrum (in 95% strength aqueous ethanol): $\lambda_{max}$=238 mμ and 276 mμ. This is converted, by treatment with trifluoroacetic acid and anisole, followed by adjusting the pH value of an aqueous solution of the trifluoroacetic acid addition salt of 7β-[D-α-amino-α-(3-thienyl)-acetylamino]-3-methoxy-3-cephem-4-carboxylic acid, thus obtainable, to about 5, into the free 7β-[D-α-amino-α-(3-thienyl)-acetylamino]-3-methoxy-3-cephem-4-carboxylic acid, thin layer chromatogram (silica gel): Rf~0.2–0.3 (system: n-butanol/acetic acid/water, 67:10:23); ultraviolet absorption spectrum (in 0.1 N hydrochloric acid): $\lambda_{max}$=235 mμ and 270 mμ.

EXAMPLE 69

If in the process of Example 39, Variant A, D-α-tert.-butoxycarbonylamino-α-(2-furyl)-acetic acid is used as the acylating agent, 7β-[D-α-tert.-butoxycarbonylamino-α-(2-furyl)-acetylamino]-3-methoxy-3-cephem-4-carboxylic acid diphenylmethyl ester is obtained; thin layer chromatogram (silica gel): Rf~0.35 (system: diethyl ether); ultraviolet absorption spectrum (in 95% strength aqueous ethanol): $\lambda_{max}$~265 mμ. This is converted, by treatment with trifluoroacetic acid and anisole, followed by adjusting the pH value of an aqueous solution of the trifluoroacetic acid addition salt of 7β-[D-α-amino-α-(2-furyl)-acetylamino]-3-methoxy-3-cephem-4-carboxylic acid, thus obtainable, to about 5, into free 7β-[D-α-amino-α-(2-furyl)-acetylamino]-3-methoxy-3-cephem-4-carboxylic acid, thin layer chromatogram (silica gel): Rf~0.25 (system: n-butanol/acetic acid/water, 67:10:23); ultraviolet absorption spectrum (in 0.1 N hydrochloric acid): $\lambda_{max}$~265 mμ.

EXAMPLE 70

The pH value of a solution of 0.092 g of 7β-amino-3-methoxy-3-cephem-4-carboxylic acid in 2 ml of acetone, 0.8 ml of water and 1.2 ml of an 0.5 molar aqueous dipotassium hydrogen phosphate solution is adjusted to 7.5 by further addition of dipotassium hydrogen phosphate, the mixture is cooled to 0° C. and 0.142 g of the internal anhydride of O-carboxyl-D-mandelic acid is added whilst checking the pH value. After allowing the mixture to react for 30 minutes at 0° C., the acetone is removed under reduced pressure and the aqueous solution is covered with ethyl acetate and acidified with 5 molar aqueous phosphoric acid to a pH value of about 2.5. The aqueous phase is separated off and extracted with ethyl acetate. The combined organic solutions are twice washed with a saturated aqueous sodium chloride solution, dried over sodium sulphate and evaporated under reduced pressure. The residue is chromatographed on 5 g of silica gel; the excess mandelic acid is eluted with methylene chloride, containing 10–15% of methyl acetate, and 7β-(D-α-hydroxy-α-phenylacetylamino)-3-methoxy-3-cephem-4-carboxylic acid is eluted with methylene chloride, containing 20–30% of methyl acetate. The compound, which according to thin layer chromatography is a single substance, is lyophilised from dioxane, thin layer chromatogram (silica gel): Rf~0.35 (system: n-butanol/pyridine/acetic acid/water, 40:24:6:30), ultraviolet absorption spectrum (in 95% strength aqueous ethanol): $\lambda_{max}$~265 mμ; infrared absorption spectrum (in mineral oil): characteristic band at 5.66μ.

EXAMPLE 71

The pH value of a mixture of 0.184 g of 7β-amino-3-methoxy-3-cephem-4-carboxylic acid in 4 ml of acetone, 1.6 ml of water and 2.4 ml of an 0.5 molar aqueous dipotassium hydrogen phosphate solution is adjusted to 7.5 by further addition of dipotassium hydrogen phosphate, the mixture is cooled to 0° C. and 0.135 g of the internal anhydride of 1-N-carboxylaminocyclohexanecarboxylic acid is added whilst maintaining the pH value. The mixture is allowed to react for 30 minutes at 0° C., the acetone is removed under reduced pressure, the mixture is covered with ethyl acetate and the pH value of the aqueous phase is adjusted to 2 by addition of 5 molar aqueous phosphoric acid. The organic phase is separated off; the aqueous phase is rinsed with ethyl acetate and then adjusted to pH~4.5 with a 20% strength solution of triethylamine in methanol and diluted with a 1:1 mixture of acetone and diethyl ether. The precipitate is filtered off, washed and dried and yields the internal salt of 7β-(1-amino-cyclohexylcarbonylamino)-3-methoxy-3-cephem-4-carboxylic acid in the amorphous form, thin layer chromatogram (silica gel): Rf~0.2–0.25 (system: n-butanol/acetic acid/water, 67:10:23); ultraviolet absorption spectrum (in 0.1 N hydrochloric acid): $\lambda_{max}$~264 mμ; infrared absorption spectrum (in mineral oil): characteristic band at 5.56μ.

EXAMPLE 72

A mixture of 0.180 g of 7β-bromoacetylamino-3-methoxy-3-cephem-4-carboxylic acid (Example 43), 0.066 g of 4-mercapto-pyridine and 0.057 g of diisopropyl-ethyl-amine in 5 ml of dimethylformamide is allowed to react for 4 hours at room temperature. It is evaporated, the residue is stirred with a 1:1 mixture of acetone and diethyl ether and the product is filtered off and rinsed thoroughly. 3-Methoxy-7β-(4-pyridylthio-acetylamino)-3-cephem-4-carboxylic acid, obtainable in the amorphous form, shows an Rf value of 0.25–0.30 in a thin layer chromatogram (silica gel; system: n-butanol/pyridine/acetic acid/water, 42:24:4:30); infrared absorption spectrum (in mineral oil): characteristic band at 5.65μ.

EXAMPLE 73

A mixture of 0.140 g (0.4 mmol) of 7β-bromoacetylamino-3-methoxy-3-cephem-4-carboxylic acid (Example 43) in 0.5 ml of methanol and 0.047 g (0.5 mmol) of 4-amino-pyridine is reacted in the presence of 0.048 g (0.5 mmol) of diisopropyl-ethyl-amine at 40° C. until the reaction is complete (this being checked by means of thin layer chromatography). The mixture is evaporated, the residue is stirred with a 1:2 mixture of acetone and diethyl ether and the product is filtered off and rinsed thoroughly. 7β-(α-4-Aminopyridinium-acetylamino)-3-methoxy-3-cephem-4-carboxylic acid, obtainable in the amorphous form, which results as the internal salt, shows an Rf value of 0.20–0.3 in a thin layer chromatogram (silica gel; system: n-butanol/pyridine/acetic acid/water, 42:24:4:30); infrared absorption spectrum (in mineral oil): characteristic band at 5.65μ.

EXAMPLE 74

A solution of 7β-bromoacetylamino-3-methoxy-3-cephem-4-carboxylic acid (about 0.15 mmol) obtainable according to the process described in Example 43, in 0.3 ml of a solution of 17.3 ml of diisopropyl-ethyl-amine in 100 ml of methylene chloride, is mixed with 0.0126 g (0.18 mmol) of tetrazole in 0.3 ml of dimethylformamide and the mixture is allowed to react for 30 minutes at room temperature. It is worked up according to the process described in Example 41, and 3-methoxy-7β-(1-tetrazolyl-acetylamino)-3-cephem-4-carboxylic acid is thus obtained, which in a thin layer chromatogram (silica gel; system: n-butanol/pyridine/acetic acid/water 42:24:4:30) shows an Rf value of 0.35-0.45.

EXAMPLE 75

If a solution of 7β-bromoacetylamino-3-methoxy-3-cephem-4-carboxylic acid (about 0.15 mmol), obtainable according to the process described in Example 43, in 0.3 ml of a solution of 17.3 ml of diisopropyl-ethylamine in 100 ml of methylene chloride is reacted with 0.0205 g (0.18 mmol) of 2-mercapto-1-methyl-imidazole in 0.3 ml of dimethylformamide according to the process described in Example 76, the reaction being allowed to take place for 7 hours at 20° C., 3-methoxy-7β-(1-methyl-2-imidazolylthio-acetylamino)-3-cephem-4-carboxylic acid is obtained, which in a thin layer chromatogram (silica gel; system: n-butanol/pyridine/acetic acid/water, 42:24:4:30) shows an Rf value of 0.3-0.4; infrared absorption spectrum (in mineral oil): characteristic band at 5.66μ.

EXAMPLE 76

If a solution of 7β-bromoacetylamino-3-methoxy-3-cephem-4-carboxylic acid (about 0.15 mmol), obtainable according to the process described in Example 43, in 0.3 ml of a solution of 17.3 ml of diisopropyl-ethylamine in 100 ml of methylene chloride is reacted with 0.018 g (0.18 mmol) of 3-mercapto-1,2,4-triazole according to the process described in Example 76, the reaction being allowed to take place for 7 hours at 20° C., 3-methoxy-7β-(1,2,4-triazol-3-ylthioacetylamino)-3-cephem-4-carboxylic acid is obtained, which in a thin layer chromatogram (silica gel; system: n-butanol/pyridine/acetic acid/water, 42:24:4:30) shows an Rf value of 0.3-0.4.

EXAMPLE 77

A solution, prepared at 30° C., of 7β-bromoacetylamino-3-methoxy-3-cephem-4-carboxylic acid (about 0.15 mmol), prepared according to the process described in Example 43, in 10 ml of ethanol and 0.3 ml of water is mixed with a solution of 0.03 g of sodium azide in 0.5 ml of water. The reaction mixture is stirred for 15 hours at room temperature with exclusion of light and is then worked up according to the process described in Example 41. 7β-Azidoacetylamino-3-methoxy-3-cephem-4-carboxylic acid is thus obtained, which in a thin layer chromatogram (silica gel; system: n-butanol/pyridine/acetic acid/water, 42:24:4:30) shows an Rf value of 0.40; ultraviolet absorption spectrum (in ethanol): λ$_{max}$ at 264 mμ; infrared absorption spectrum (in mineral oil): characteristic bands at 4.65μ and 5.64μ.

EXAMPLE 78

A mixture of 1.0 g of 7β-(D-α-amino-α-phenylacetylamino)-3-methoxy-3-cephem-4-carboxylic acid in 10 ml of acetone is treated with 0.8 ml of triethylamine. This mixture is stirred for 24 hours at room temperature and filtered, and the filtrate is then evaporated. The residue is dissolved in water, the pH value is adjusted to 2.5 by means of 2 N hydrochloric acid and the precipitate is then filtered off and dried. 7β-(2,2-Dimethyl-5-oxo-4-phenyl-1,3-diaza-1-cyclopentyl)-3-methoxy-3-cephem-4-carboxylic acid, obtainable as a colourless product, shows an Rf value of 0.40 in a thin layer chromatogram (silica gel) (system: n-butanol/pyridine/acetic acid/water, 40:24:6:30).

EXAMPLE 79

A suspension of 0.100 g of 7β-(D-α-amino-α-phenylacetylamino)-3-methoxy-3-cephem-4-carboxylic acid in 5 ml of absolute methylene chloride is mixed with 0.0364 g of triethylamine and the mixture is stirred for 10 minutes; in the course thereof, most of the material dissolves. The mixture is cooled to −5° C. and a total of 0.0652 g of the triethylamine-sulphur trioxide complex (melting point 89°–90° C.) is added in portions. The whole is stirred for 5 minutes at 0° C. and for two hours at 20° C. This solution is treated with 0.9 mmol of sodium α-ethyl-hexanoate and the product which has separated out is filtered off. After washing with methylene chloride and diethyl ether, the pulverulent precipitate, containing the disodium salt of 3-methoxy-7β-(D-α-sulphoamino-α-phenylacetylamino)-3-cephem-4-carboxylic acid, is dried in a high vacuum; thin layer chromatogram (silica gel): Rf=0.10 (system: n-butanol/acetic acid/water, 71:5:7.5:21); ultraviolet absorption spectrum (in water): λ$_{max}$=267 mμ.

EXAMPLE 80

A solution of 0.037 g of sodium nitrite in 0.4 ml of water is added, whilst stirring, to a cooled solution of 0.100 g of 4-guanylsemicarbazide dihydrochloride in 0.6 ml of water and the mixture is stirred for a further 10 minutes at 0° C. and is then added dropwise at 0° C. to a solution of 0.186 g of 7β-(D-α-amino-α-phenylacetylamino)-3-methoxy-3-cephem-4-carboxylic acid in 4 ml of water which has been adjusted to pH 7.5 with triethylamine. The mixture is stirred for one hour at 0° C. and the precipitate is filtered off, washed with water and dried. The crude 7β-[D-α-(3-guanyl-ureido)-α-phenylacetylamino]-3-methoxy-3-cephem-4-carboxylic acid is thus obtained, which in a thin layer chromatogram (silica gel; development with iodine vapour): shows Rf~0.20–0.30 (system: n-butanol/acetic acid/water, 67:10:23); ultraviolet absorption spectrum (in 95% strength aqueous ethanol): λ$_{max}$=265 mμ.

EXAMPLE 81

Dry ampoules or phials, containing 0.5 g of 3-methoxy-7β-phenylacetylamino-3-cephem-4-carboxylic acid, are manufactured as follows:
Composition (for 1 ampoule or phial)

| | |
|---|---|
| 3-Methoxy-7β-phenylacetylamino-3-cephem-4-carboxylic acid | 0.5 g |
| Mannitol | 0.05 g |

A sterile aqueous solution of the 3-methoxy-7β-phenylacetylamino-3-cephem-4-carboxylic acid and of the mannitol is subjected to freeze-drying under aseptic conditions in 5 ml ampoules or 5 ml phials and the ampoules or phials are sealed and tested.

EXAMPLE 82

Dry ampoules or phials, containing 0.5 g of the internal salt of 3-methoxy-7β-(D-α-phenylglycyl-amino)-3-cephem-4-carboxylic acid are manufactured as follows:
Composition (for 1 ampoule or phial)

Internal salt of
3-methoxy-7β-)D-α-phenylglycyl-amino)-3-cephem-4-carboxylic acid ... 0.5 g Mannitol ... 0.05 g A sterile aqueous solution of the internal salt of 3-methoxy-7β-(D-α-phenylglycyl-amino)-3-cephem-4-carboxylic acid and of the mannitol is subjected to freeze-drying under aseptic conditions in 5 ml ampoules or 5 ml phials and the ampoules or phials are sealed and tested.

EXAMPLE 83

Capsules, containing 0.25 g of the internal salt of 3-methoxy-7β-(D-α-phenylglycyl-amino)-3-cephem-4-carboxylic acid are manufactured as follows:
Composition (for 4,000 capsules):

| | |
|---|---|
| Internal salt of 3-methoxy-7β-(D-α-phenylglycyl-amino)-3-cephem-4-carboxylic acid | 250.000 g |
| Corn starch | 50.000 g |
| Polyvinylpyrrolidone | 15.000 g |
| Magnesium stearate | 5.000 g |
| Ethanol | q.s. |

The internal salt of 3-methoxy-7β-(D-α-phenylglycyl-amino)-3-cephem-4-carboxylic acid and the corn starch are mixed and moistened with a solution of polyvinylpyrrolidone in 50 g of ethanol. The moist mass is forced through a sieve of 3 mm mesh width and dried at 45° C. The dry granules are forced through a sieve of 1 mm mesh width and mixed with 5 g of magnesium stearate. The mixture is filled, in portions of 0.320 g, into push-fit capsules of size 0.

EXAMPLE 84

To 256,3 g of 3-methoxy-7β-(D-α-tert.-butyloxycarbonylamino-α-phenyl-acetylamino)-3-cephem-4-carboxylic acid diphenylmethyl ester is added a mixture of 250 ml of anisol in 1200 ml of methylene chloride; the mixture is treated at 0° with 1200 ml of trifluoroacetic acid, pre-cooled to 0°. The reaction mixture is allowed to stand during 30 minutes at 0° and is diluted over a period of 15 minutes with a total of 12,000 ml of a 1:1 mixture of diethyl ether and petroleum ether, pre-cooled at 0°. The trifluoroacetic acid salt of the 3-methoxy-7β-(D-α-phenyl-glycylamino)-3-cephem-4-carboxylic acid, which precipitates, is filtered off, washed with diethyl ether, dried under reduced pressure and dissolved in 1,900 ml of water. The yellowish impurities are removed by washing the solution with 900 ml of ethyl acetate; the organic washings are discarded and the pH of the aqueous solution (pH ~1,5) is adjusted to 4,5 with a 20% solution of triethylamine in methanol. The inner salt of the 3-methoxy-7β-(D-α-phenyl-glycylamino)-3-cephem-4-carboxylic acid crystallizes as dihydrate in the form of colorless prisms and is filtered off after adding 1,800 ml of acetone and stirring for two hours at 0°, m.p. 175°–177° (with decomposition); $[\alpha]_D^{20} = +138° \pm 1°$ (c=1 in 0,1-n. hydrochloric acid); ultraviolet absorption spectrum (in 0,1-n. aqueous sodium hydrogen carbonate solution: $\lambda_{max} = 265$ mμ (ε=6,500); infrared absorption spectrum (in mineral oil): bands at 2,72μ, 2,87μ, 3.14μ, 3.65μ, 5.68μ, 5,90μ, 6,18μ, 6,27μ, 6,37μ, 6,56μ, 6,92μ, 7,16μ, 7,58μ, 7,74μ, 7,80μ, 8,12μ, 8,30μ, 8,43μ, 8,52μ, 8,65μ, 8,95μ, 9,36μ, 9,55μ, 9,70μ, 10,02μ, 10,38μ, 10,77μ, 11,70μ, 12,01μ, 12,15μ, 12,48μ, 12,60μ, 12,87μ, 13,45μ und 14,30μ; microanalysis ($C_{16}H_{17}O_5N_3S \cdot 2H_2O$; molecular weight: 399,42): calculated: C 48,11%, H 5,30%, N 10,52% and S 8,03%; found: C 47,86%, H, 5,27%, N 10,47% and S 8,00%.

We claim:

1. A process for preparing a cephalosporin ether of the formula

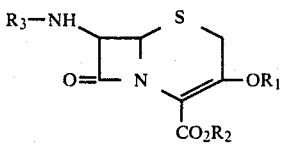

wherein
$R_1$ is $C_1$-$C_4$ alkyl;
$R_2$ is a readily removable ester forming group; and
$R_3$ is a carboxylic acid acyl residue selected from the group consisting of

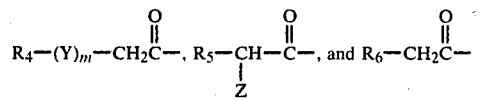

wherein
$R_4$ is phenyl or phenyl substituted by chlorine, bromine, fluorine, iodine hydroxy, nitro, amino, cyano,
Y is O or S, and m is zero or one;
$R_5$ is $R_4$, 2-thienyl or 3-thienyl;
Z is protected hydroxy or protected amino;
$R_6$ is 2-thienyl, 3-thienyl, 2-furyl, 3-furyl or 5-tetrazolyl;
comprising treating a 7-acylamido-3-hydroxy-3-cephem-4-carboxylic acid ester with a non-hydroxylic base selected from the group consisting of alkali metal carbonates or bicarbonates or N-lower alkyl amines,
and a lower alkyl fluorosulfonate in an unreactive organic solvent.

2. The process according to claim 1 wherein the solvent is methylene chloride.

3. The process according to claim 1 wherein the base is potassium carbonate or bicarbonate.

4. The process according to claim 1 wherein the alkylfluorosulfonate is methylfluorosulfonate.

* * * * *